United States Patent
Lee et al.

(10) Patent No.: US 9,758,719 B2
(45) Date of Patent: Sep. 12, 2017

(54) ORGANOMETALLIC COMPOUND AND ORGANIC LIGHT-EMITTING DEVICE INCLUDING THE SAME

(71) Applicant: Samsung Electronics Co., Ltd., Suwon-si, Gyeonggi-do (KR)

(72) Inventors: BangLin Lee, Suwon-si (KR); Hyeonho Choi, Seoul (KR); Youngjae Park, Seoul (KR); Kyuhyun Im, Yongin-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 275 days.

(21) Appl. No.: 14/676,242

(22) Filed: Apr. 1, 2015

(65) Prior Publication Data

US 2016/0141526 A1    May 19, 2016

(30) Foreign Application Priority Data

Nov. 14, 2014  (KR) .................. 10-2014-0158906

(51) Int. Cl.
| | | |
|---|---|---|
| C09K 11/06 | (2006.01) | |
| C07F 15/00 | (2006.01) | |
| H01L 51/00 | (2006.01) | |
| H01L 51/50 | (2006.01) | |

(52) U.S. Cl.
CPC .......... C09K 11/06 (2013.01); C07F 15/0033 (2013.01); H01L 51/0085 (2013.01); *C09K 2211/1007* (2013.01); *C09K 2211/1014* (2013.01); *C09K 2211/1029* (2013.01); *C09K 2211/185* (2013.01); *H01L 51/0081* (2013.01); *H01L 51/5016* (2013.01); *H01L 2251/552* (2013.01)

(58) Field of Classification Search
CPC ............ C09K 11/06; C09K 2211/1007; C09K 2211/1129; C09K 2211/185; C07F 15/0033; H01L 51/0085; H01L 51/0081; H01L 51/5016; H01L 2251/552
See application file for complete search history.

(56) References Cited

U.S. PATENT DOCUMENTS

| | | | | |
|---|---|---|---|---|
| 2012/0264936 A1* | 10/2012 | Inoue et al. | ........ | C07F 15/0086 544/225 |
| 2015/0073142 A1* | 3/2015 | Ohsawa et al. | ..... | H01L 51/0085 544/225 |

FOREIGN PATENT DOCUMENTS

| | | |
|---|---|---|
| KR | 100880220 B1 | 1/2009 |
| KR | 1020120032054 A | 4/2012 |
| KR | 1020130110934 A | 10/2013 |
| KR | 1020130114377 A | 10/2013 |
| KR | 101344787 B1 | 12/2013 |
| KR | 1020140007278 A | 1/2014 |

OTHER PUBLICATIONS

Ki Ho So, et al., "Synthesis and characterization of a new iridium(III) complex with bulky trimethylsilylxylene and applications for efficient yellow-green emitting phosphorescent organic light emitting diodes", Dyes and Pigments 92 (2011) 603-609.

\* cited by examiner

*Primary Examiner* — Nathan M Nutter
(74) *Attorney, Agent, or Firm* — Cantor Colburn LLP

(57) ABSTRACT

An organometallic compound represented by Formula 1:

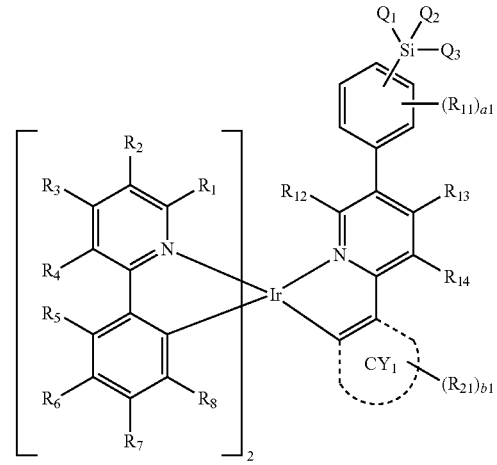

Formula 1 wherein in Formula 1, groups and variables are the same as described in the specification.

20 Claims, 6 Drawing Sheets

ORGANOMETALLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2014-0158906, filed on Nov. 14, 2014, in the Korean Intellectual Property Office, and all the benefits accruing therefrom under 35 U.S.C. §119, the content of which is incorporated herein in its entirety by reference.

BACKGROUND

1. Field

One or more embodiments relate to an organometallic compound and an organic light-emitting device including the same.

2. Description of the Related Art

Organic light emitting devices (OLEDs) are self-emission devices that have wide viewing angles, high contrast ratios, and short response times. In addition, OLEDs exhibit excellent luminance, driving voltage, and response speed characteristics, and produce full-color images.

In an example, an organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons are recombined in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

One or more embodiments relate to a novel organometallic compound and an organic light-emitting device including the same.

Additional aspects will be set forth in part in the description which follows and, in part, will be apparent from the description, or may be learned by practice of the presented exemplary embodiments.

An aspect of exemplary embodiments provides an organometallic compound represented by Formula 1:

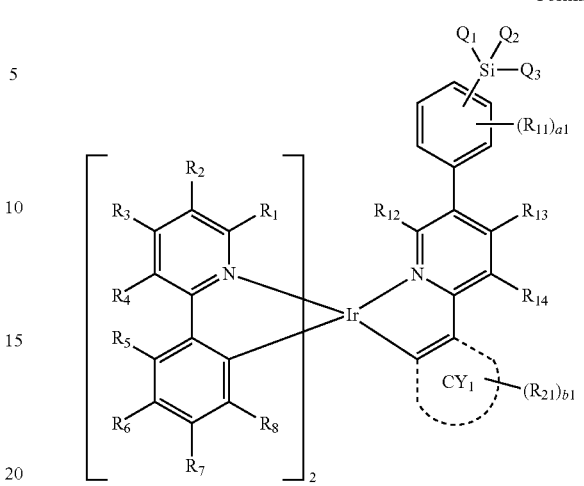

Formula 1 wherein in Formula 1, $CY_1$ may be selected from a $C_5$-$C_{60}$ carbocyclic group and a $C_1$-$C_{60}$ heterocyclic group, $Q_1$ to $Q_3$ may be each independently selected from a $C_1$-$C_{20}$ alkyl group and a phenyl group; and a $C_1$-$C_{20}$ alkyl group and a phenyl group, each substituted with at least one selected from a deuterium, a $C_1$-$C_{10}$ alkyl group, and a phenyl group, $R_1$ to $R_8$ may be each independently selected from a hydrogen, a deuterium, —$CH_3$, —$CDH_2$, —$CD_2H$, and —$CD_3$, $R_{11}$ to $R_{14}$ may be each independently selected from a hydrogen, a deuterium, a $C_1$-$C_{10}$ alkyl group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a phenyl group, and a naphthyl group; and a $C_1$-$C_{10}$ alkyl group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a phenyl group, and a naphthyl group, each substituted with at least one selected from a deuterium, a $C_1$-$C_{10}$ alkyl group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a phenyl group, and a naphthyl group, $R_{21}$ may be selected from a hydrogen, a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group; and —$N(Q_{11})(Q_{12})$ and —$P(=O)(Q_{13})(Q_{14})$, a1 and b1 may be each independently an integer selected from 0 to 4, provided that when a1 is 2 or more, two or more groups $R_{11}$ may be identical or different, and when b1 is 2 or more, 2 or more groups $R_{21}$ may be identical or different, and $Q_{11}$ to $Q_{14}$ may be each independently selected from a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group and a $C_6$-$C_{14}$ aryl group; a $C_6$-$C_{14}$ aryl group substituted with at least one selected from a $C_1$-$C_{20}$ alkyl group and a $C_6$-$C_{14}$ aryl group; and a $C_1$-$C_{14}$ heteroaryl group, a monovalent non-aromatic condensed polycyclic group, and a monovalent non-aromatic condensed heteropolycyclic group.

Another aspect provides an organic light-emitting device including:

a first electrode;

a second electrode; and an organic layer disposed between the first electrode and the second electrode, wherein the organic layer includes an emission layer and includes at least one organometallic compound represented by Formula 1.

The emission layer may include the organometallic compound represented by Formula 1, the organometallic compound represented by Formula 1 included in the emission layer may act as a dopant, and the emission layer may further include a host, wherein an amount of the organometallic compound represented by Formula 1 in the emission layer is smaller than an amount of the host.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
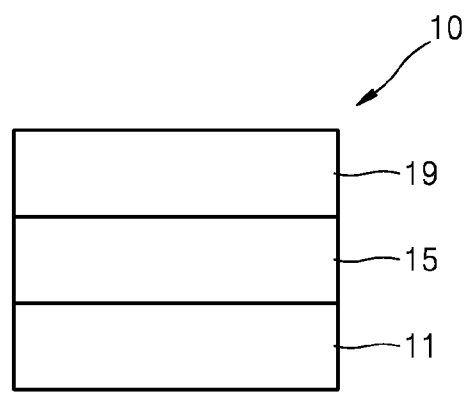
FIG. 1 is a schematic view of an organic light-emitting device according to an embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

An organometallic compound according to an embodiment is represented by Formula 1 below:

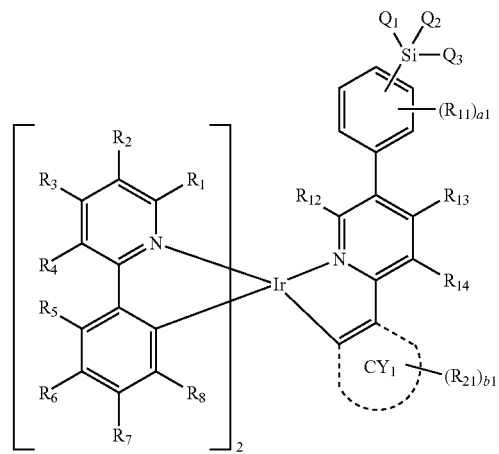

Formula 1

$CY_1$ in Formula 1 may be selected from a $C_5$-$C_{60}$ carbocyclic group and a $C_1$-$C_{60}$ heterocyclic group.

For example, $CY_1$ in Formula 1 may be selected from a benzene, a dibenzofuran, a dibenzothiophene, a fluorene, and a carbazole, but embodiments are not limited thereto.

$Q_1$ to $Q_3$ in Formula 1 may be each independently selected from
a $C_1$-$C_{20}$ alkyl group and a phenyl group; and
a $C_1$-$C_{20}$ alkyl group and a phenyl group, each substituted with at least one selected from a deuterium, a $C_1$-$C_{10}$ alkyl group, and a phenyl group.

For example, $Q_1$ to $Q_3$ in Formula 1 may be each independently selected from
a $C_1$-$C_{10}$ alkyl group and a phenyl group; and
a $C_1$-$C_{10}$ alkyl group and a phenyl group, each substituted with at least one selected from a deuterium and a $C_1$-$C_{10}$ alkyl group.

In some embodiments, $Q_1$ to $Q_3$ in Formula 1 may be each independently selected from
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;
an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group; and
an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group, each substituted with at least one selected from a deuterium and a $C_1$-$C_{10}$ alkyl group, but embodiments are not limited thereto.

In some embodiments, $Q_1$ to $Q_3$ in Formula 1 may all be identical;
$Q_1$ and $Q_3$ may be identical and $Q_2$ and $Q_1$ may be different from each other; or
$Q_1$ to $Q_3$ may all be different from each other.

In some embodiments, $Q_1$ to $Q_3$ in Formula 1 may all be identical, and may be selected from
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group; and an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group, each substituted with at least one selected from a deuterium and a $C_1$-$C_{10}$ alkyl group, but they are not limited thereto.

In some embodiments, $Q_1$ and $Q_3$ in Formula 1 may be each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$, $Q_2$ may be selected from an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group; and an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group, each substituted with at least one selected from a deuterium and a $C_1$-$C_{10}$ alkyl group, but embodiments are not limited thereto.

$R_1$ to $R_8$ in Formula 1 may be each independently selected from a hydrogen, a deuterium, —$CH_3$, —$CDH_2$, —$CD_2H$, and —$CD_3$.

For example, $R_1$ to $R_8$ in Formula 1 may be each independently selected from a hydrogen and a deuterium, but they are not limited thereto.

In some embodiments, in Formula 1, $R_1$ to $R_8$ may all be a hydrogen;

$R_1$, $R_2$, and $R_4$ to $R_8$ may be a hydrogen and $R_3$ may be selected from a deuterium, —$CH_3$, —$CDH_2$, —$CD_2H$, and —$CD_3$;

$R_1$, $R_2$, $R_4$, $R_5$, $R_6$ and $R_8$ may be a hydrogen, and $R_3$ and $R_7$ may be each independently selected from a deuterium, —$CH_3$, —$CDH_2$, —$CD_2H$, and —$CD_3$;

$R_1$ to $R_4$ may be a hydrogen, and $R_5$ to $R_8$ may be each independently selected from a deuterium, —$CH_3$, —$CDH_2$, —$CD_2H$, and —$CD_3$;

$R_1$ to $R_5$ may be a hydrogen, and $R_6$ to $R_8$ may be each independently selected from a deuterium, —$CH_3$, —$CDH_2$, —$CD_2H$, and —$CD_3$;

$R_1$ to $R_4$ and $R_8$ may be a hydrogen, and $R_5$ to $R_7$ may be each independently selected from a deuterium, —$CH_3$, —$CDH_2$, —$CD_2H$, and —$CD_3$; or $R_1$ to $R_8$ may be each independently selected from a deuterium, —$CH_3$, —$CDH_2$, —$CD_2H$, and —$CD_3$, but are not limited thereto.

$R_{11}$ to $R_{14}$ in Formula 1 may be each independently selected from a hydrogen, a deuterium, a $C_1$-$C_{10}$ alkyl group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a phenyl group, and a naphthyl group; and a $C_1$-$C_{10}$ alkyl group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a phenyl group, and a naphthyl group, each substituted with at least one selected from a deuterium, a $C_1$-$C_{10}$ alkyl group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a phenyl group, and a naphthyl group.

For example, $R_{11}$ to $R_{14}$ in Formula 1 may be each independently selected from a hydrogen, a deuterium, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, and a naphthyl group; and a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, and a naphthyl group, each substituted with at least one selected from a deuterium, a $C_1$-$C_{10}$ alkyl group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, and a naphthyl group.

In some embodiments, $R_{11}$ to $R_{14}$ in Formula 1 may be each independently selected from a hydrogen, a deuterium, —$CH_3$, —$CD_3$, —$CD_2H$, —$CDH_2$, a group represented by Formulae 9-1 to 9-17, and a group represented by Formulae 10-1 to 10-12, but embodiments are not limited thereto:

Formula 9-1

Formula 9-2

Formula 9-3

Formula 9-4

Formula 9-5

Formula 9-6

Formula 9-7

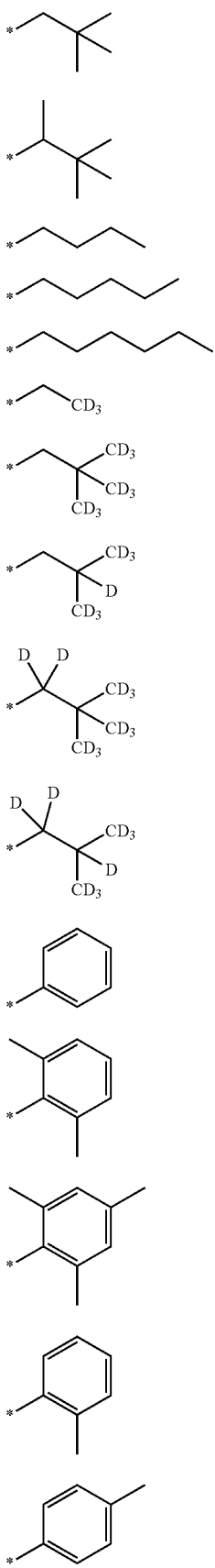
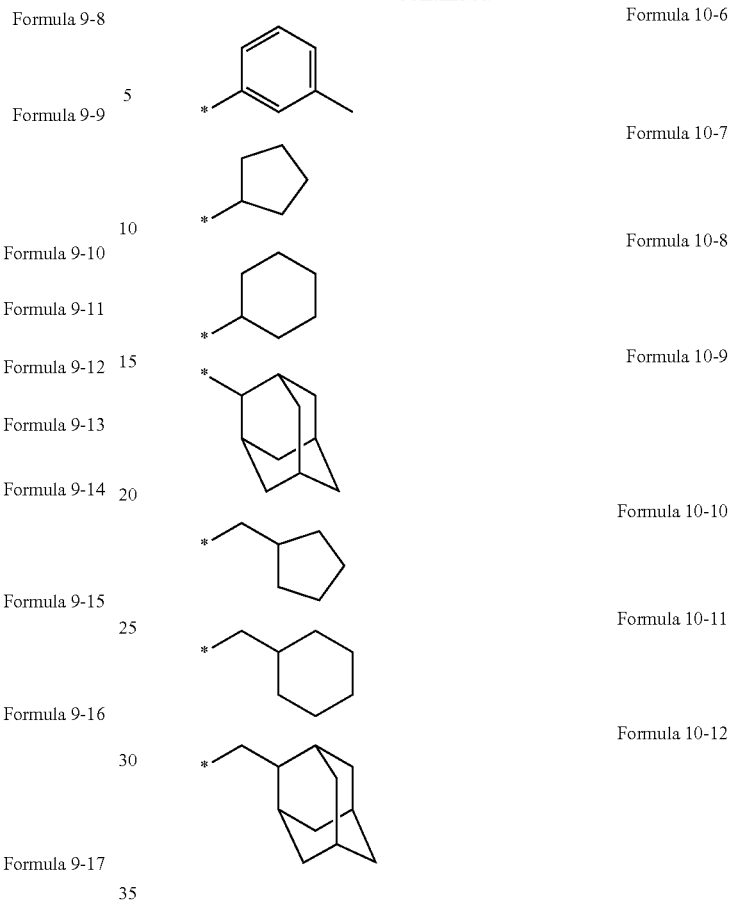

a1 in Formula 1 may be an integer selected from 0 to 4. When a1 is 2 or more, two or more groups $R_{11}$ may be identical or different. For example, a1 in Formula 1 may be 0, 1, or 2.

$R_1$ in Formula 21 may be selected from a hydrogen, a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group; and —N($Q_{11}$)($Q_{12}$) and —P(═O)($Q_{13}$)($Q_{14}$), wherein $Q_{11}$ to $Q_{14}$ are each independently selected from a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, and a $C_6$-$C_{14}$ aryl group; a $C_6$-$C_{14}$ aryl group substituted with at least one selected from a $C_1$-$C_{20}$ alkyl group and a $C_6$-$C_{14}$ aryl group; and a $C_1$-$C_{14}$ heteroaryl group, a monovalent non-aromatic condensed polycyclic group, and a monovalent non-aromatic condensed heteropolycyclic group.

In some embodiments, $R_{21}$ in Formula 1 may be selected from a hydrogen, a deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B($Q_{11}$)($Q_{12}$) and —P(═O)($Q_{13}$)($Q_{14}$), $Q_{11}$ to $Q_{14}$ may be each independently selected from a $C_1$-$C_{20}$ alkyl group, a $C_1$-$C_{20}$ alkoxy group, a phenyl group, a naphthyl group, a pyridinyl group, a pyrimidinyl group, a triazinyl group, and a carbazolyl group; and a phenyl group and a naphthyl group, each substituted with at least one selected from a $C_1$-$C_{20}$ alkyl group, a phenyl group, and a naphthyl group.

In some embodiments, $R_{21}$ in Formula 1 may be selected from a hydrogen, a deuterium, a cyano group, a nitro group, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group, each substituted with at least one selected from a deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a pyridinyl group, and a pyrimidinyl group; and —$B(Q_{11})(Q_{12})$ and —$P(=O)(Q_{13})(Q_{14})$, $Q_{11}$ to $Q_{14}$ may be each independently selected from a $C_1$-$C_{10}$ alkyl group, a $C_1$-$C_{10}$ alkoxy group, a phenyl group, and a naphthyl group; and a phenyl group and a naphthyl group, each substituted with at least one selected from a $C_1$-$C_{20}$ alkyl group, a phenyl group, and a naphthyl group, but they are not limited thereto.

In some embodiments, $R_{21}$ in Formula 1 may be selected from a hydrogen, a deuterium, a cyano group, a nitro group, —$CH_3$, —$CD_3$, —$CD_2H$, —$CDH_2$, —$CF_3$, —$CF_2H$, —$CFH_2$, groups represented by Formulae 9-1 to 9-17, and a group represented by Formulae 10-1 to 10-30, but embodiments are not limited thereto:

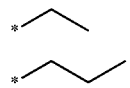

Formula 9-1

Formula 9-2

-continued

Formula 9-3

Formula 9-4

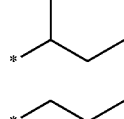

Formula 9-5

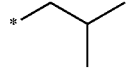

Formula 9-6

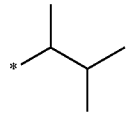

Formula 9-7

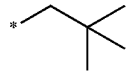

Formula 9-8

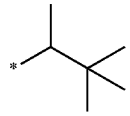

Formula 9-9

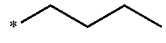

Formula 9-10

Formula 9-11

Formula 9-12

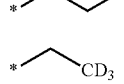

Formula 9-13

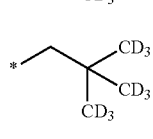

Formula 9-14

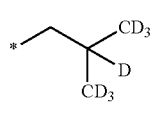

Formula 9-15

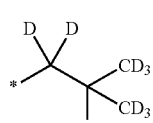

Formula 9-16

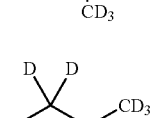

Formula 9-17

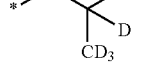

Formula 10-1

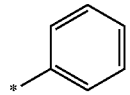

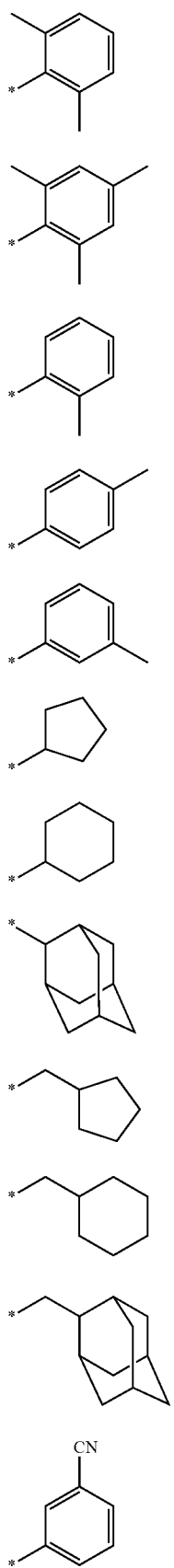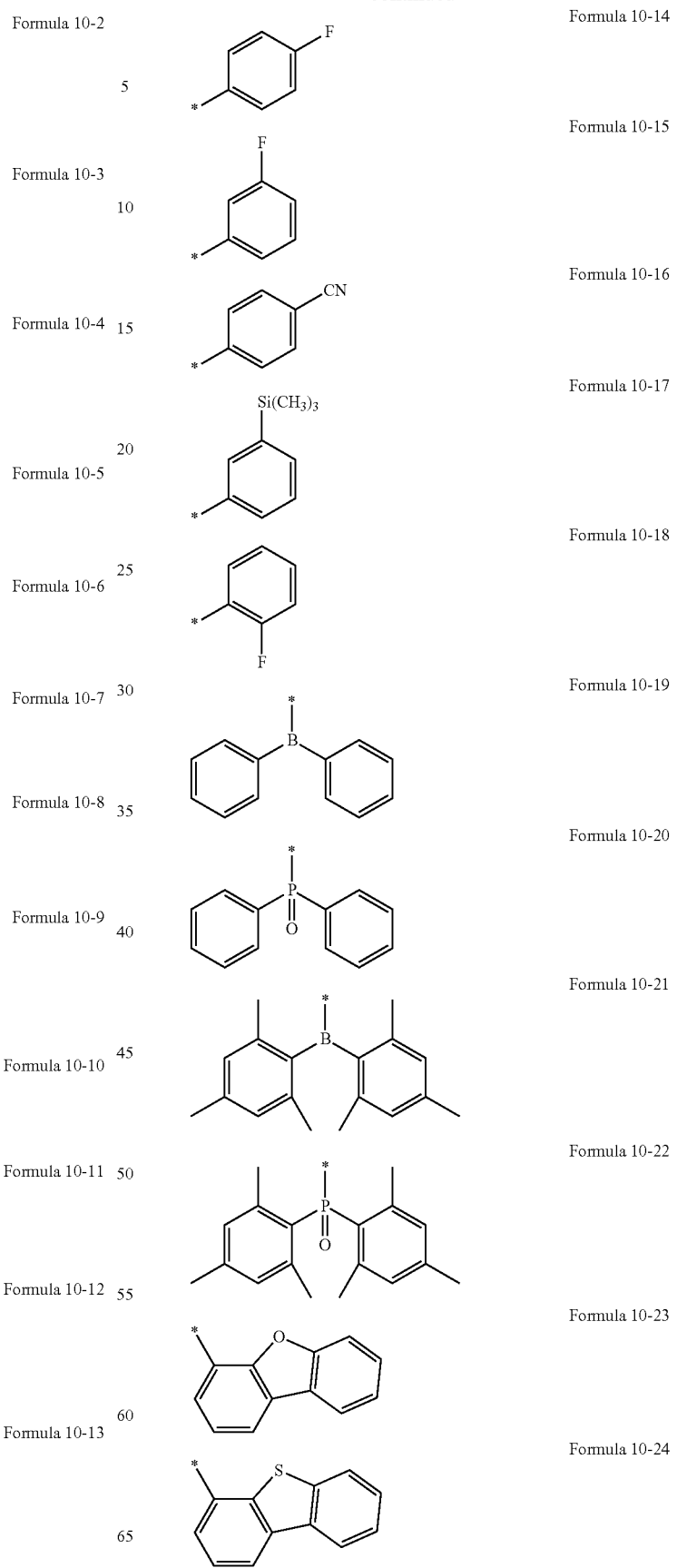

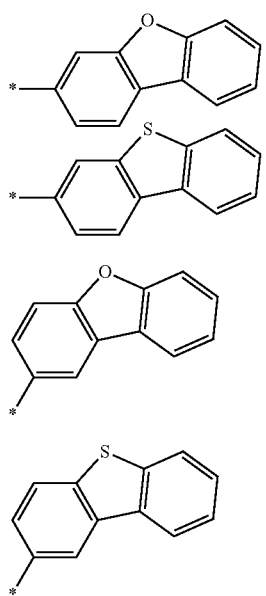
b1 in Formula 1 may be an integer selected from 0 to 4. When b1 is 2 or more, two or more groups $R_{21}$ may be identical or different.
In some embodiments, the organometallic compound represented by Formula 1 may be represented by one of Formulae 1-1 to 1-12:
Formula 1-1
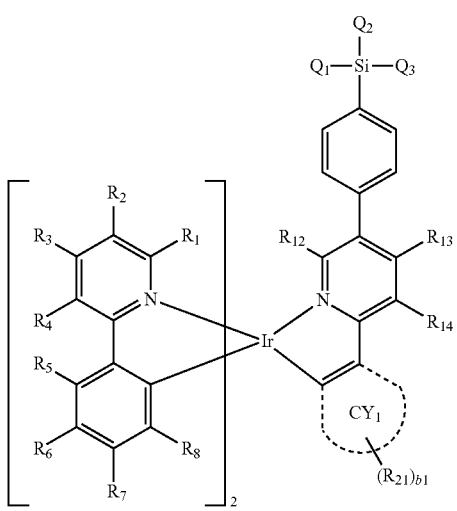
Formula 1-2
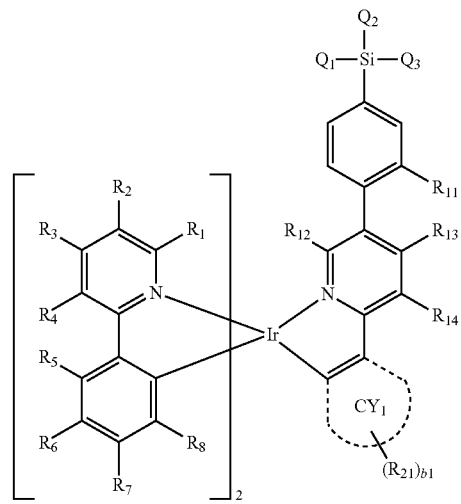
Formula 1-3
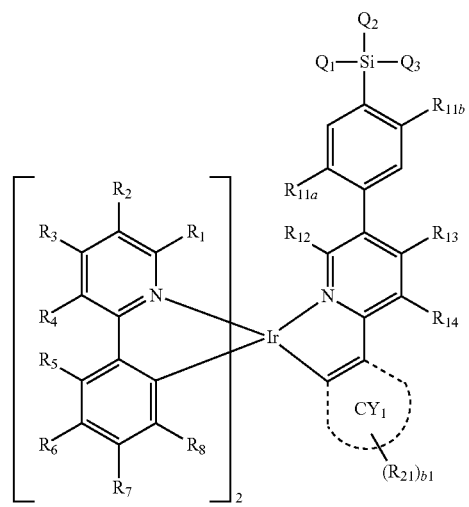
Formula 1-4
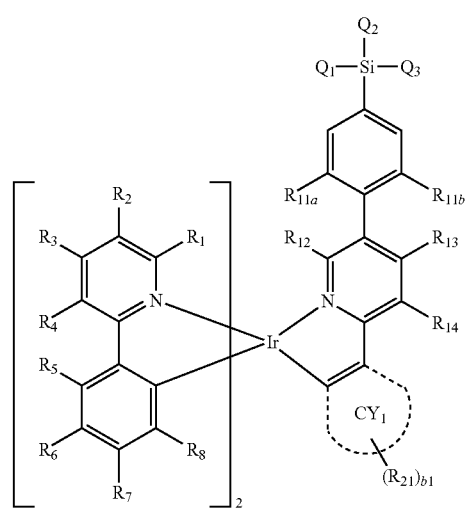

Formula 1-5
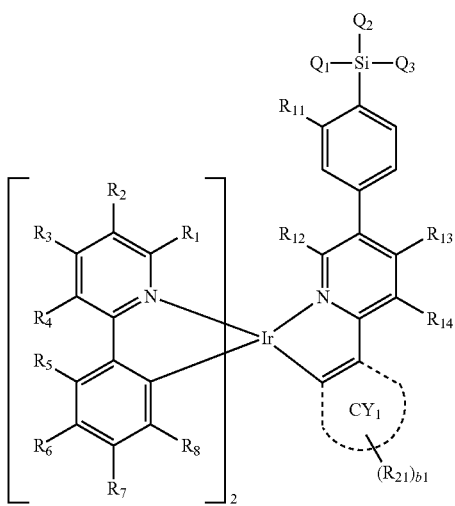
Formula 1-6
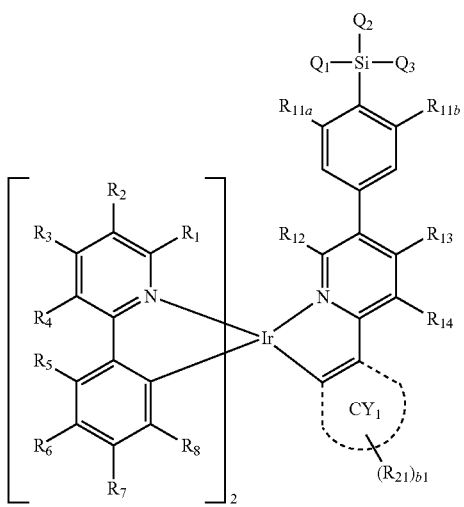
Formula 1-7
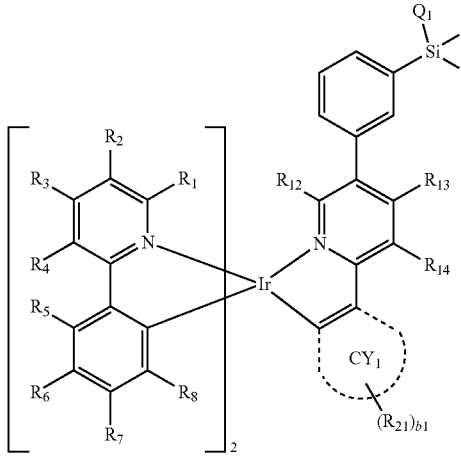
Formula 1-8
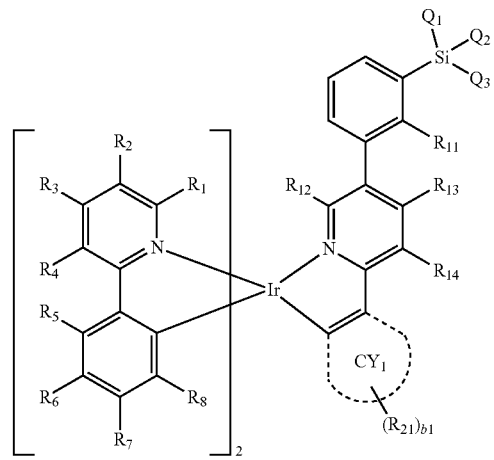
Formula 1-9
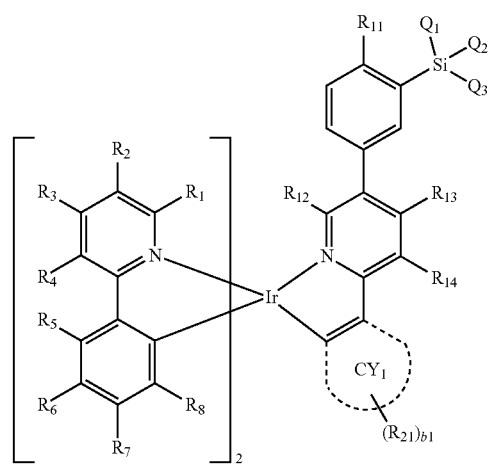
Formula 1-10
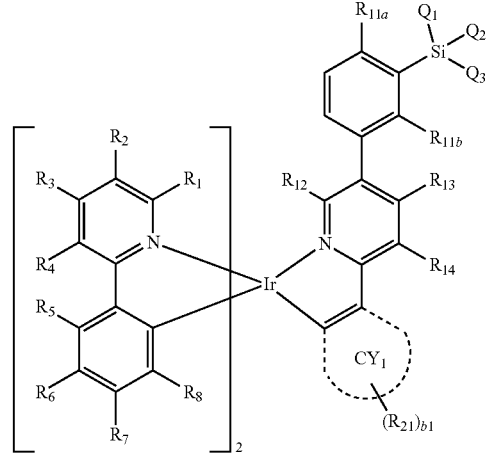

-continued

Formula 1-11

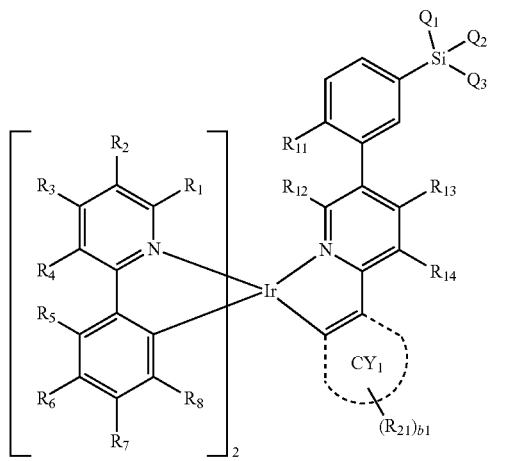

Formula 1-12

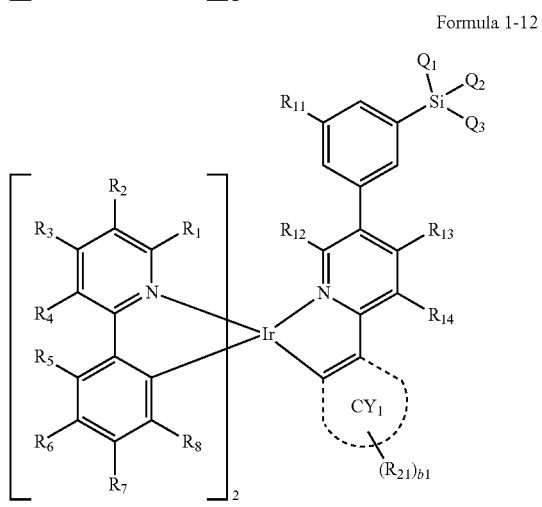

In connection with Formulae 1-1 to 1-12, descriptions of $CY_1$, $Q_1$ to $Q_3$, $R_1$ to $R_8$, $R_{11}$ to $R_{14}$, $R_{21}$, and b1 are the same as described above, and descriptions of $R_{11a}$ and $R_{11b}$ are the same as those of $R_{11}$. In this embodiment, however, $R_{11}$, $R_{11a}$, and $R_{11b}$ in Formulae 1-1 to 1-12 are not a hydrogen.

For example, in Formulae 1-1 and 1-12, $Q_1$ to $Q_3$ may be each independently selected from
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group; and an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group, each substituted with at least one selected from a deuterium and a $C_1$-$C_{10}$ alkyl group, $R_1$ to $R_8$ may all be a hydrogen;

$R_1$, $R_2$, and $R_4$ to $R_8$ may be a hydrogen, and $R_3$ may be selected from a deuterium, —CH$_3$, —CDH$_2$, —CD$_2$H, and —CD$_3$;

$R_1$, $R_2$, $R_4$, $R_5$, $R_6$ and $R_8$ may be a hydrogen, and $R_3$ and $R_7$ may be each independently selected from a deuterium, —CH$_3$, —CDH$_2$, —CD$_2$H, and —CD$_3$;

$R_1$ to $R_4$ may be a hydrogen, and $R_5$ to $R_8$ may be each independently selected from a deuterium, —CH$_3$, —CDH$_2$, —CD$_2$H, and —CD$_3$;

$R_1$ to $R_5$ may be a hydrogen, and $R_6$ to $R_8$ may be each independently selected from a deuterium, —CH$_3$, —CDH$_2$, —CD$_2$H, and —CD$_3$;

$R_1$ to $R_4$ and $R_8$ may be a hydrogen, and $R_5$ to $R_7$ may be each independently selected from a deuterium, —CH$_3$, —CDH$_2$, —CD$_2$H, and —CD$_3$; or $R_1$ to $R_8$ may be each independently selected from a hydrogen, a deuterium, —CH$_3$, —CDH$_2$, —CD$_2$H, and —CD$_3$, $R_{11}$, $R_{11a}$, $R_{11b}$, $R_{12}$, $R_{13}$ and $R_{14}$ may be each independently selected from a hydrogen, a deuterium, —CH$_3$, —CD$_3$, —CD$_2$H, —CDH$_2$, groups represented by Formulae 9-1 to 9-17, and a group represented by Formulae 10-1 to 10-12 (provided that $R_{11}$, $R_{11a}$ and $R_{11b}$ are not a hydrogen), and $R_{21}$ may be selected from a hydrogen, a deuterium, a cyano group, a nitro group, —CH$_3$, —CD$_3$, —CD$_2$H, —CDH$_2$, —CF$_3$, —CF$_2$H, —CFH$_2$, groups represented by Formulae 9-1 to 9-17, and groups represented by Formulae 10-1 to 10-30.

In some embodiments, the organometallic compound represented by Formula 1 may be represented by one of Formulae 1(1) to 1(12):

Formula 1(1)

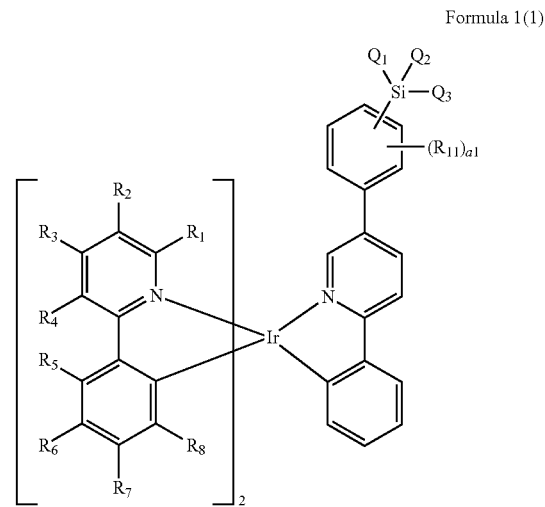

Formula 1(2)

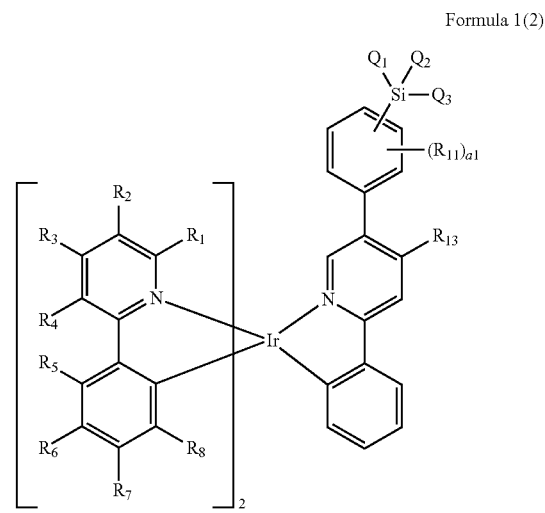

Formula 1(3)
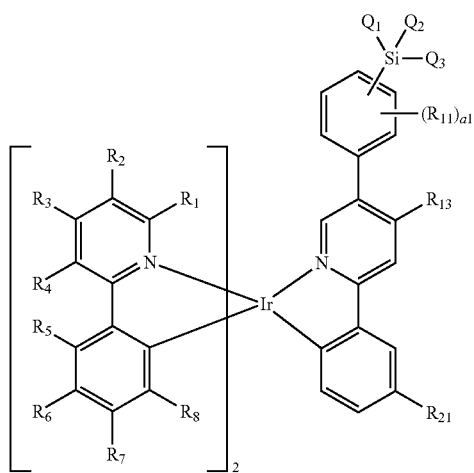
Formula 1(4)
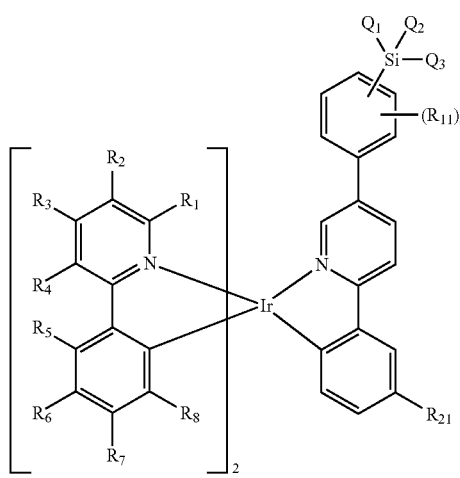
Formula 1(5)
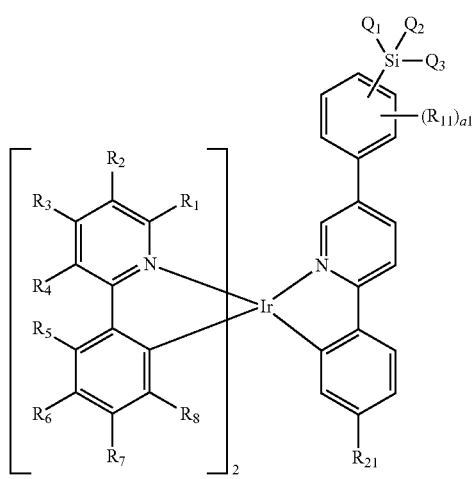
Formula 1(6)
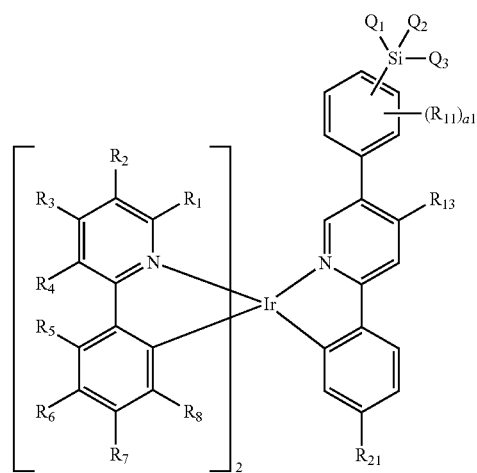
Formula 1(7)
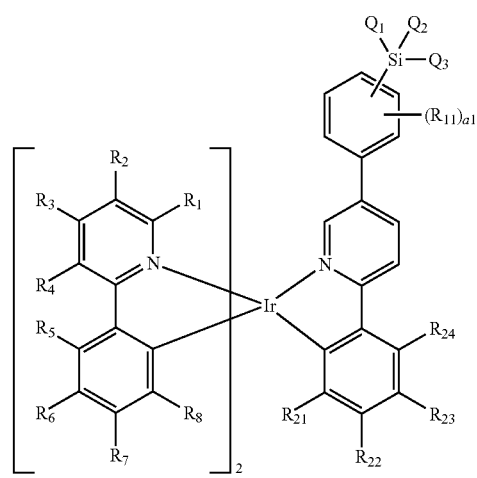
Formula 1(8)
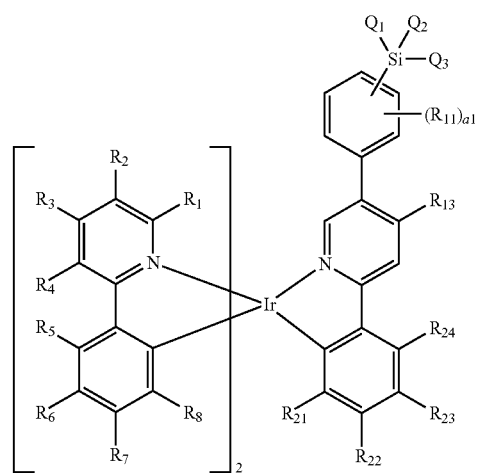

Formula 1(9)

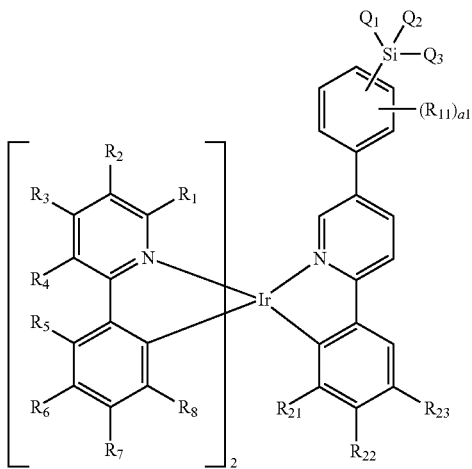

Formula 1(10)

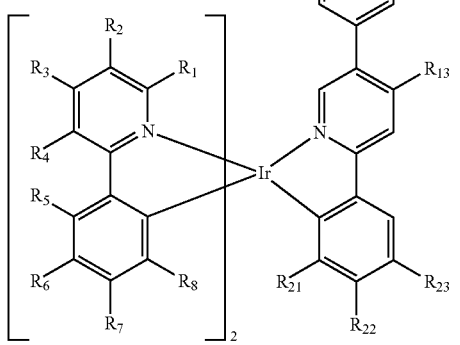

Formula 1(11)

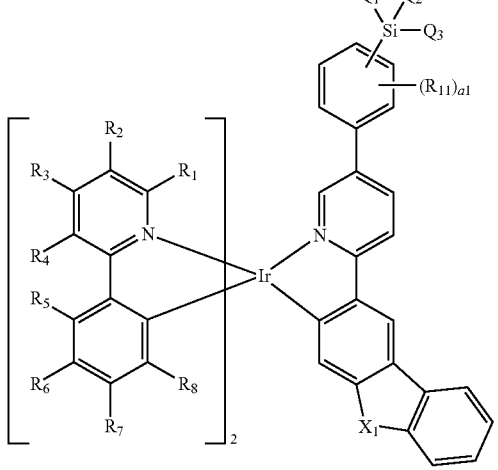

Formula 1(12)

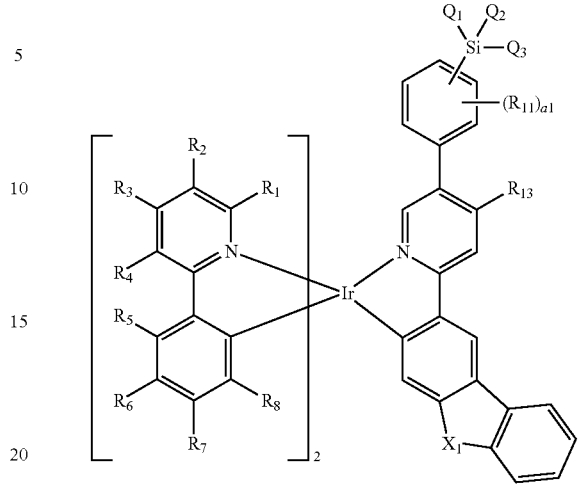

In connection with Formulae 1(1) to 1(12), descriptions of $Q_1$ to $Q_3$, $R_1$ to $R_8$, $R_{11}$, a1, $R_{13}$ and $R_{21}$ are the same as described above, $X_1$ may be $N(R_{21})$, O, or S, and descriptions of $R_{22}$ to $R_{24}$ are the same as those of $R_{21}$, provided that $R_{13}$ and $R_{21}$ to $R_{24}$ in Formulae 1(1) to 1(12) are not be a hydrogen.

For example, in Formulae 1(1) and 1(12), $Q_1$ to $Q_3$ may be each independently selected from
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group; and an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group, each substituted with at least one selected from a deuterium and a $C_1$-$C_{10}$ alkyl group, $R_1$ to $R_8$ may all be a hydrogen;

$R_1$, $R_2$, and $R_4$ to $R_8$ may be a hydrogen, and $R_3$ may be selected from a deuterium, —CH$_3$, —CDH$_2$, —CD$_2$H, and —CD$_3$;

$R_1$, $R_2$, $R_4$, $R_5$, $R_6$ and $R_8$ may be a hydrogen, and $R_3$ and $R_7$ may be each independently selected from a deuterium, —CH$_3$, —CDH$_2$, —CD$_2$H, and —CD$_3$;

$R_1$ to $R_4$ may be a hydrogen, and $R_5$ to $R_8$ may be each independently selected from a deuterium, —CH$_3$, —CDH$_2$, —CD$_2$H, and —CD$_3$;

$R_1$ to $R_5$ may be a hydrogen, and $R_6$ to $R_8$ may be each independently selected from a deuterium, —CH$_3$, —CDH$_2$, —CD$_2$H, and —CD$_3$;

$R_1$ to $R_4$ and $R_8$ may be a hydrogen, and $R_5$ to $R_7$ may be each independently selected from a deuterium, —CH$_3$, —CDH$_2$, —CD$_2$H, and —CD$_3$; or $R_1$ to $R_8$ may be each independently selected from a deuterium, —CH$_3$, —CDH$_2$, —CD$_2$H, and —CD$_3$, $R_{11}$ and $R_{13}$ may be each independently selected from a hydrogen, a deuterium, —CH$_3$, —CD$_3$, —CD$_2$H, —CDH$_2$, a group represented by Formulae 9-1 to 9-17, and a group represented by Formulae 10-1 to 10-12 (provided that $R_{13}$ is not a hydrogen), $R_{21}$ to $R_{24}$ may be each independently selected from a deuterium, a cyano group, a nitro group, —$CH_3$, —$CD_3$, —$CD_2H$, —$CDH_2$, —$CF_3$, —$CF_2H$, —$CFH_2$, groups represented by Formulae 9-1 to 9-17, and groups represented by Formulae 10-1 to 10-30, and a1 may be 0, 1, or 2.

In some embodiments, the organometallic compound represented by Formula 2 may be represented by one of Formulae 2-1 to 2-72:

Formula 2-1

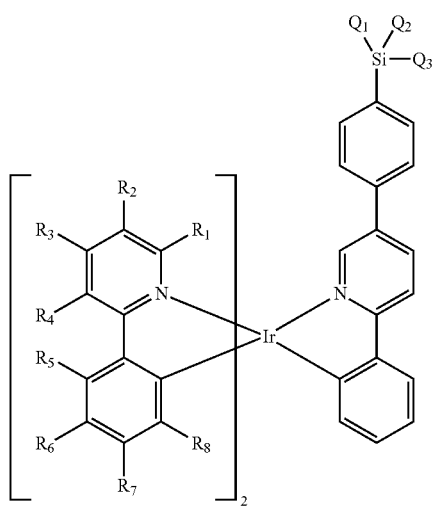

Formula 2-2

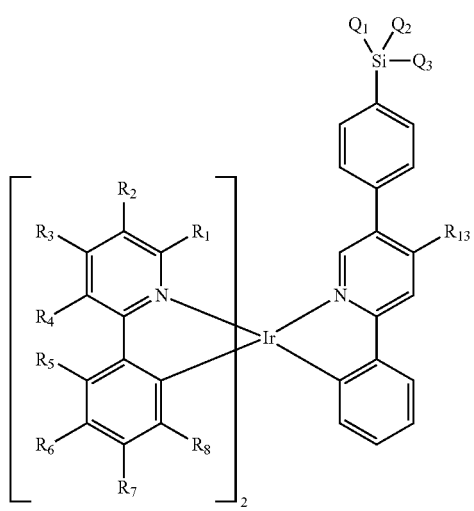

Formula 2-3

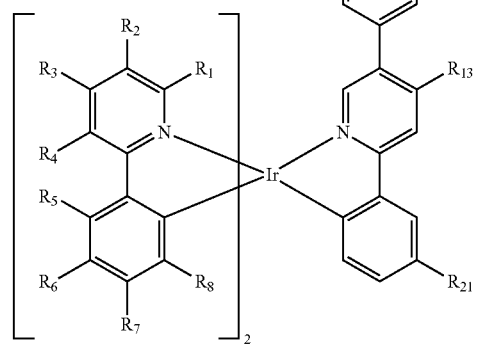

Formula 2-4

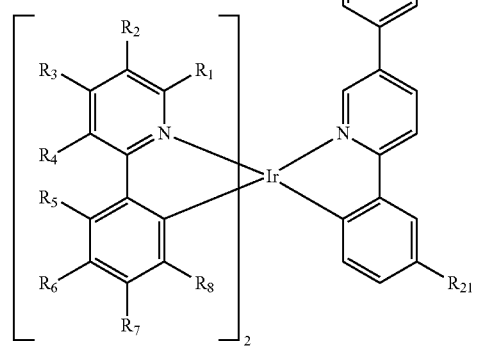

Formula 2-5

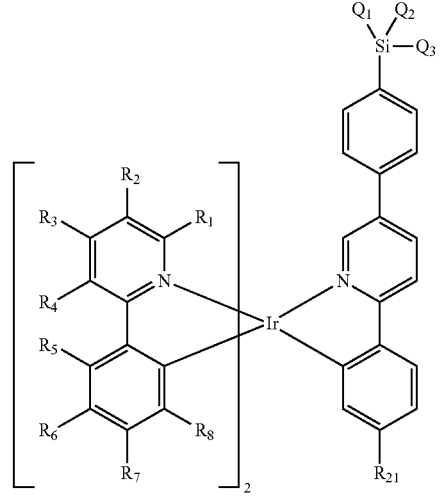

Formula 2-6
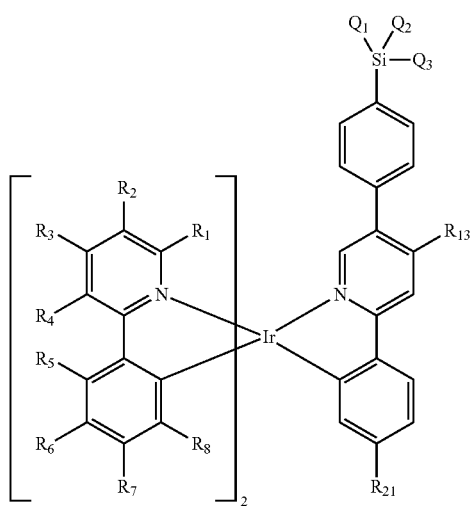
Formula 2-7
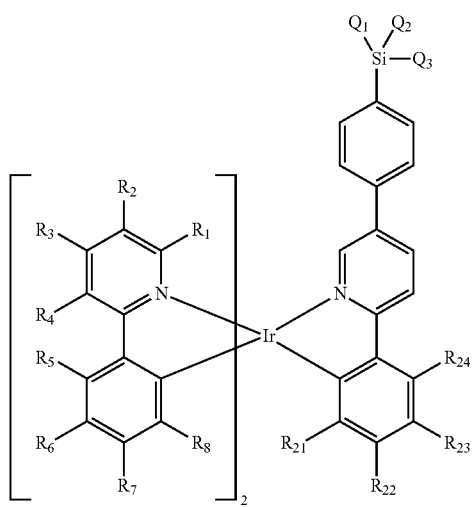
Formula 2-8
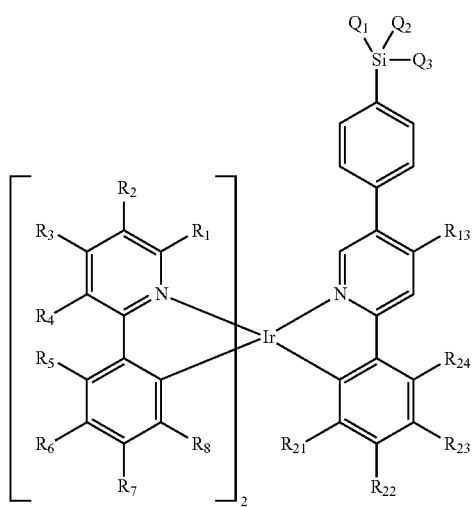
Formula 2-9
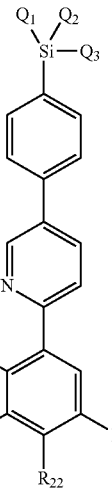
Formula 2-10
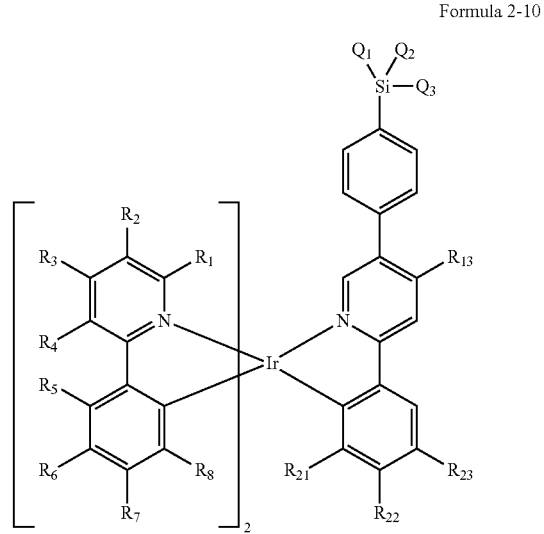
Formula 2-11
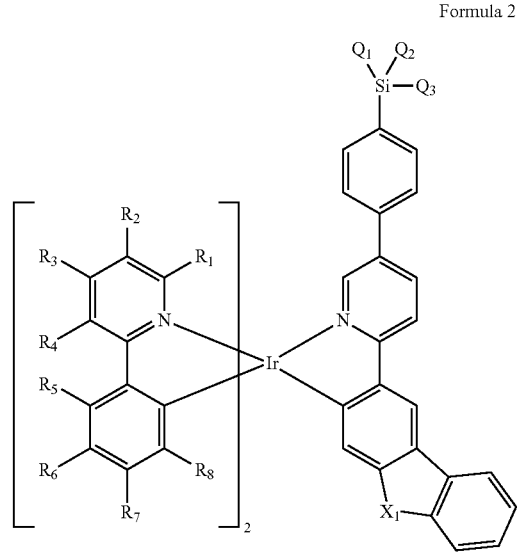

Formula 2-12
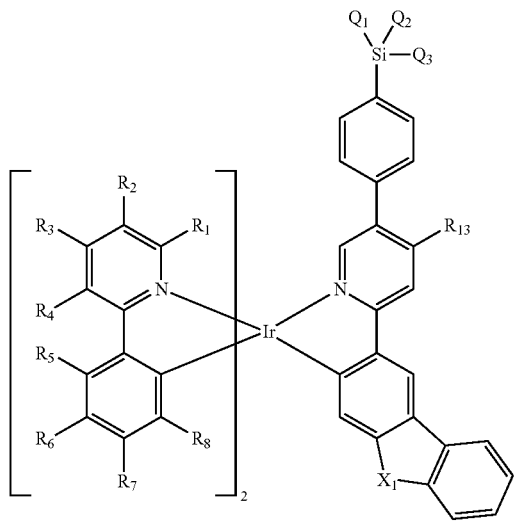
Formula 2-15
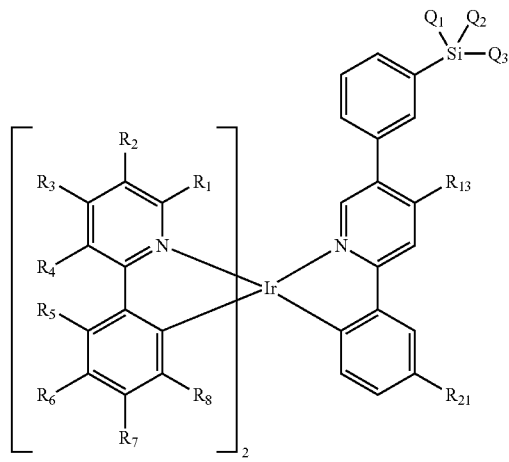
Formula 2-13
Formula 2-16
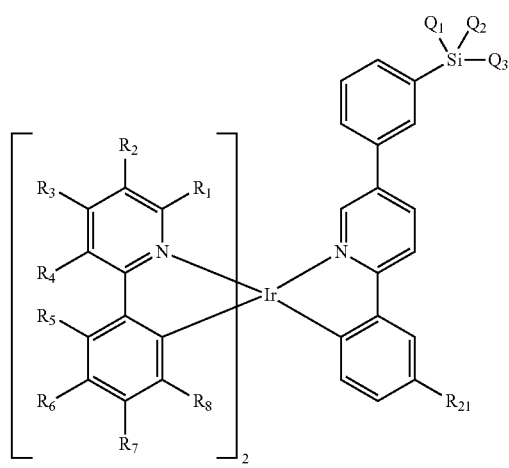
Formula 2-14
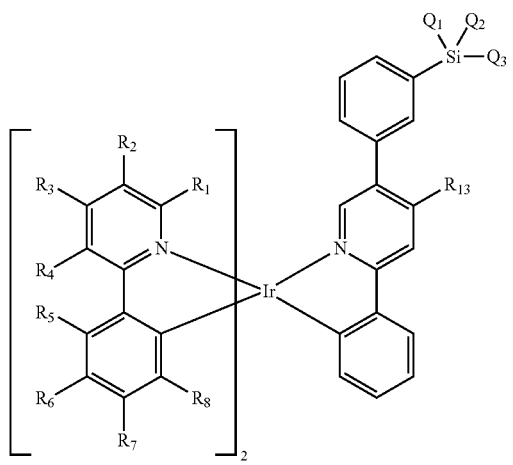
Formula 2-17
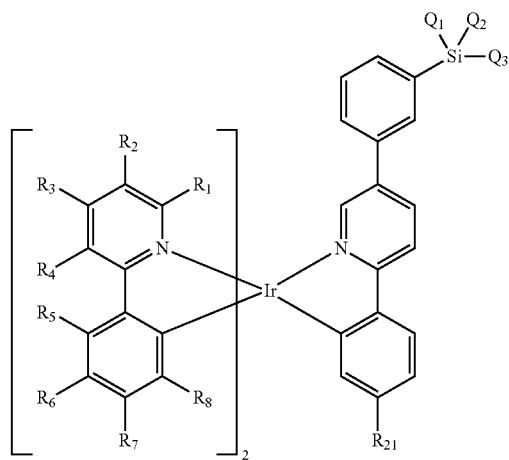

Formula 2-18
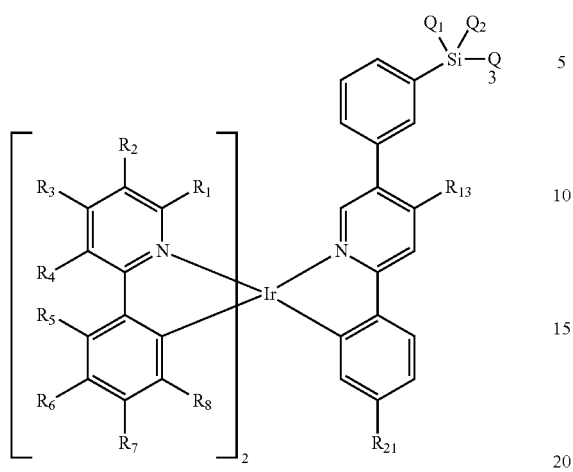
Formula 2-19
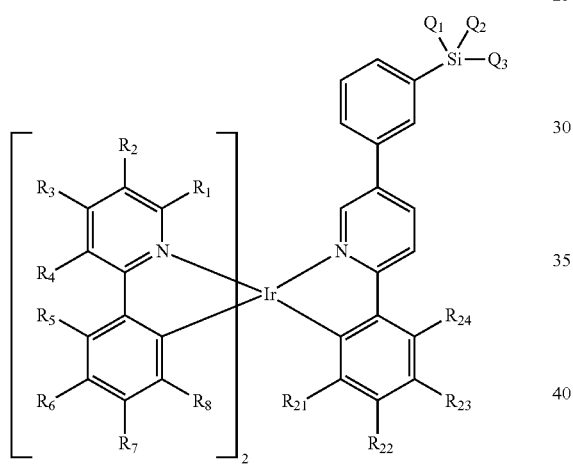
Formula 2-20
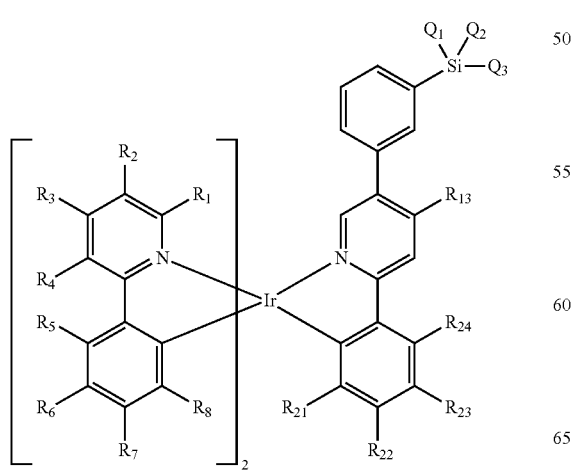
Formula 2-21
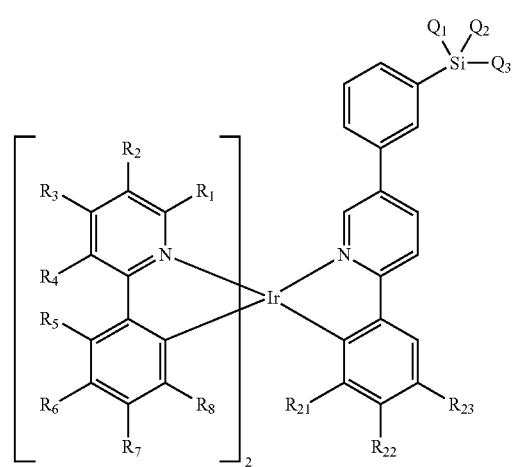
Formula 2-22
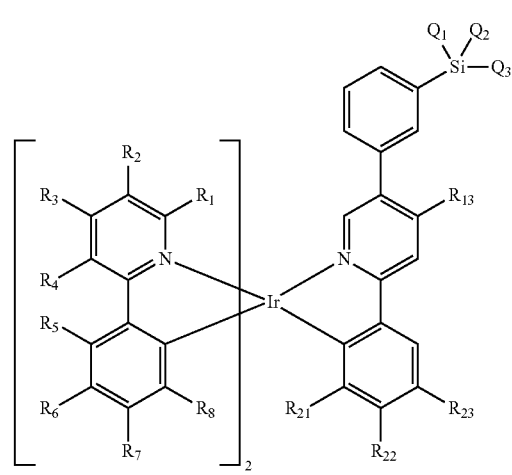
Formula 2-23
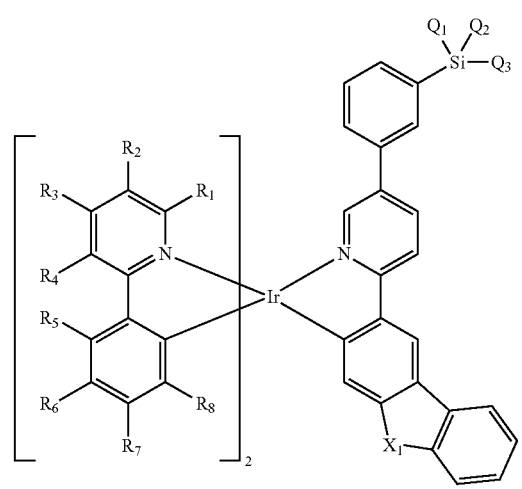

Formula 2-24
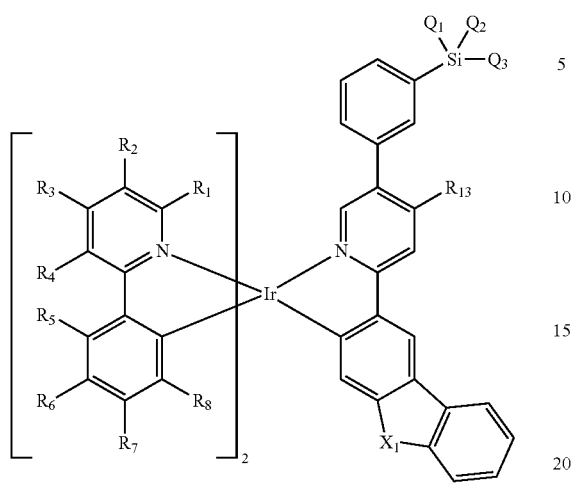
Formula 2-27
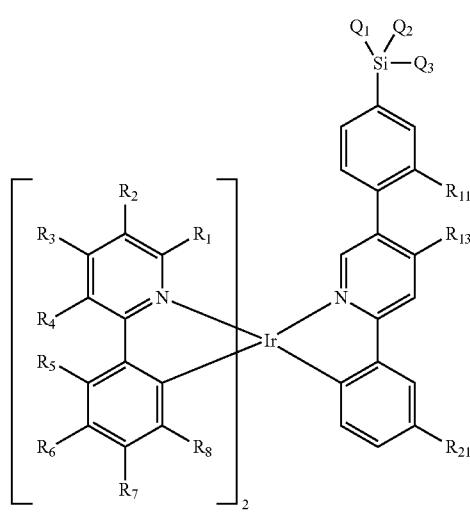
Formula 2-25
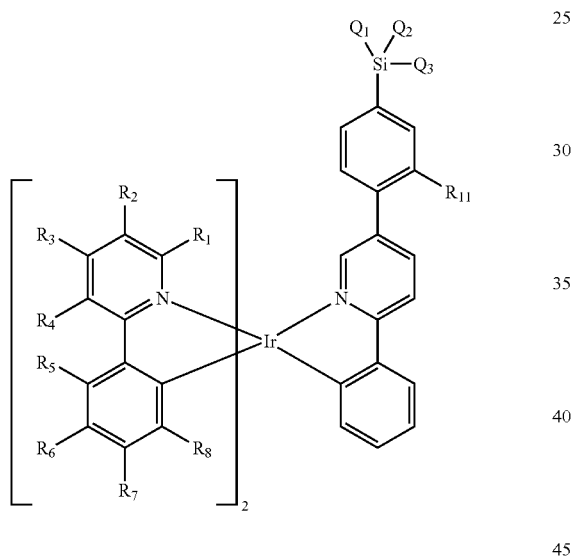
Formula 2-28
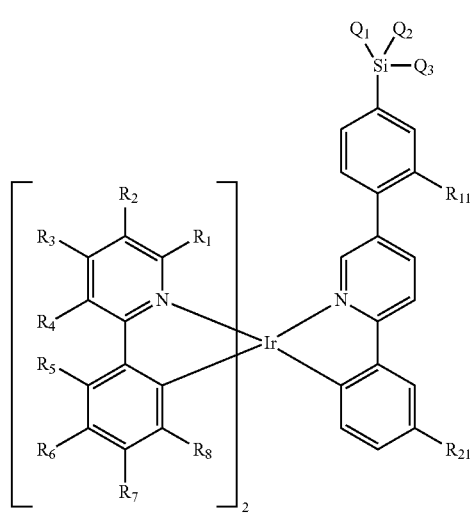
Formula 2-26
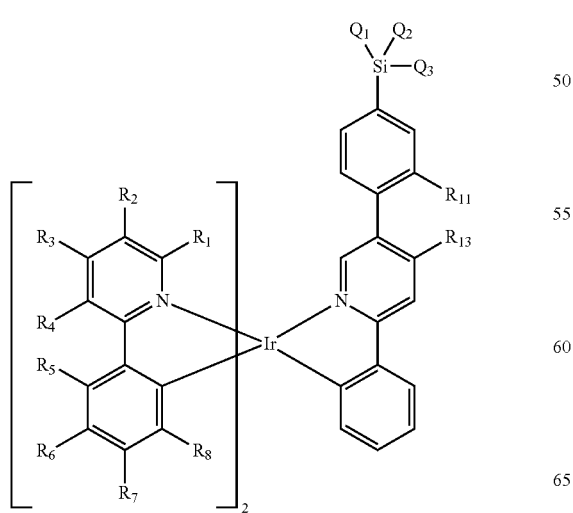
Formula 2-29
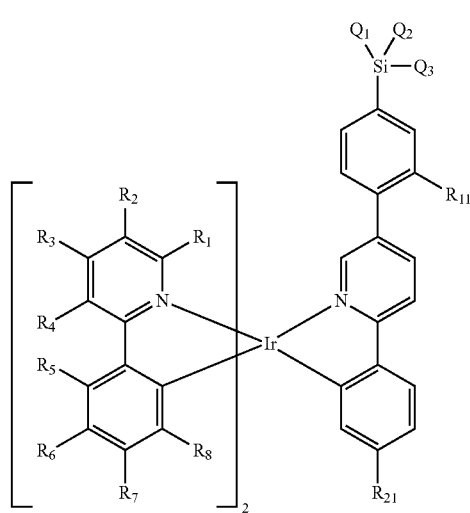

Formula 2-30
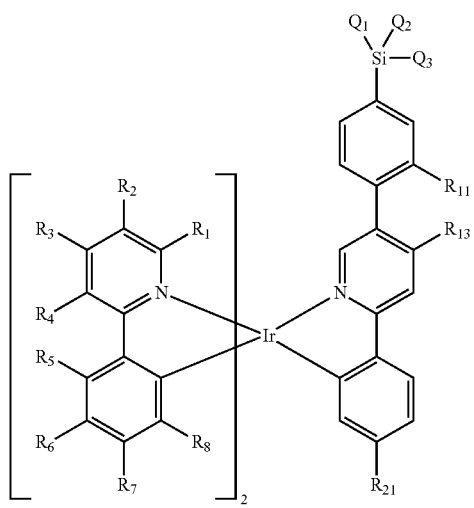
Formula 2-31
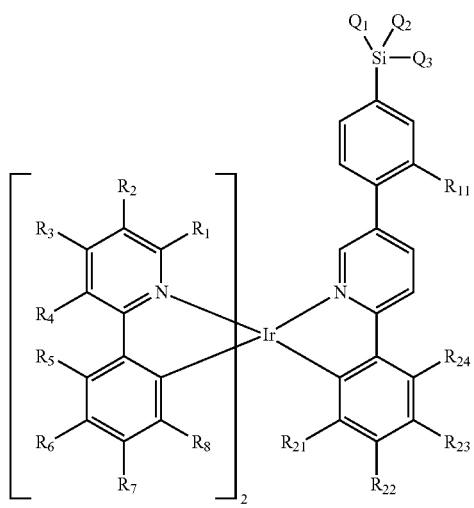
Formula 2-32
Formula 2-33
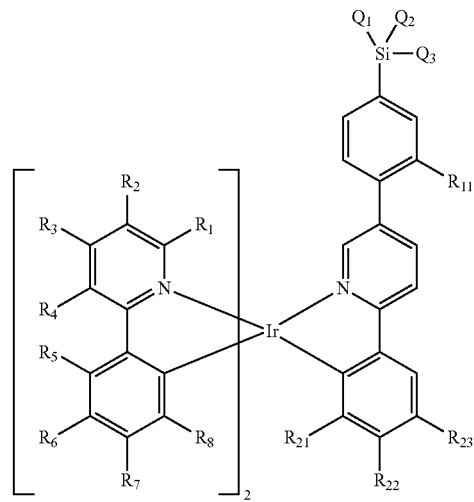
Formula 2-34
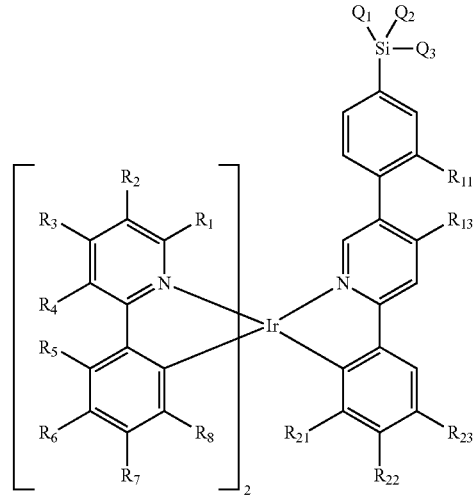
Formula 2-35
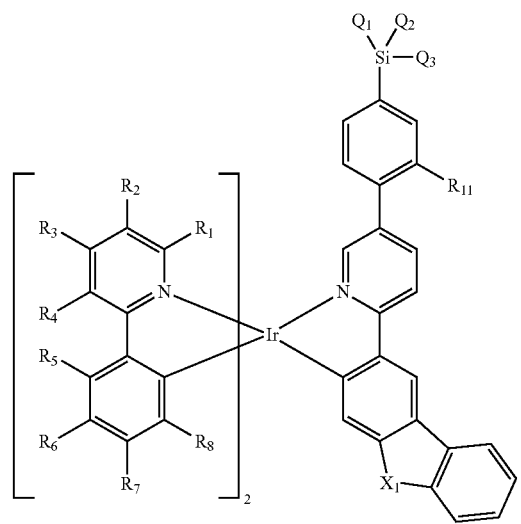

Formula 2-36
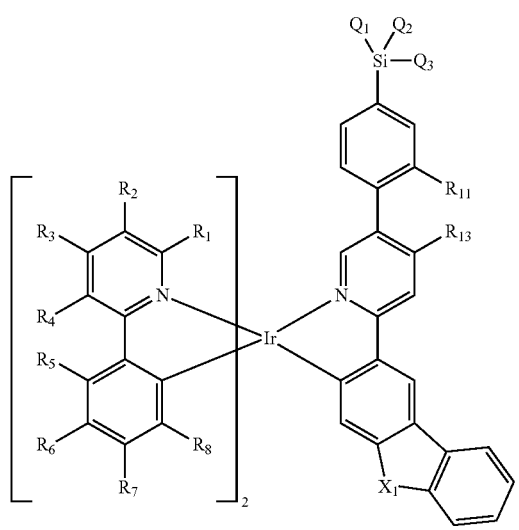
Formula 2-37
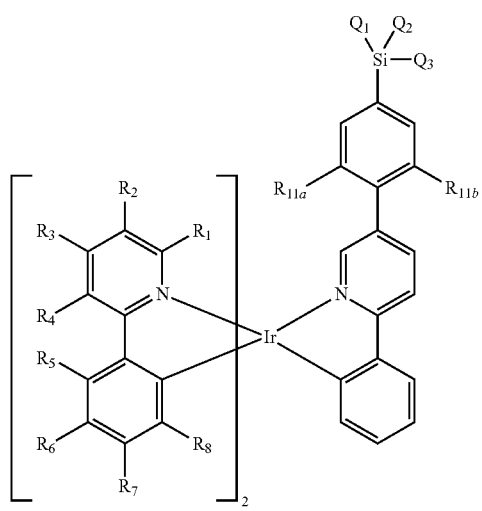
Formula 2-38
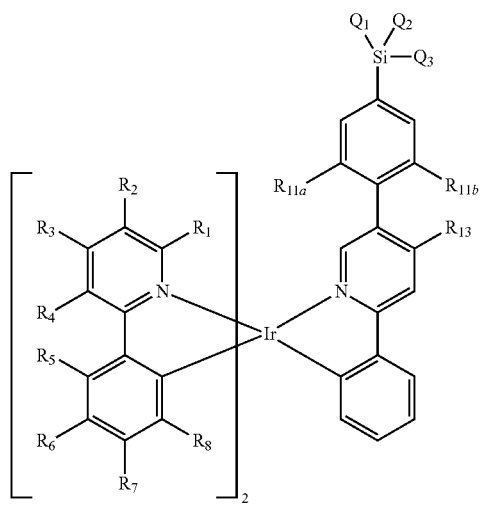
Formula 2-39
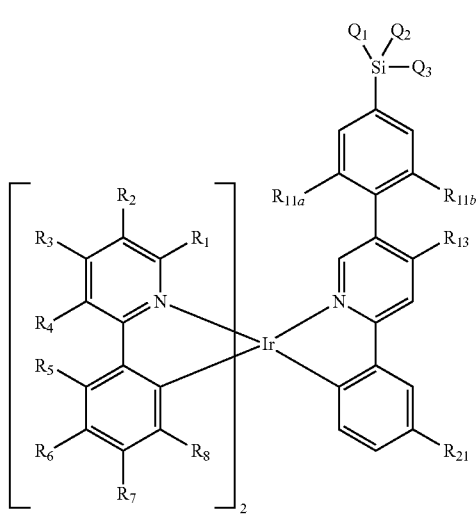
Formula 2-40
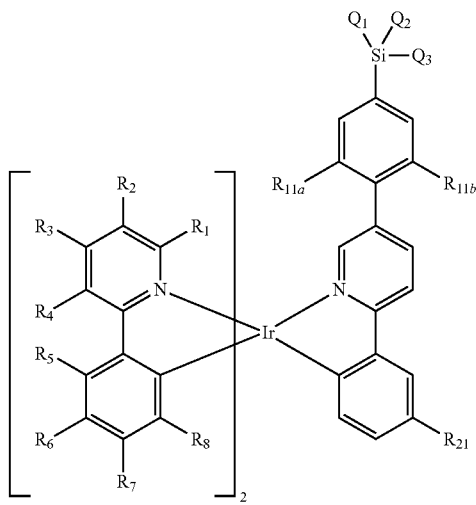
Formula 2-41
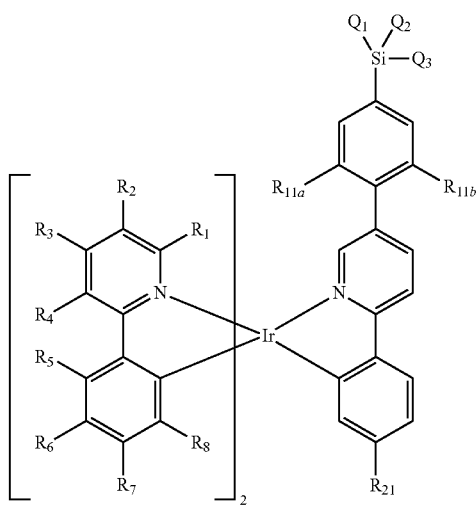

Formula 2-42
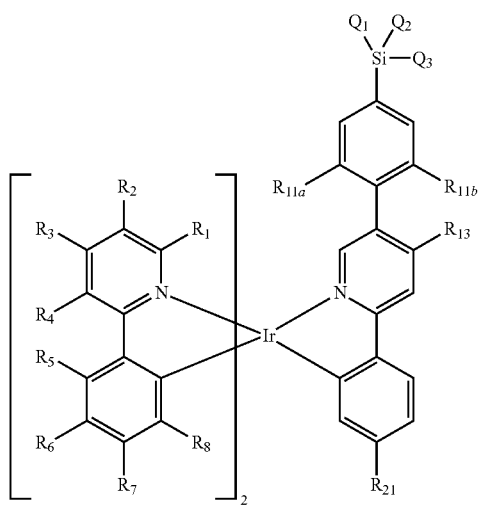
Formula 2-43
Formula 2-44
Formula 2-45
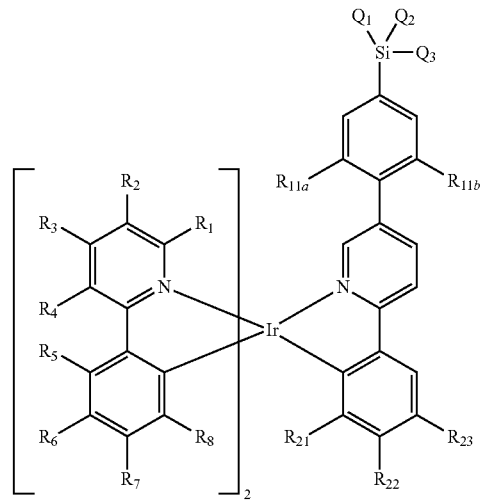
Formula 2-46
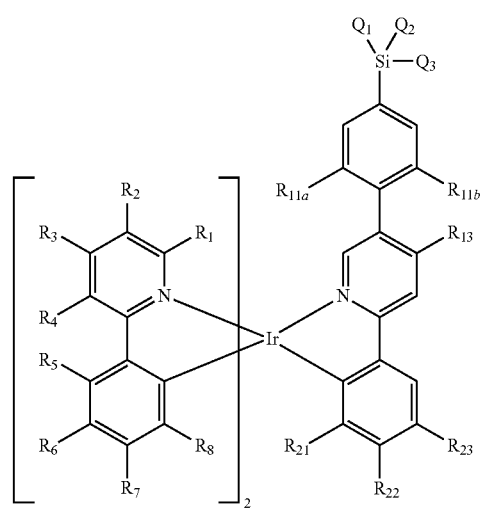
Formula 2-47
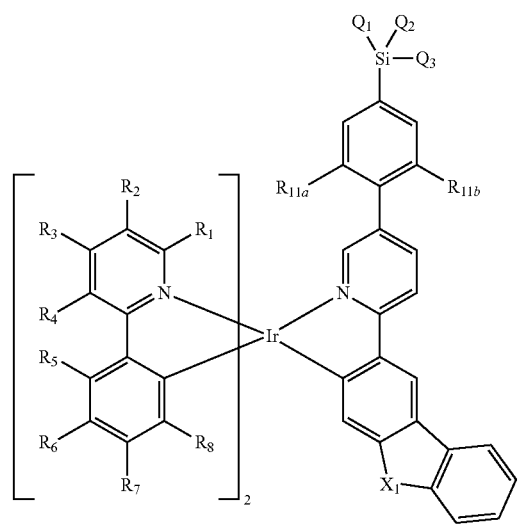
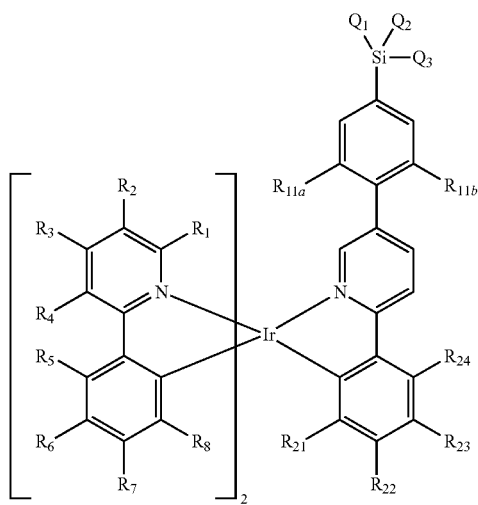

Formula 2-48
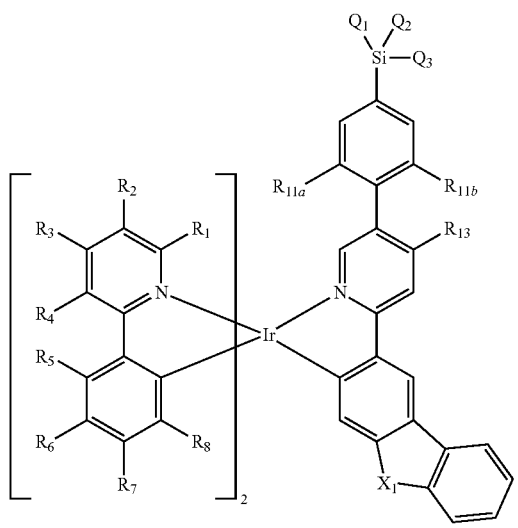
Formula 2-49
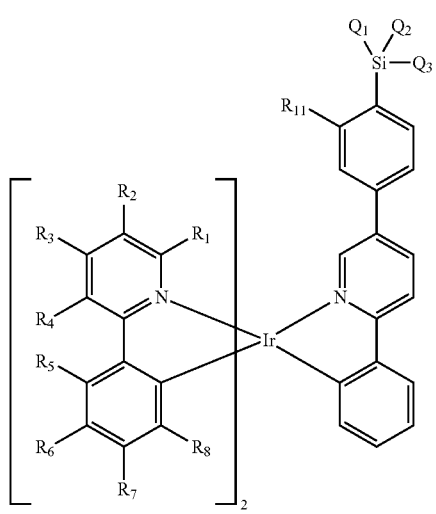
Formula 2-50
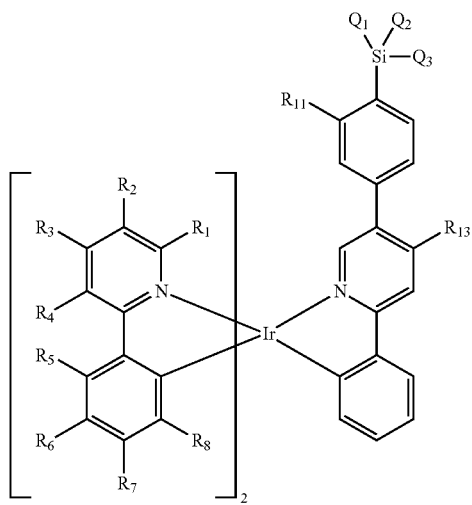
Formula 2-51
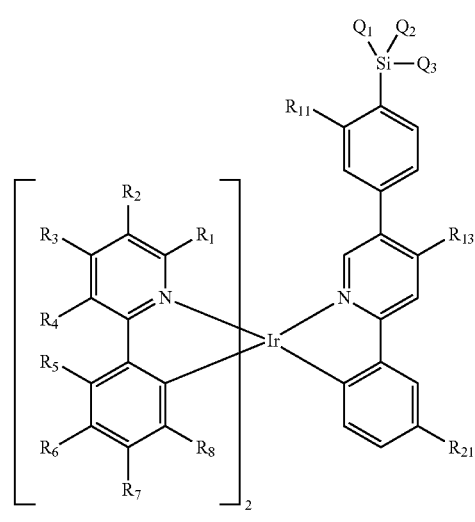
Formula 2-52
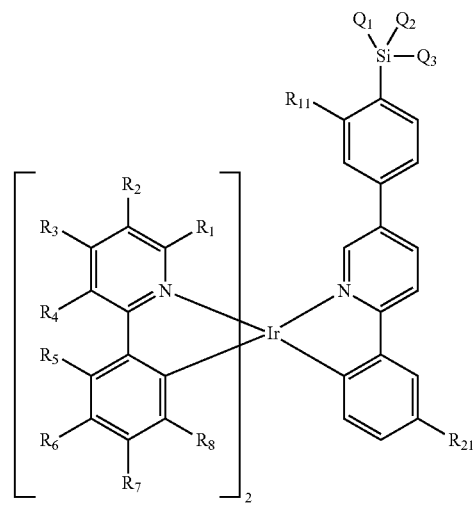
Formula 2-53
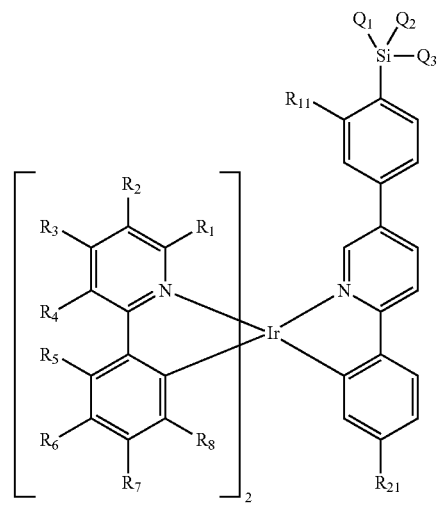

Formula 2-54
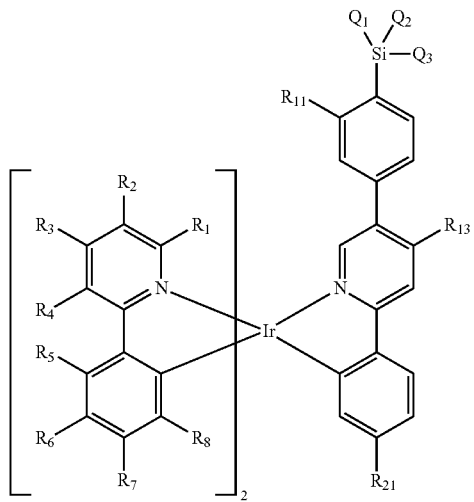
Formula 2-55
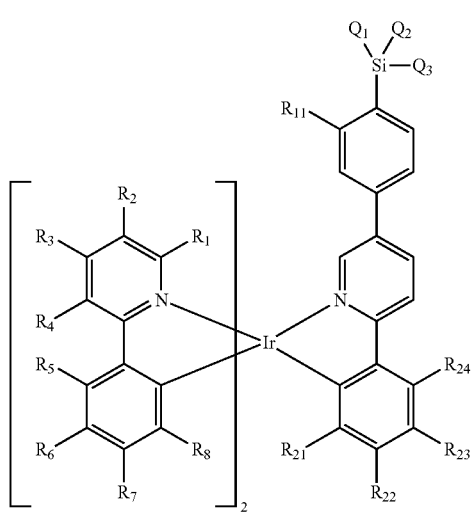
Formula 2-56
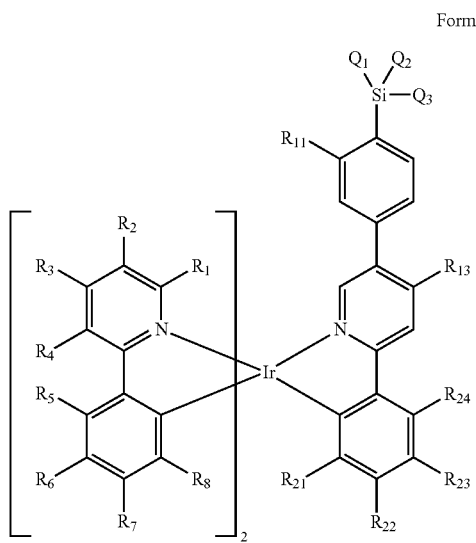
Formula 2-57
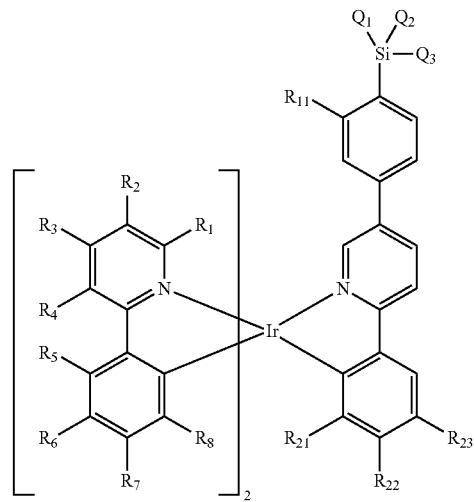
Formula 2-58
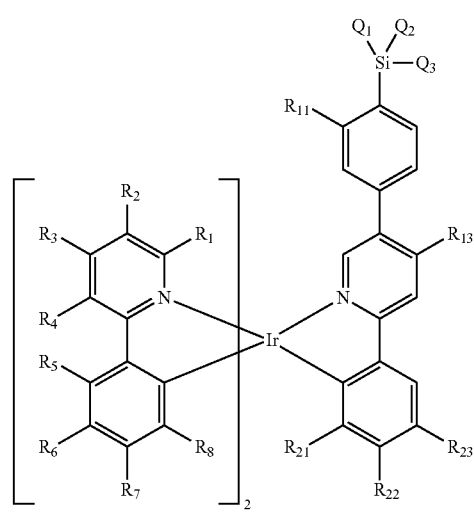
Formula 2-59
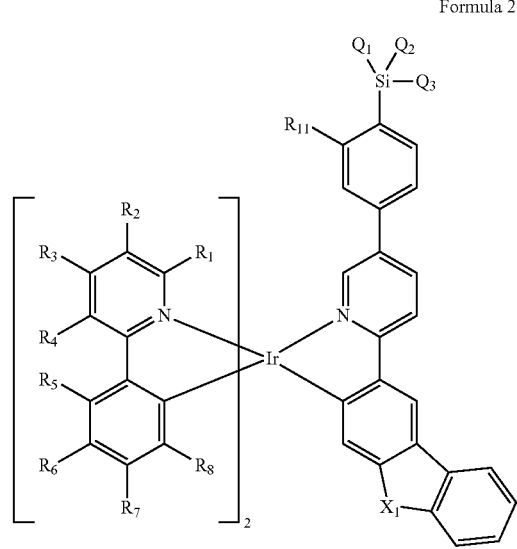

Formula 2-60
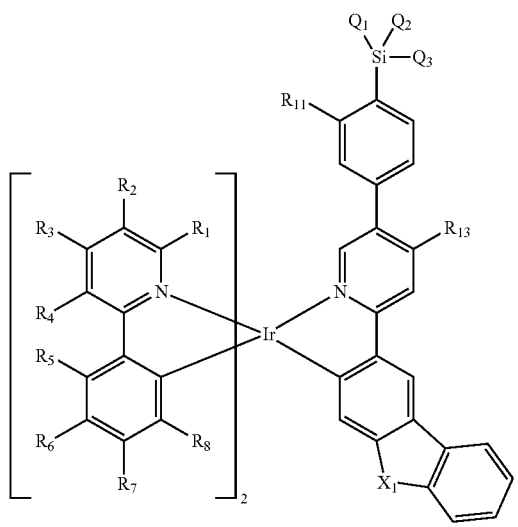
Formula 2-61
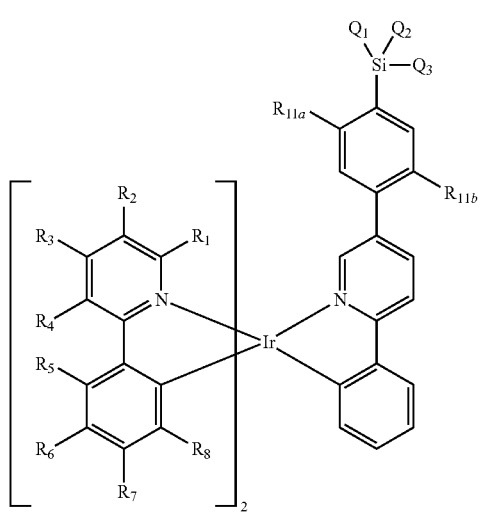
Formula 2-62
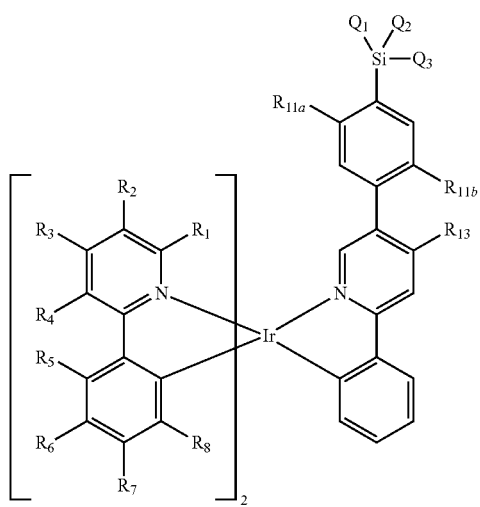
Formula 2-63
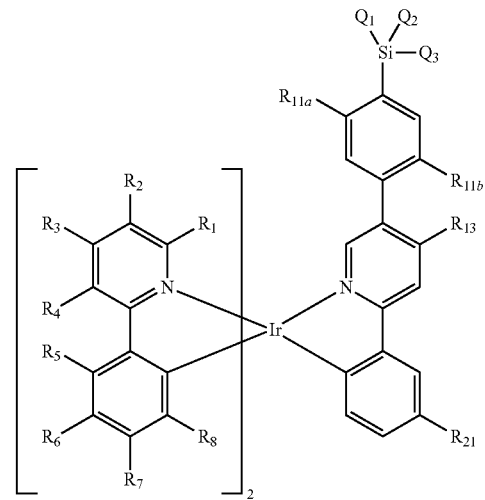
Formula 2-64
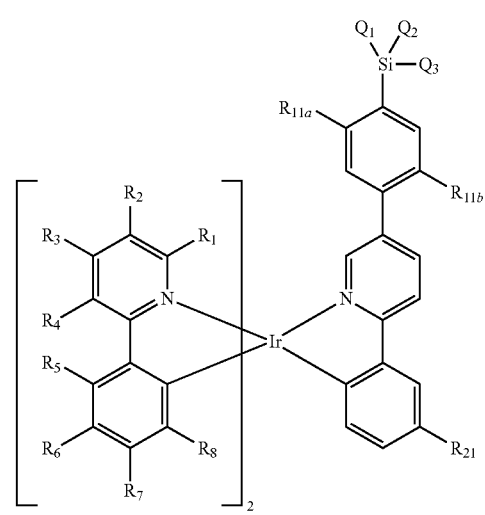
Formula 2-65
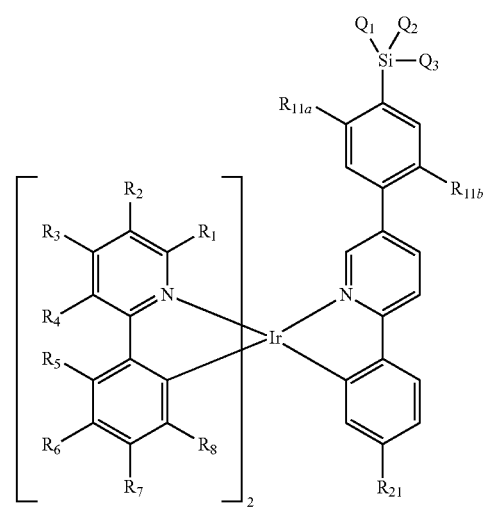

Formula 2-66
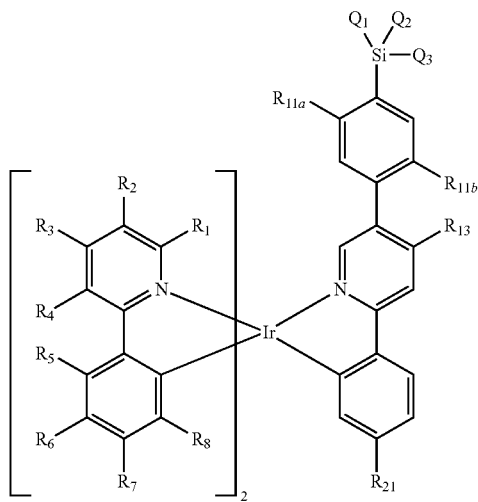
Formula 2-67
Formula 2-68
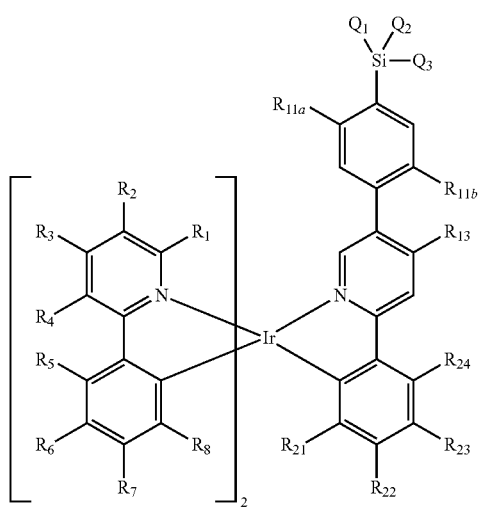
Formula 2-69
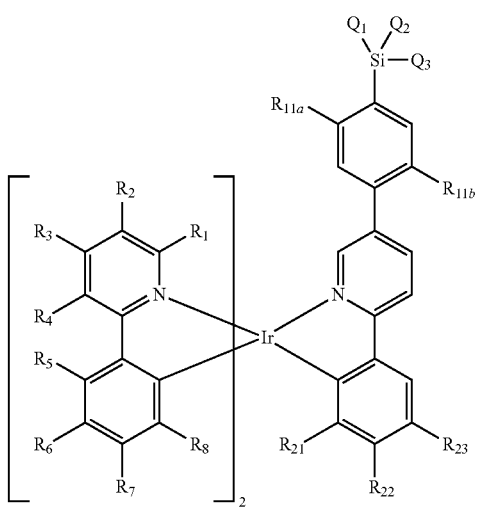
Formula 2-70
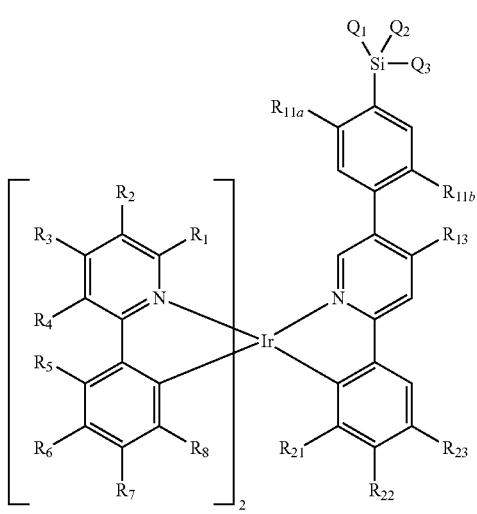
Formula 2-71
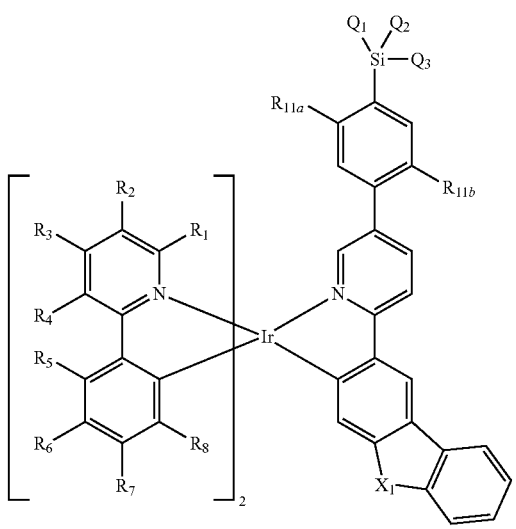

-continued

Formula 2-72

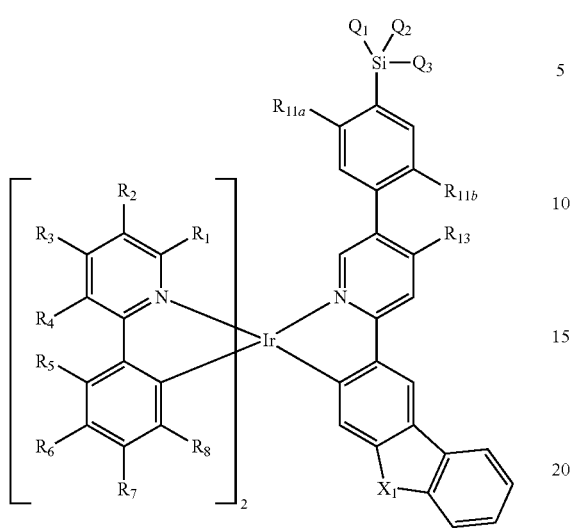

In connection with Formulae 2-1 to 2-72, descriptions of $Q_1$ to $Q_3$, $R_1$ to $R_8$, $R_{11}$, $R_{13}$, and $R_{21}$ are the same as described above, $X_1$ may be $N(R_{21})$, O, or S, descriptions of $R_{11a}$ and $R_{11b}$ are the same as descriptions of $R_{11}$, and descriptions of $R_{22}$ to $R_{24}$ are the same as descriptions of $R_{21}$. In this embodiment, however, $R_{11}$, $R_{11a}$, $R_{11b}$, $R_{13}$ and $R_{21}$ to $R_{24}$ in Formulae 2-1 to 2-72 are not a hydrogen.

For example, in Formulae 2-1 and 2-72, $Q_1$ to $Q_3$ may be each independently selected from
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group; and an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group, each substituted with at least one selected from a deuterium and a $C_1$-$C_{10}$ alkyl group, $R_1$ to $R_8$ may all be a hydrogen;

$R_1$, $R_2$, and $R_4$ to $R_8$ may be a hydrogen, and $R_3$ may be selected from a deuterium, —$CH_3$, —$CDH_2$, —$CD_2H$, and —$CD_3$;

$R_1$, $R_2$, $R_4$, $R_5$, $R_6$ and $R_8$ may be a hydrogen, and $R_3$ and $R_7$ may be each independently selected from a deuterium, —$CH_3$, —$CDH_2$, —$CD_2H$, and —$CD_3$;

$R_1$ to $R_4$ may be a hydrogen, and $R_5$ to $R_8$ may be each independently selected from a deuterium, —$CH_3$, —$CDH_2$, —$CD_2H$, and —$CD_3$;

$R_1$ to $R_5$ may be a hydrogen, and $R_6$ to $R_8$ may be each independently selected from a deuterium, —$CH_3$, —$CDH_2$, —$CD_2H$, and —$CD_3$;

$R_1$ to $R_4$ and $R_8$ may be a hydrogen, and $R_5$ to $R_7$ may be each independently selected from a deuterium, —$CH_3$, —$CDH_2$, —$CD_2H$, and —$CD_3$; or $R_1$ to $R_8$ may be each independently selected from a deuterium, —$CH_3$, —$CDH_2$, —$CD_2H$, and —$CD_3$, $R_{11}$, $R_{11a}$, $R_{11b}$, and $R_{13}$ may be each independently selected from a deuterium, —$CH_3$, —$CD_3$, —$CD_2H$, —$CDH_2$, a group represented by Formulae 9-1 to 9-17, and a group represented by Formulae 10-1 to 10-12, $R_{21}$ to $R_{24}$ may be each independently selected from a deuterium, a cyano group, a nitro group, —$CH_3$, —$CD_3$, —$CD_2H$, —$CDH_2$, —$CF_3$, —$CF_2H$, —$CFH_2$, a group represented by Formulae 9-1 to 9-17, and a group represented by Formulae 10-1 to 10-30.

In some embodiments, the organometallic compound represented by Formula 1 may be represented by one of Formulae 1 to 54 below:

1

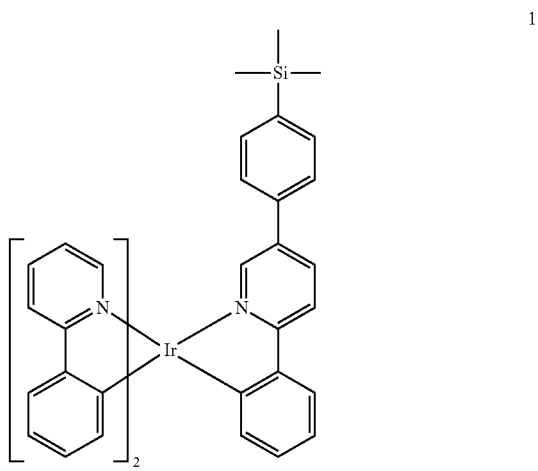

2

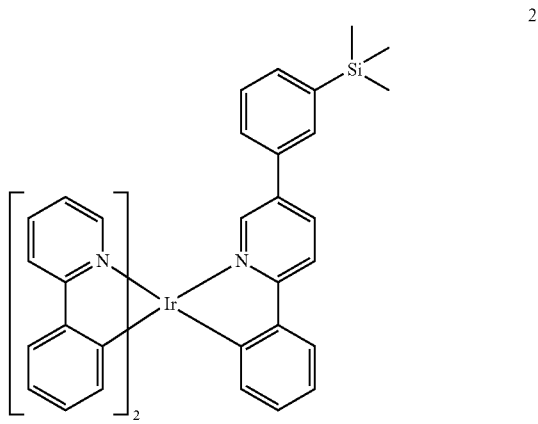

3

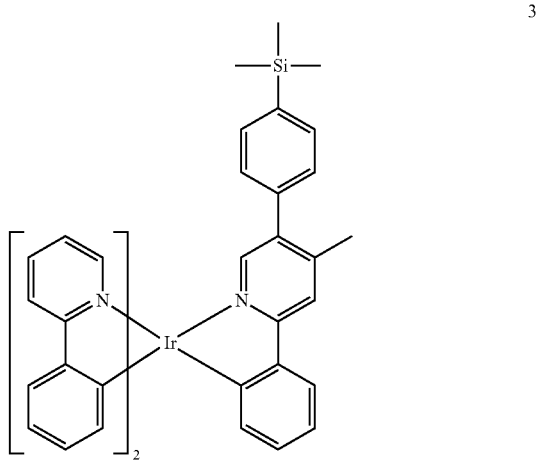

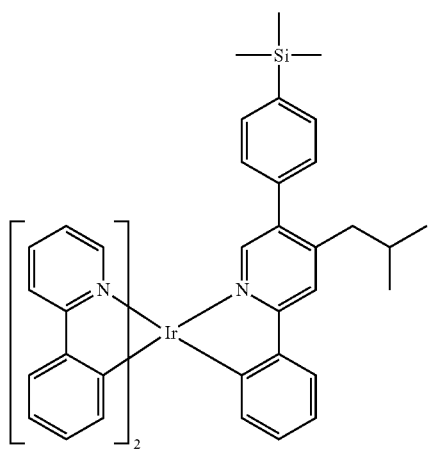
4
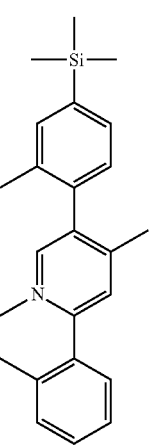
7
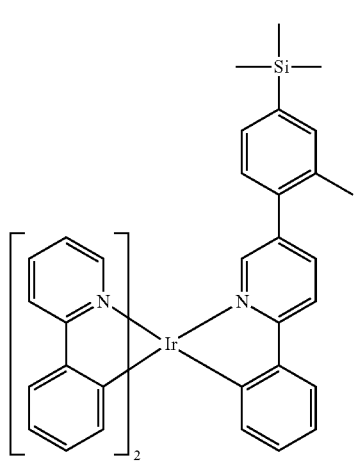
5
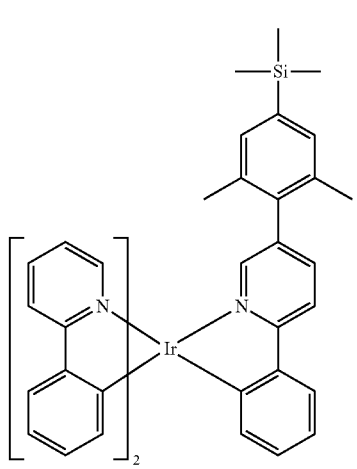
8
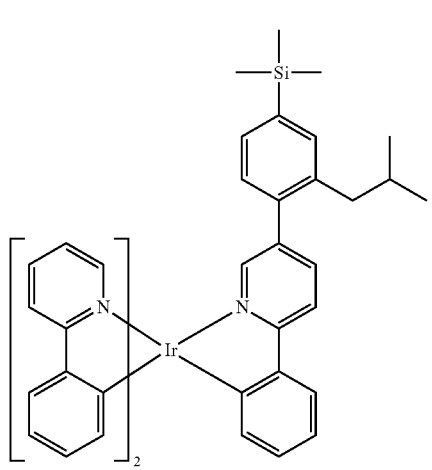
6
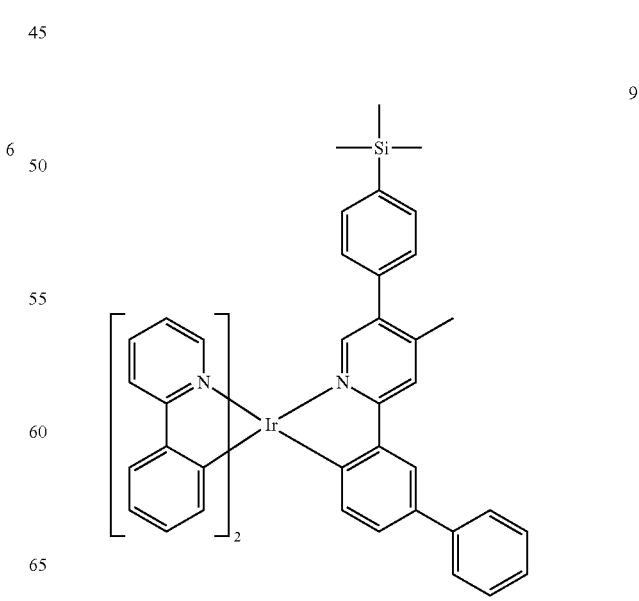
9

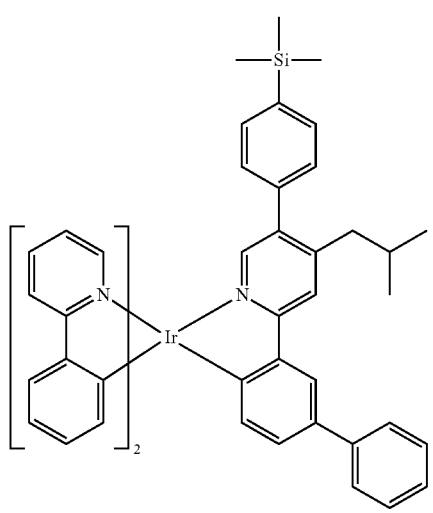
10
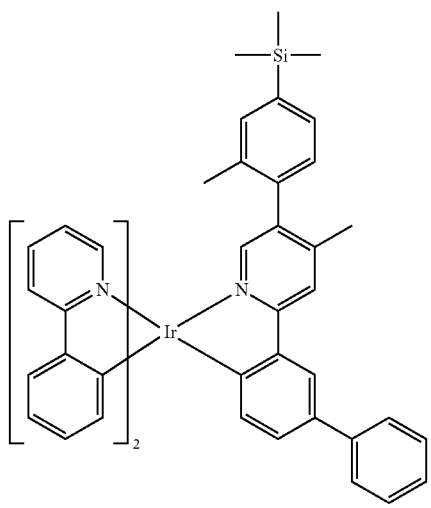
13
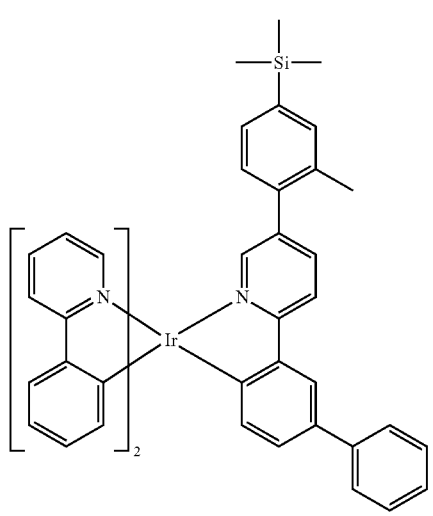
11
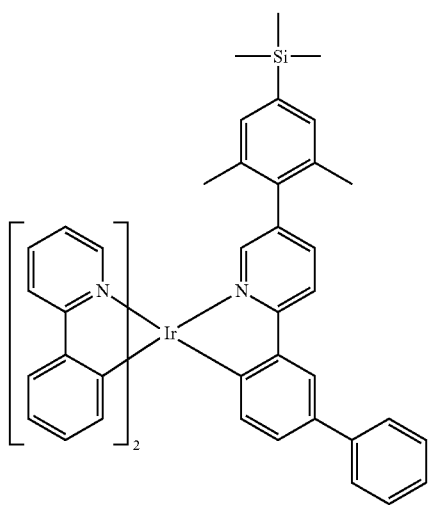
14
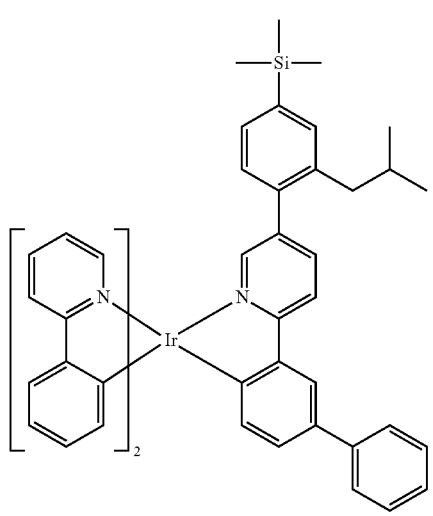
12
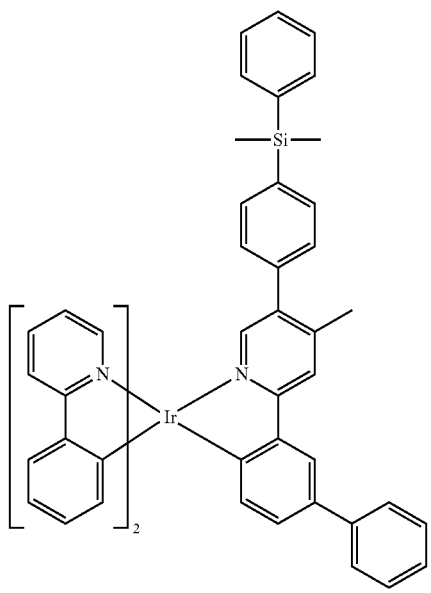
15

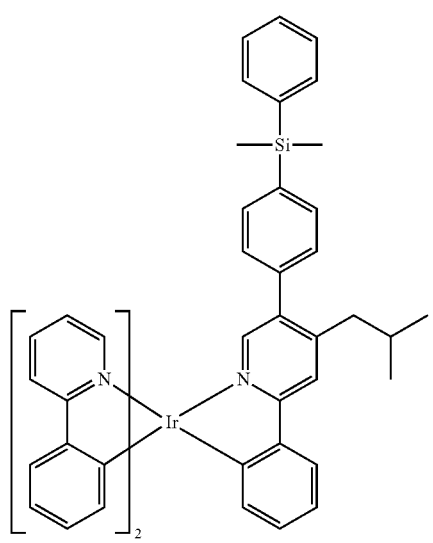
16
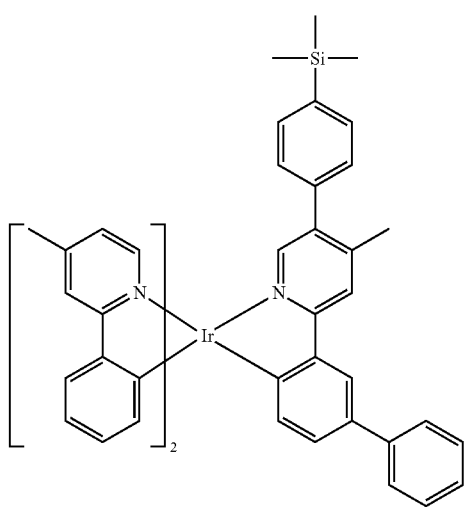
19
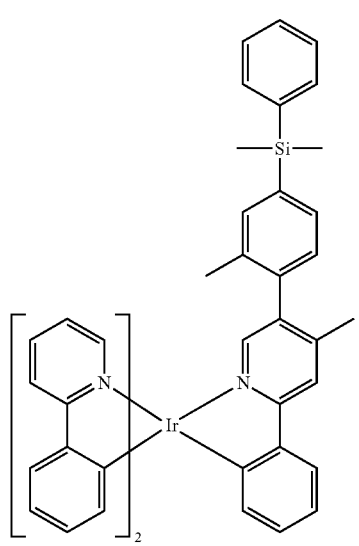
17
20
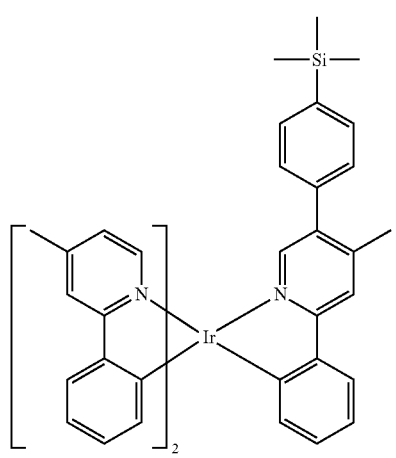
18
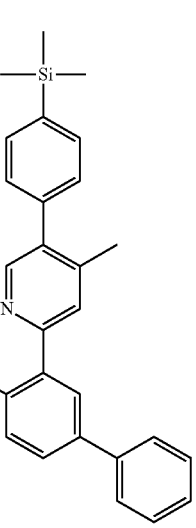
21

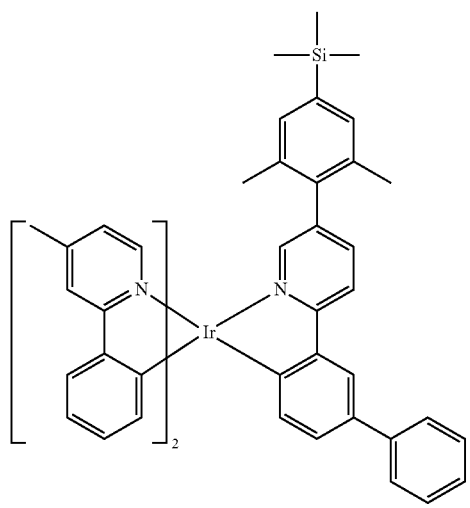
22
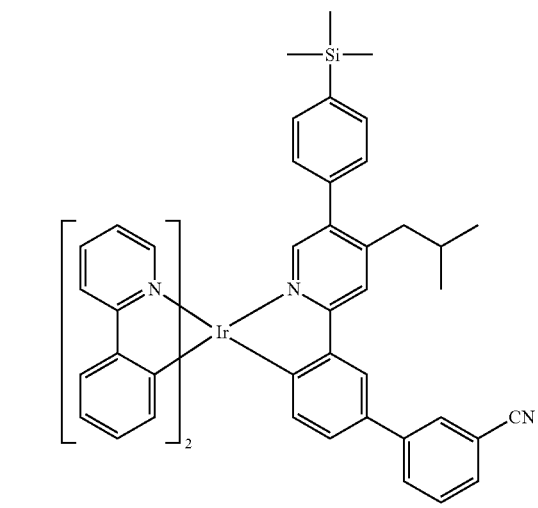
25
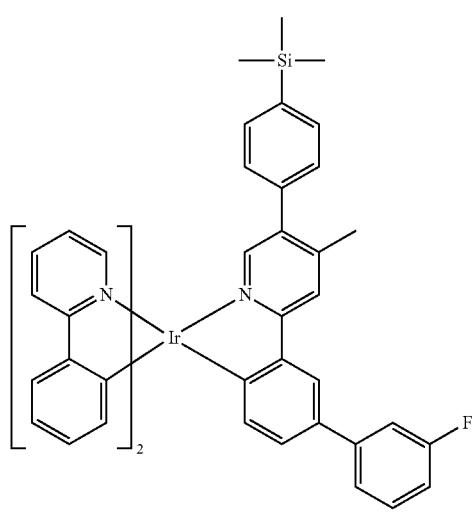
23
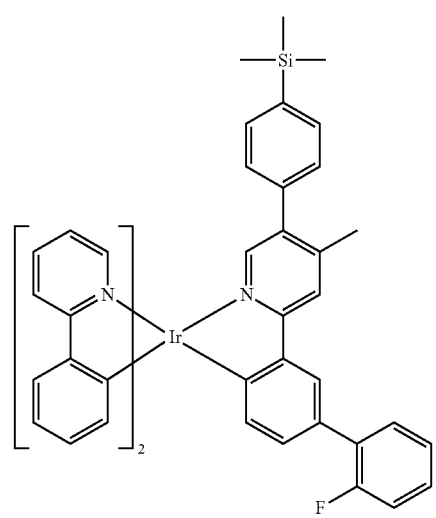
26
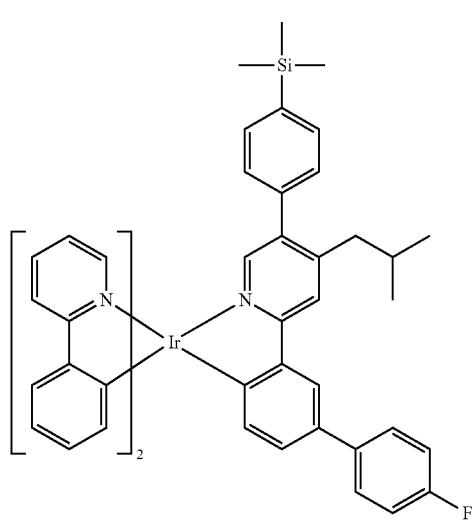
24
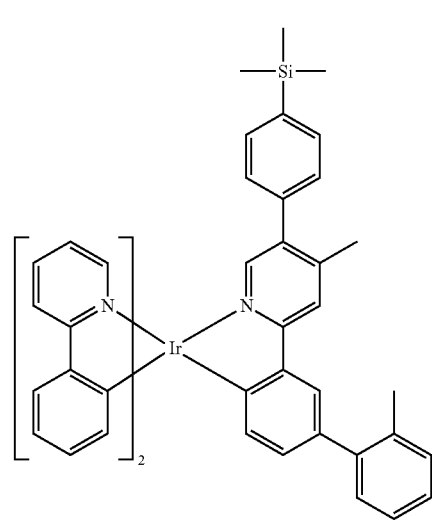
27

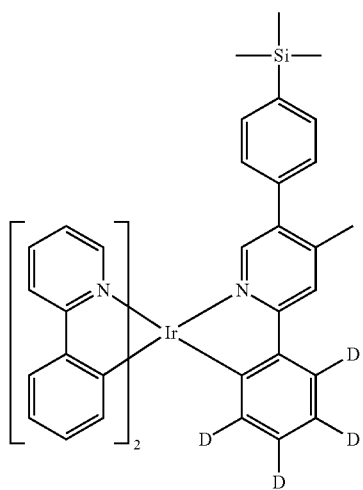
28
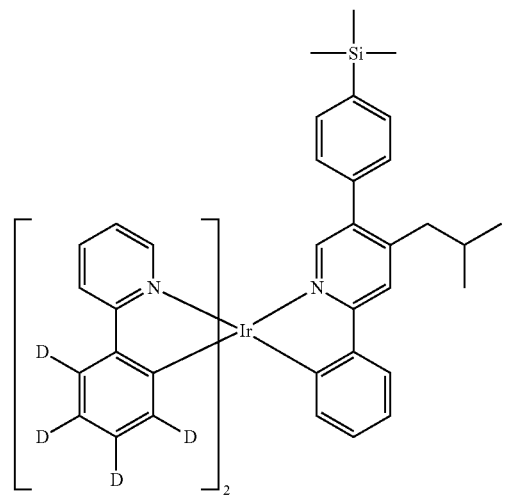
31
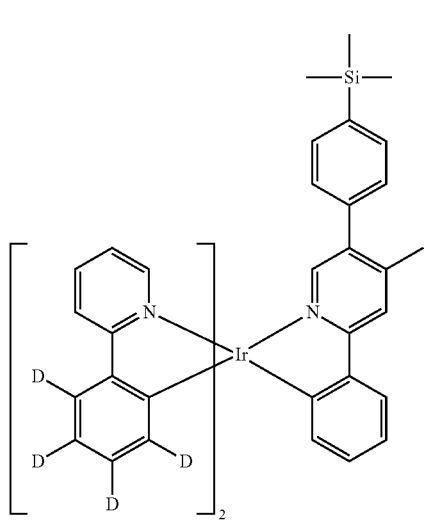
29
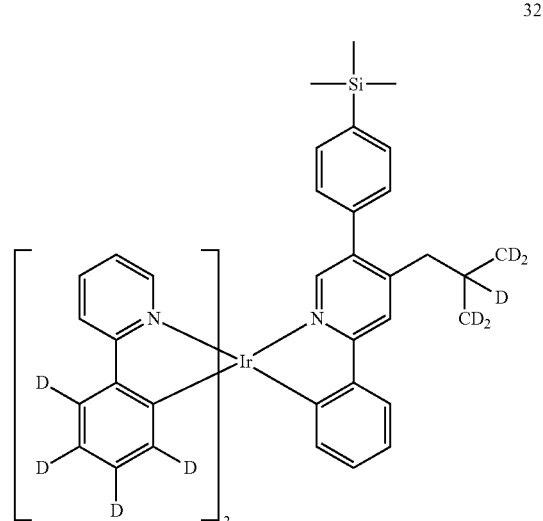
32
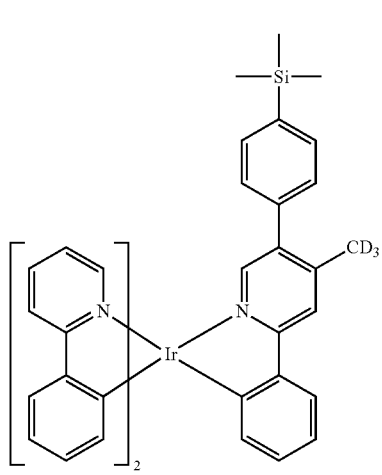
30
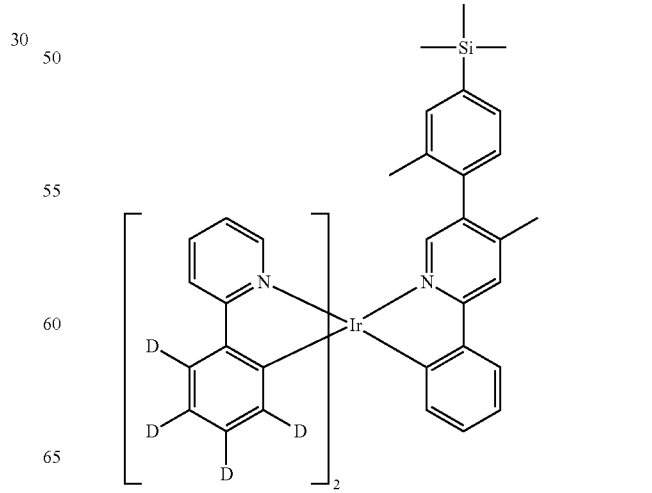
33

34
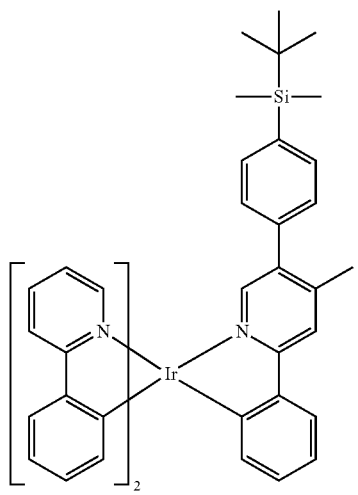
35
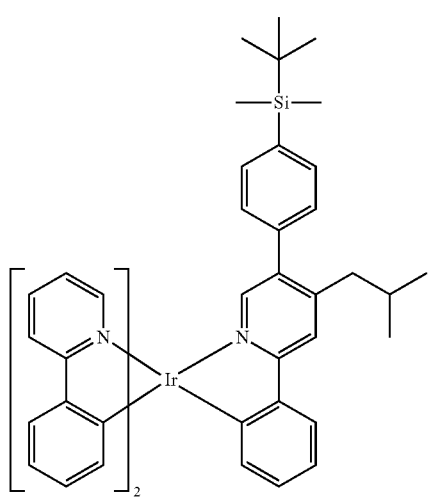
36
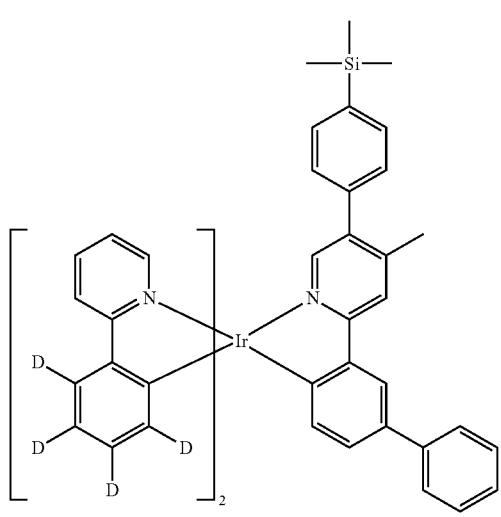
37
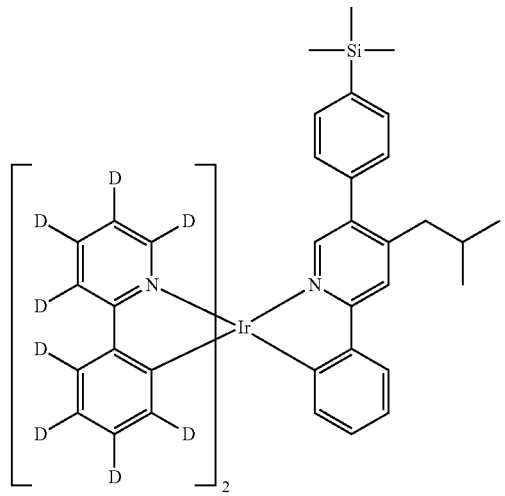
38
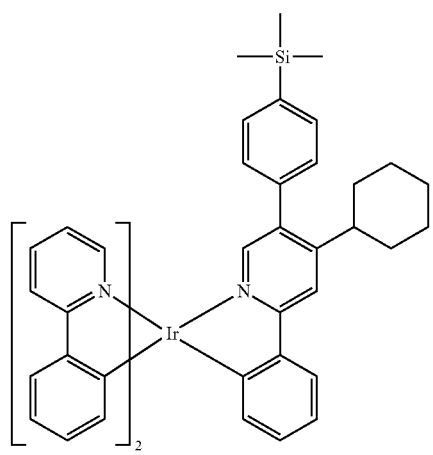
39
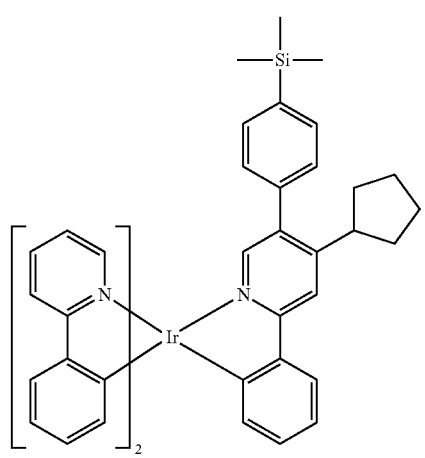

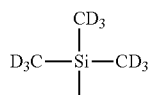
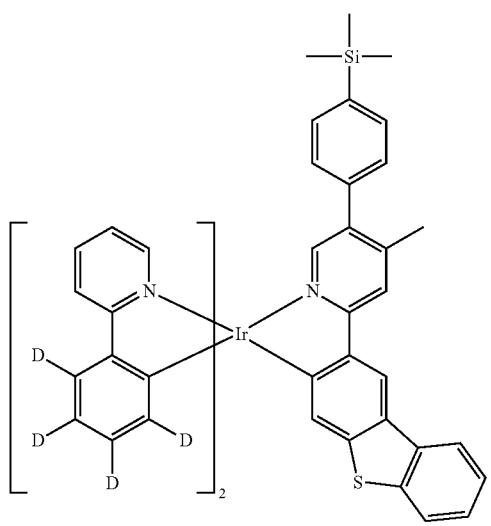
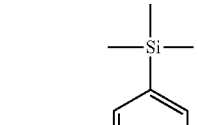
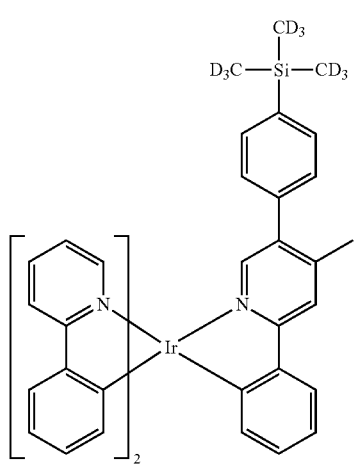
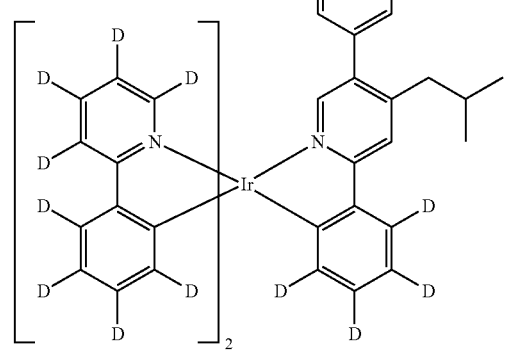
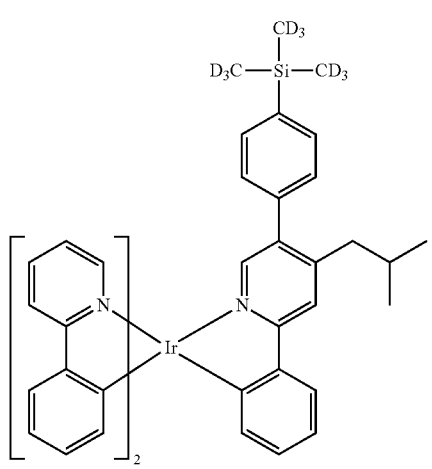
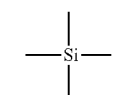
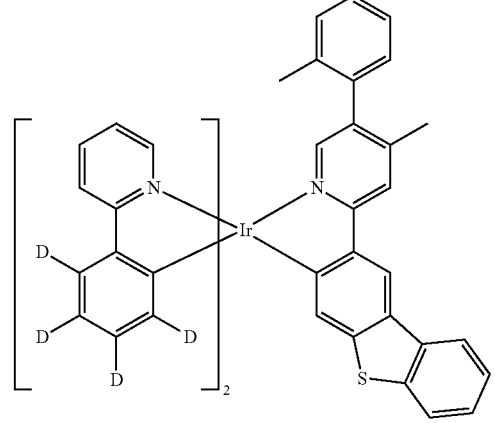

46
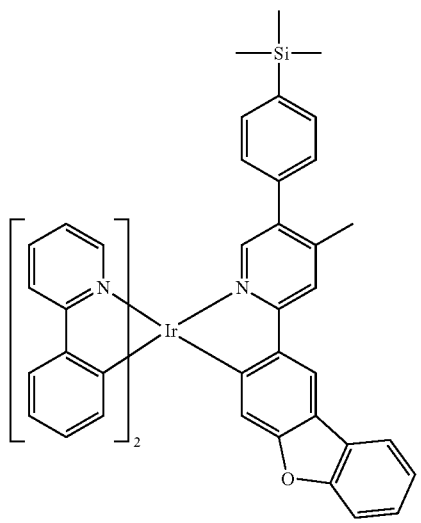
47
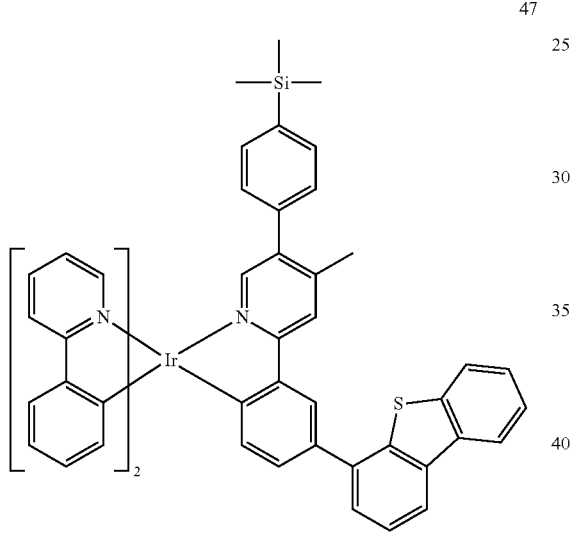
48
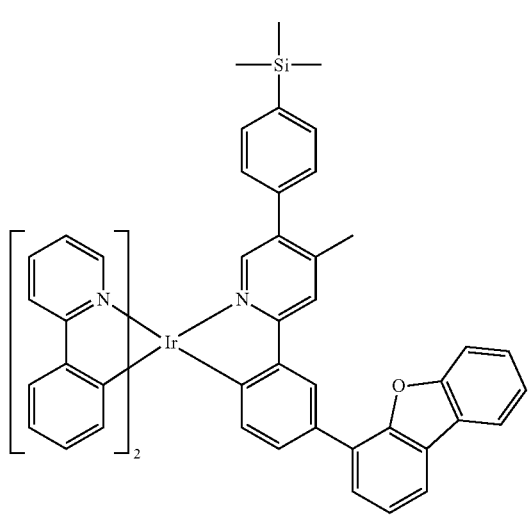
49
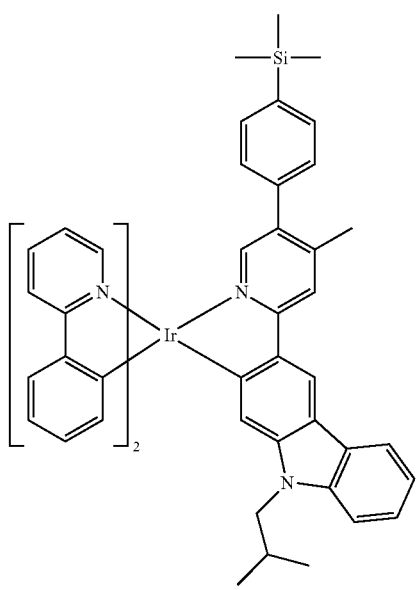
50
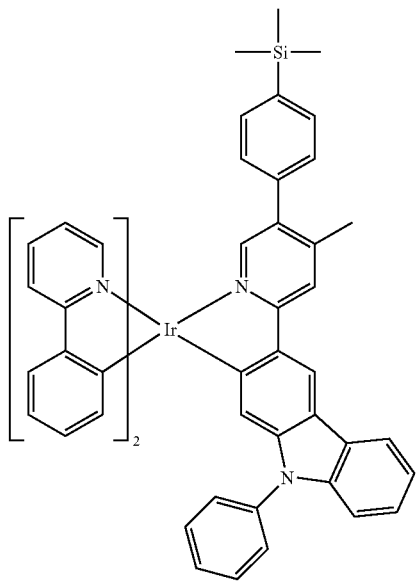

69
-continued

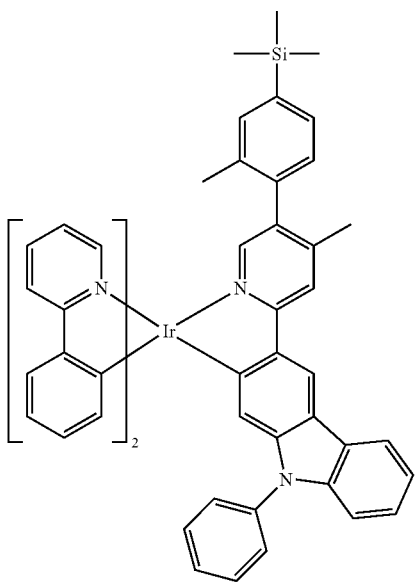

52

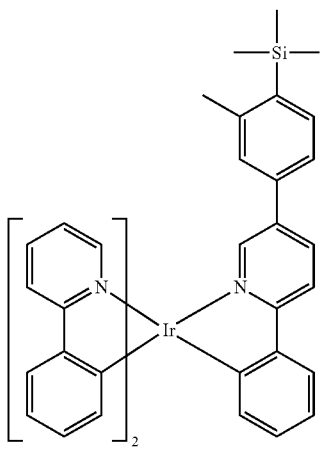

53

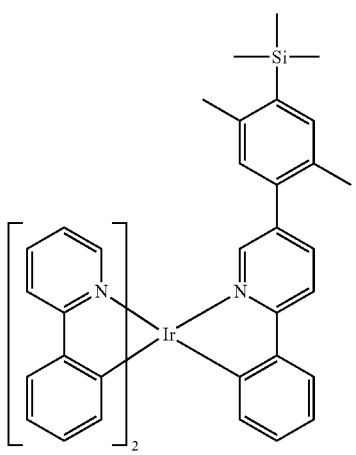

70
-continued

51

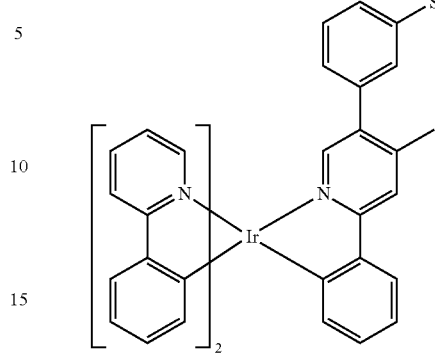

54

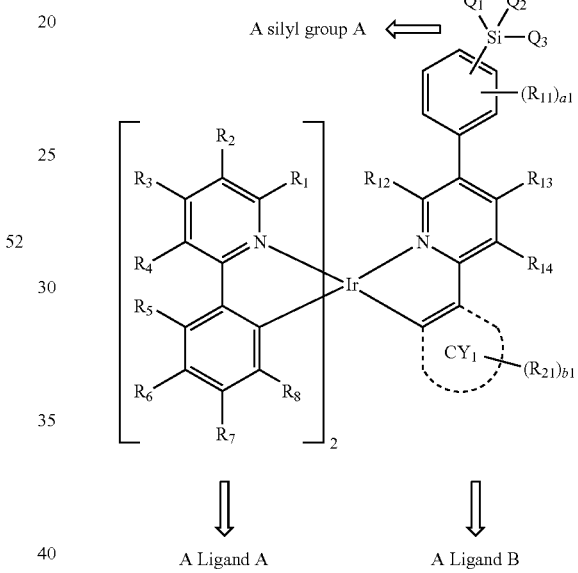

$R_1$ to $R_8$ of Ligand A in Formula 1 may be each independently selected from a hydrogen, a deuterium, —CH$_3$, —CDH$_2$, —CD$_2$H, and —CD$_3$. Ligand B in Formula 1 does not include other silyl groups than a "silyl group A." An organometallic compound represented by Formula 1 having two Ligands A and one Ligand B has excellent thermal stability and process stability. Accordingly, when the organometallic compound represented by Formula 1 is used, a high-quality organic light-emitting device may be manufactured in bulk quantities.

In an example, the highest occupied molecular orbital (HOMO), the lowest unoccupied molecular orbital (LUMO), and triplet ($T_1$) energy levels of Compounds 1 to 7 were evaluated by using a DFT method of Gaussian program (structurally optimized at a level of B3LYP, 6-31G (d,p)). The evaluation results are shown in Table 1 below.

TABLE 1

| Compound No. | HOMO (eV) | LUMO (eV) | $T_1$ energy level (eV) |
|---|---|---|---|
| 1 | −4.852 | −1.404 | 2.486 |
| 2 | −4.847 | −1.353 | 2.506 |

TABLE 1-continued

| Compound No. | HOMO (eV) | LUMO (eV) | T$_1$ energy level (eV) |
|---|---|---|---|
| 3 | −4.811 | −1.278 | 2.571 |
| 4 | −4.806 | −1.191 | 2.628 |
| 5 | −4.846 | −1.309 | 2.552 |
| 6 | −4.840 | −1.267 | 2.571 |
| 7 | −4.814 | −1.171 | 2.630 |

From Table 1, it is confirmed that the compound represented by Formula 1 has electric characteristics that are suitable for use as a material for manufacturing an electric device, for example, an organic light-emitting device.

Synthesis methods of the organometallic compounds represented by Formula 1 may be understood by one of ordinary skill in the art by referring to Synthesis Examples provided below.

The organometallic compound represented by Formula 1 is suitable for use in an organic layer of an organic light-emitting device, for example, for use as a dopant in an emission layer of the organic layer. Thus, another aspect provides an organic light-emitting device that includes:

a first electrode;

a second electrode; and an organic layer that is disposed between the first electrode and the second electrode, wherein the organic layer includes an emission layer and at least one organometallic compound represented by Formula 1.

The organic light-emitting device may have, due to the inclusion of an organic layer including the organometallic compound represented by Formula 1, a low driving voltage, high efficiency, high luminance, and a long lifespan.

The organometallic compound of Formula 1 may be used between a pair of electrodes of an organic light-emitting device. For example, the organometallic compound represented by Formula 1 may be included in the emission layer. In this regard, the organometallic compound may act as a dopant, and the emission layer may further include a host (that is, an amount of the organometallic compound represented by Formula 1 is smaller than an amount of the host).

The expression "(an organic layer) includes at least one organometallic compounds" as used herein may include an embodiment in which "(an organic layer) includes identical organometallic compounds of Formula 1 and an embodiment in which (an organic layer) includes two or more different organometallic compounds of Formula 1.

For example, the organic layer may include, as the organometallic compound, only Compound 1. In this regard, Compound 1 may be included in an emission layer of the organic light-emitting device. In some embodiments, the organic layer may include, as the organometallic compound, Compound 1 and Compound 2. In this regard, Compound 1 and Compound 2 may be included in an identical layer (for example, Compound 1 and Compound 2 all may exist in an emission layer).

The first electrode may be an anode, which is a hole injection electrode, and the second electrode may be a cathode, which is an electron injection electrode; or the first electrode may be a cathode, which is an electron injection electrode, or the second electrode may be an anode, which is a hole injection electrode.

For example, the first electrode may be an anode, and the second electrode may be a cathode, and the organic layer includes:

i) a hole transport region that is disposed between the first electrode and the emission layer, wherein the hole transport region includes at least one selected from a hole injection layer, a hole transport layer, and an electron blocking layer, and ii) an electron transport region that is disposed between the emission layer and the second electrode, wherein the electron transport region includes at least one selected from a hole blocking layer, an electron transport layer, and an electron injection layer.

The term "organic layer" as used herein refers to a single layer and/or a plurality of layers disposed between the first electrode and the second electrode of an organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

In FIG. 1, a substrate may be additionally disposed under the first electrode 11 or above the second electrode 19. As the substrate, any substrate that is used in general organic light-emitting devices may be used. The substrate may be a glass substrate or transparent plastic substrate, each with excellent mechanical strength, thermal stability, transparency, surface smoothness, ease of handling, and water-resistance.

The first electrode 11 may be formed by depositing or sputtering a material for forming the first electrode on the substrate. The first electrode 11 may be an anode. The material for the first electrode 11 may be selected from materials with a high work function to readily provide holes. The first electrode 11 may be a reflective electrode or a transmissive electrode. The material for the first electrode may be, for example, indium tin oxide (ITO), indium zinc oxide (IZO), tin oxide ($SnO_2$), and zinc oxide (ZnO). In some embodiments, magnesium (Mg), aluminum (Al), aluminum-lithium (Al—Li), calcium (Ca), magnesium-indium (Mg—In), or magnesium-silver (Mg—Ag) may be used as the material for the first electrode.

The first electrode 11 may have a single-layer structure or a multi-layer structure including two or more layers. For example, the first electrode 11 may have a three-layered structure of ITO/Ag/ITO, but the structure of the first electrode 110 is not limited thereto.

An organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In some embodiments, the hole transport region may have a structure of hole injection layer/hole transport layer or hole injection layer/hole transport layer/electron blocking layer, which are sequentially stacked in this stated order from the first electrode 11.

A hole injection layer hole injection layer may be formed on the first electrode 11 by using various methods, such as vacuum deposition, spin coating, casting, or Langmuir-Blodgett (LB).

When a hole injection layer is formed by vacuum deposition, the deposition conditions may vary depending on a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (Å/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (PANI/CSA), (polyaniline)/poly(4-styrenesulfonate) (Pani/PSS), a compound represented by Formula 201 below, and a compound represented by Formula 202 below:

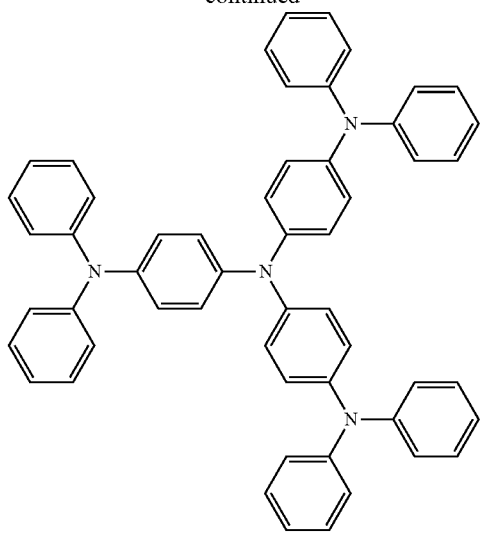

TDATA

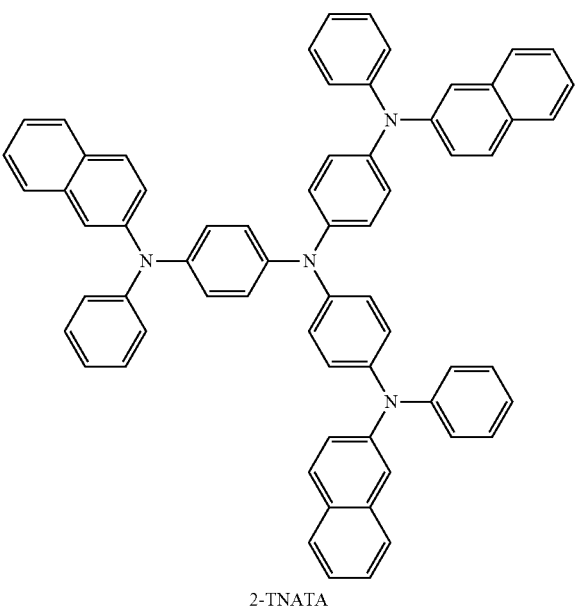

2-TNATA

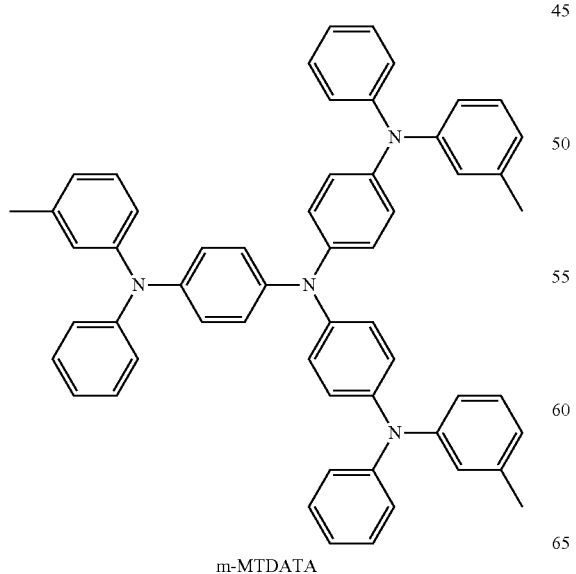

m-MTDATA

NPB

-continued

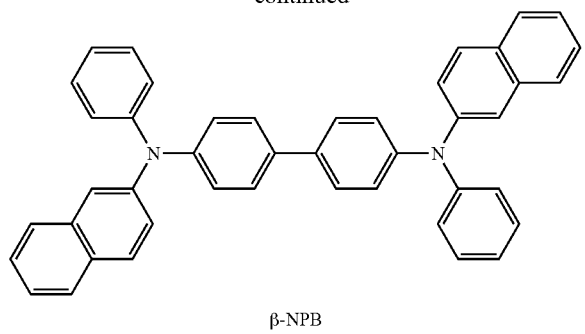

β-NPB

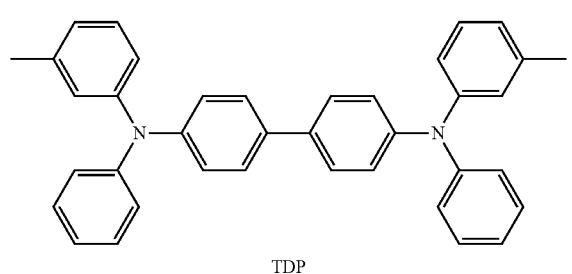

TDP

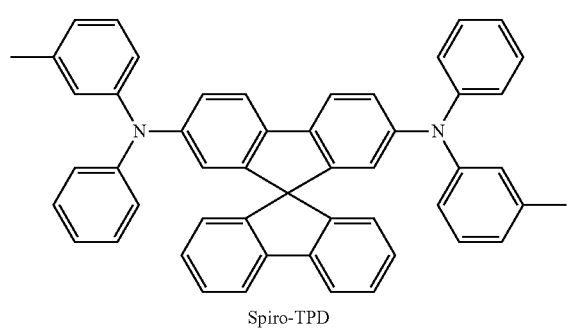

Spiro-TPD

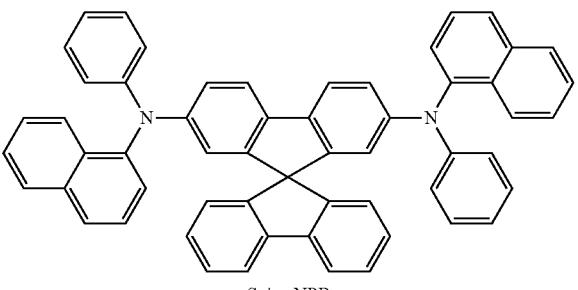

Spiro-NPB

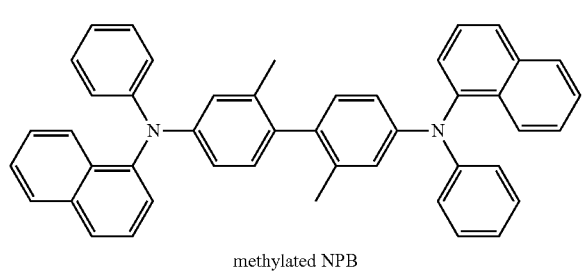

methylated NPB

-continued

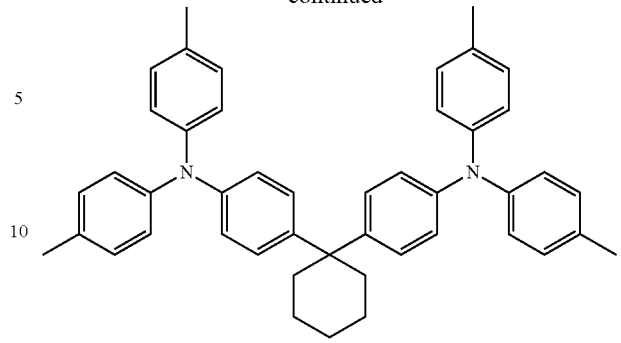

TAPC

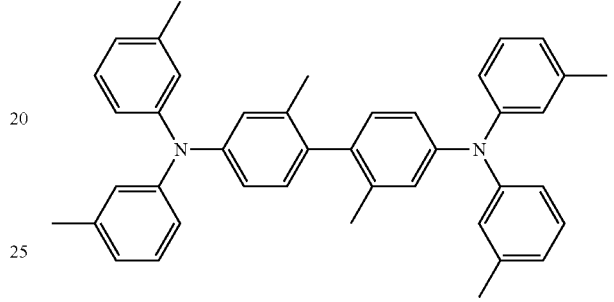

HMTPD

Formula 201

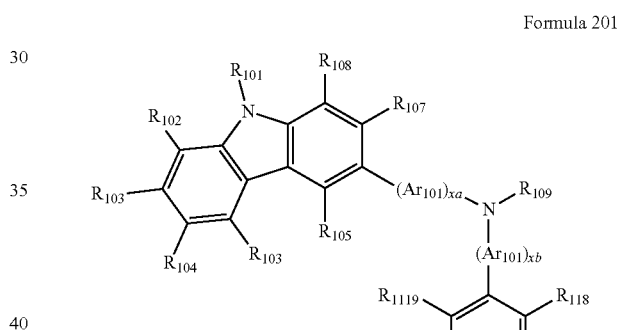

Formula 202

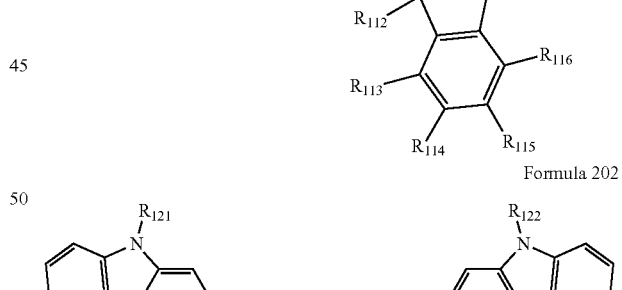

$Ar_{101}$ and $Ar_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may be each independently an integer selected from 0 to 5, for example, an integer selected from 0, 1, and 2. For example, xa is 1 and xb is 0, but xa and xb are not limited thereto.

$R_{101}$ to $R_{108}$, $R_{111}$ to $R_{119}$ and $R_{121}$ to $R_{124}$ in Formulae 201 and 202 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), and a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

$R_{109}$ in Formula 201 may be selected from a phenyl group, a naphthyl group, an anthracenyl group and a pyridinyl group; and a phenyl group, a naphthyl group, an anthracenyl group and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A, but is not limited thereto:

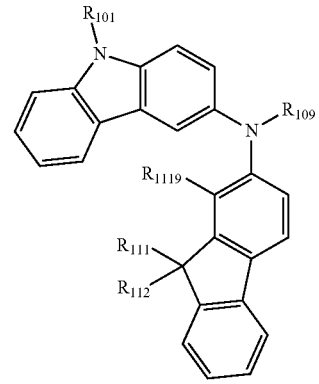

Formula 201A $R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto.

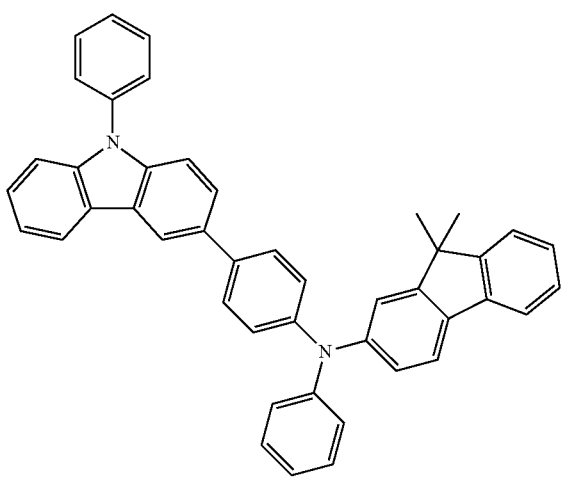

HT1

HT2
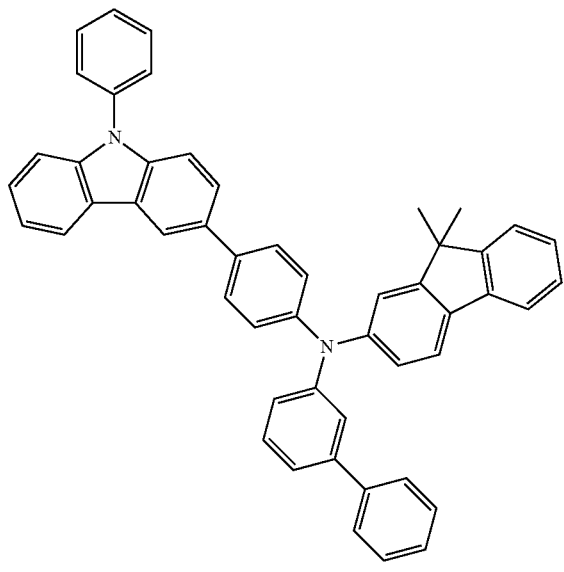
HT3
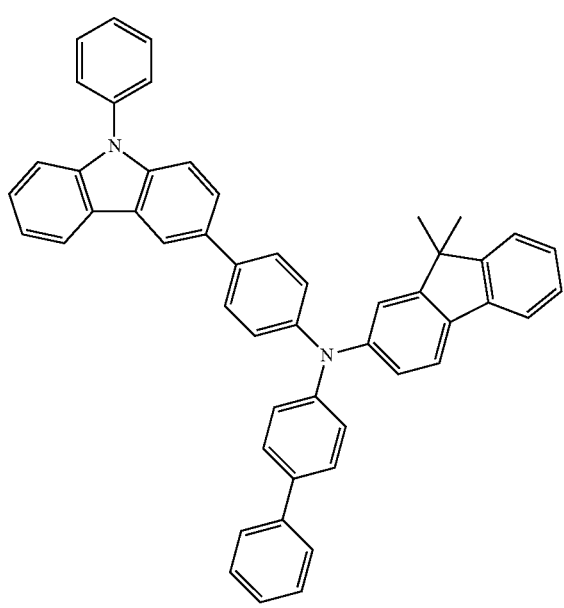
HT4
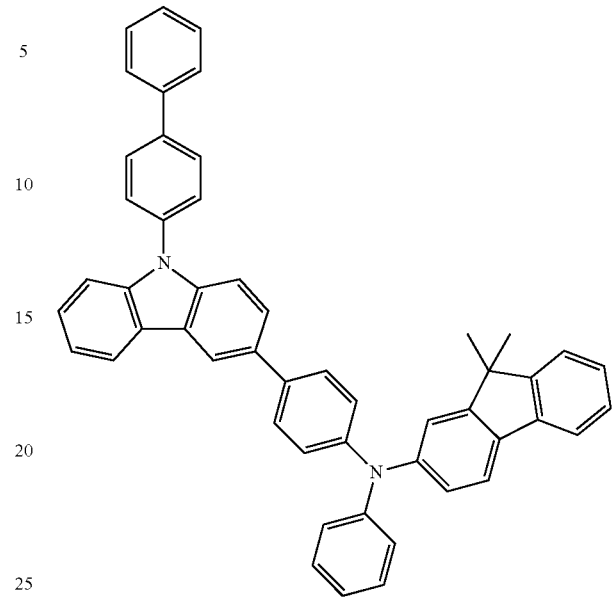
HT5
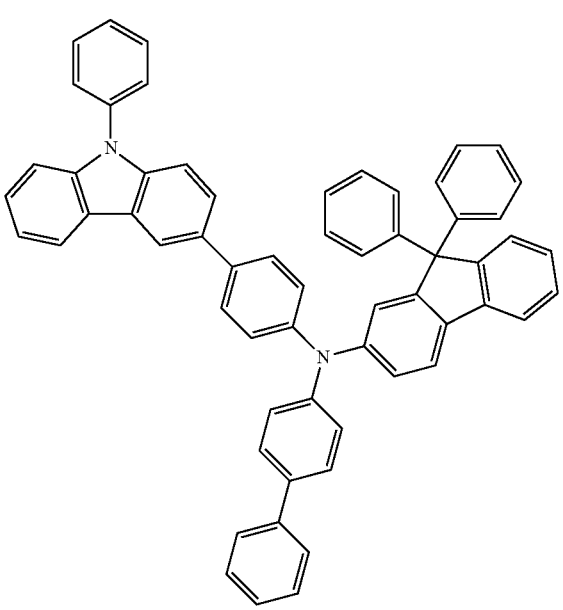

HT6
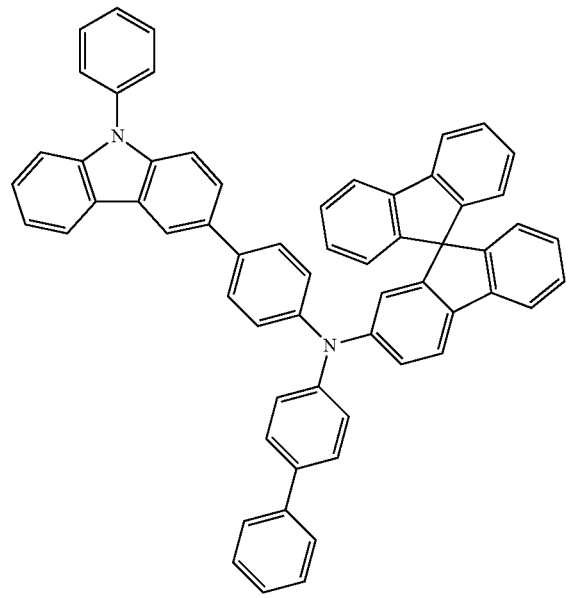
HT8
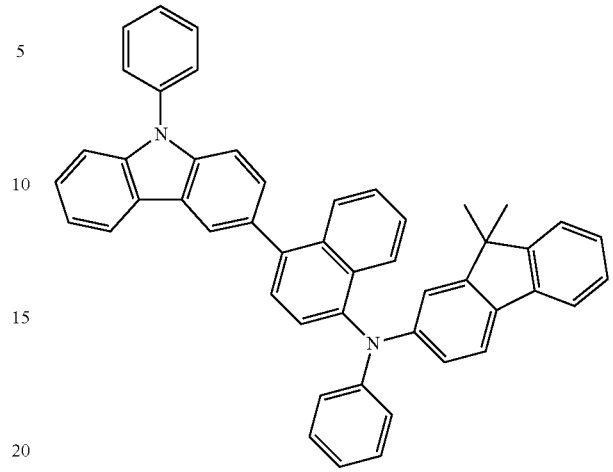
HT9
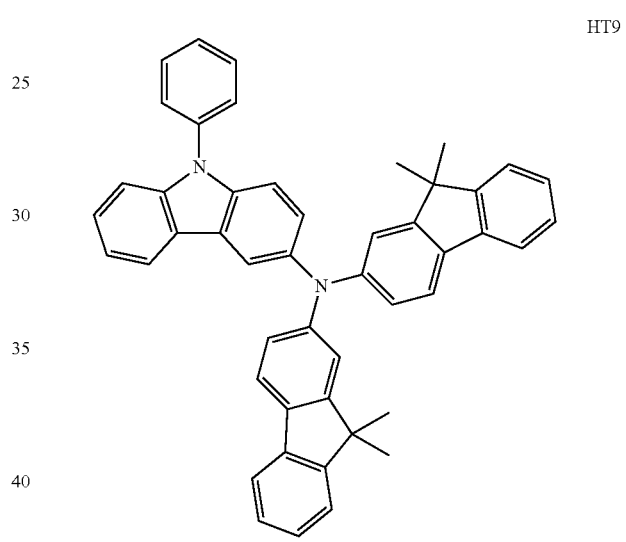
HT7
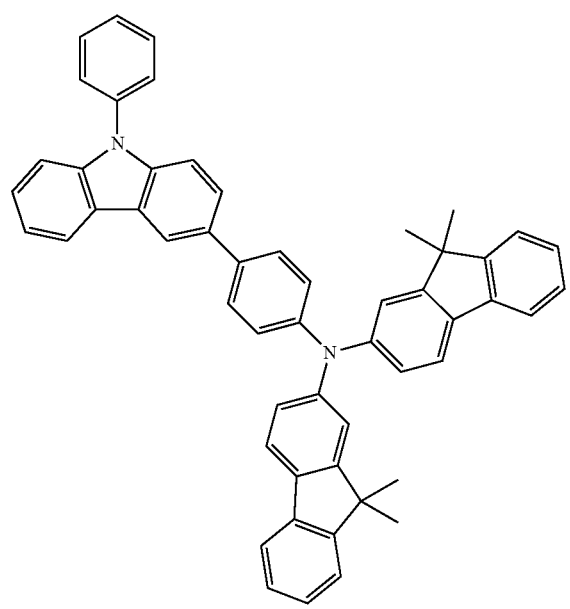
HT10
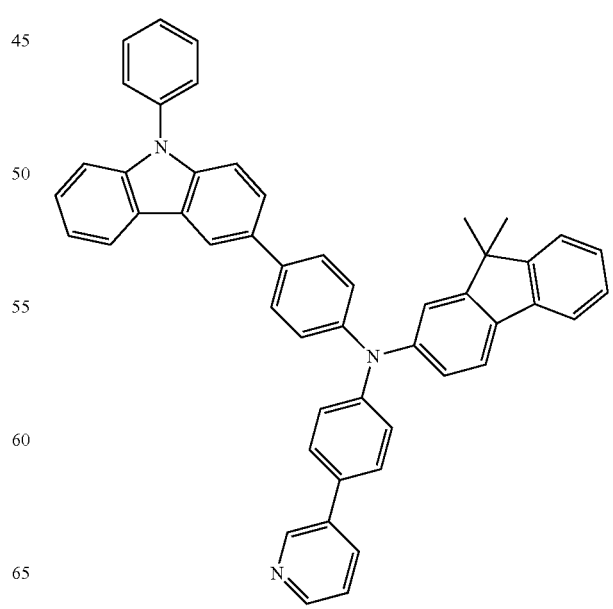

HT11
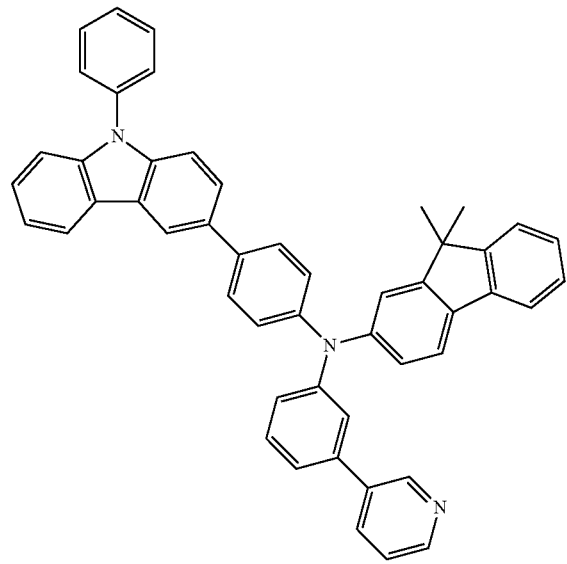
HT14
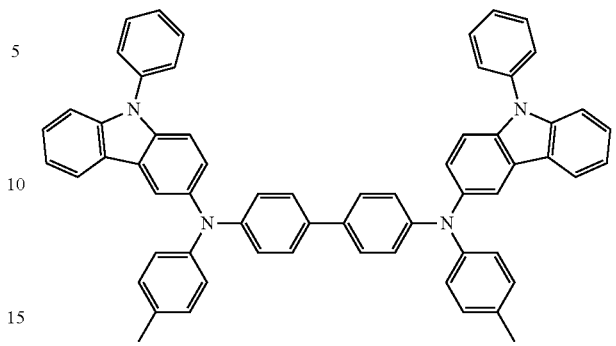
HT15
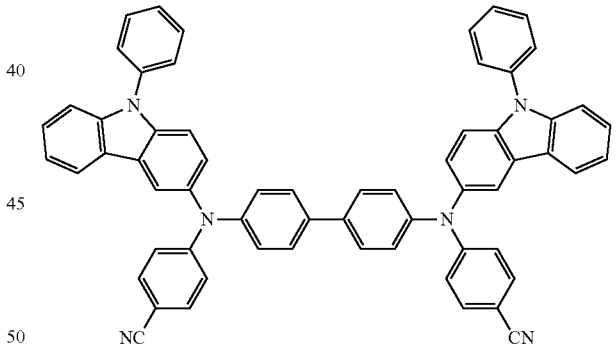
HT12
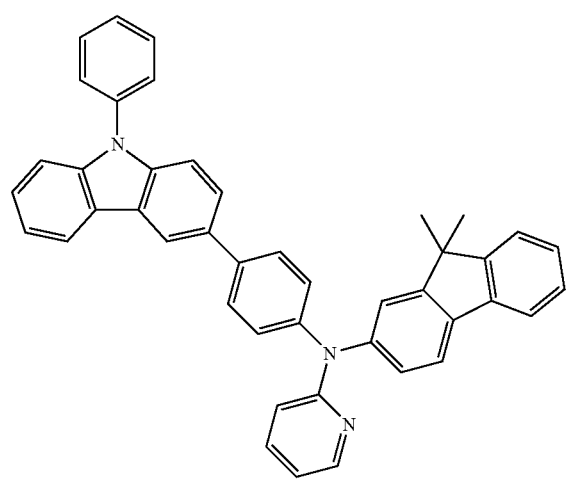
HT16
HT13
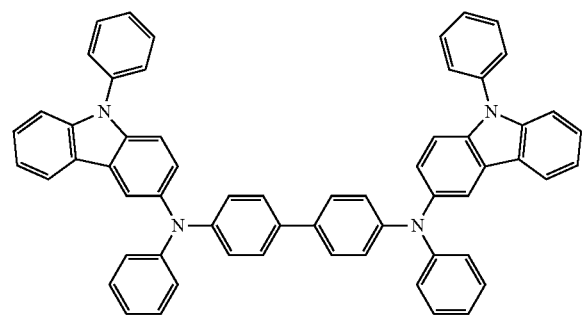
HT17
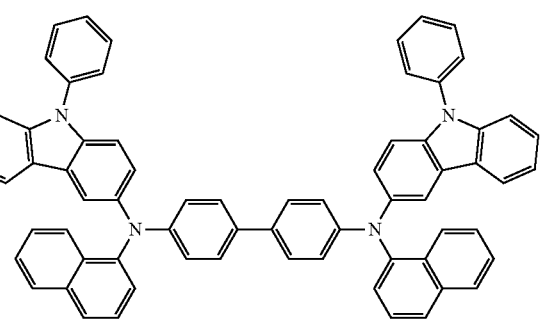

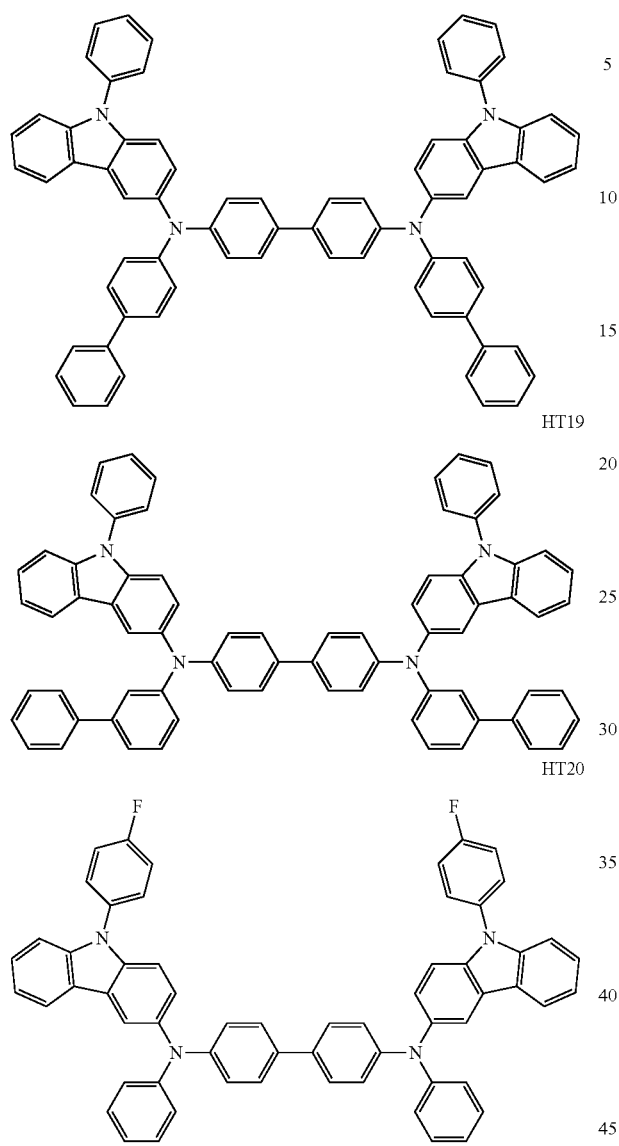

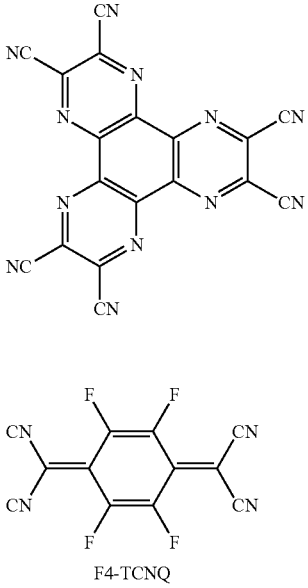

Compound HT-D1

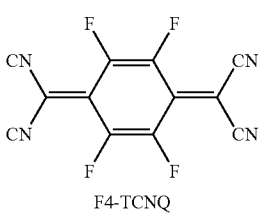

F4-TCNQ derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 below, but are not limited thereto.

A thickness of the hole transport region may be in a range of about 100 Angstroms (Å) to about 10,000 Å, for example, about 100 Å to about 1,000 Å. When the hole transport region includes a hole injection layer and a hole transport layer, the thickness of the hole injection layer may be in a range of about 100 Å to about 10,000 Å, for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone The hole transport region may include a buffer layer.

The buffer layer may compensate for an optical resonance distance depending on a wavelength of light emitted from the emission layer, thus improving the efficiency of a formed organic light-emitting device.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer. However, the deposition or coating conditions may vary according to the material that is used to form the emission layer.

Meanwhile, when the hole transport region includes an electron blocking layer, a material for the electron blocking layer may be selected from materials for the hole transport region described above and materials for a host, that will be discussed later. However, the material for the electron blocking layer is not limited thereto. For example, when the hole transport region includes an electron blocking layer, a material for the electron blocking layer may be mCP, which will also be discussed later.

The emission layer may include a host and a dopant, and the dopant may include the organometallic compound represented by Formula 1.

The host may include at least one selected form TPBi, TBADN, ADN (also referred to as "DNA"), CBP, CDBP, TCP, Mcp, Compound HSO, and Compound H51:

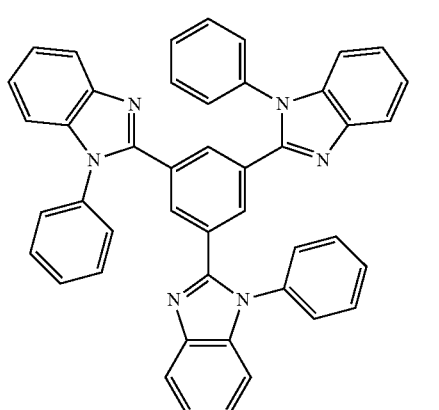
TPBi
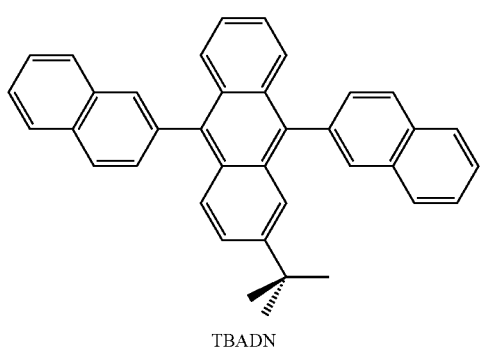
TBADN
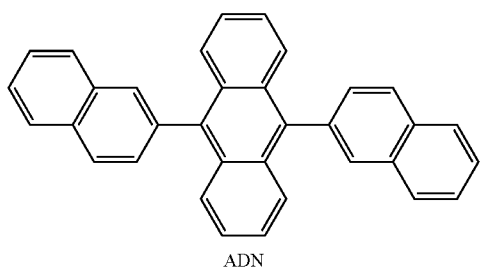
ADN
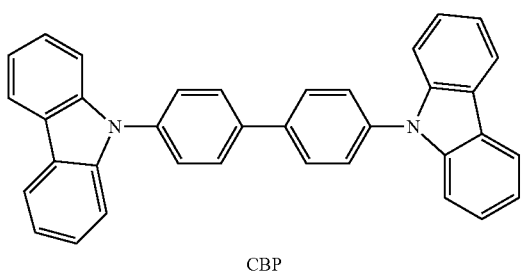
CBP
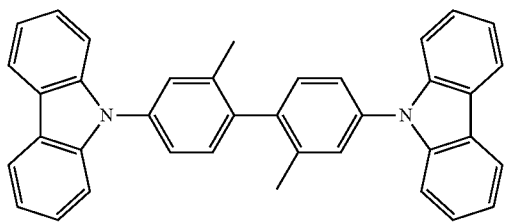
CDBP
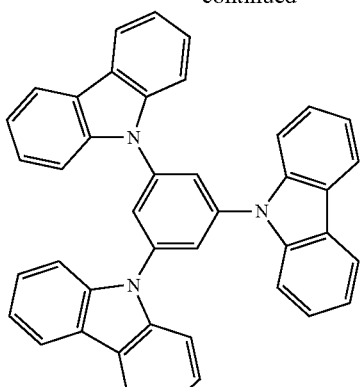
TCP
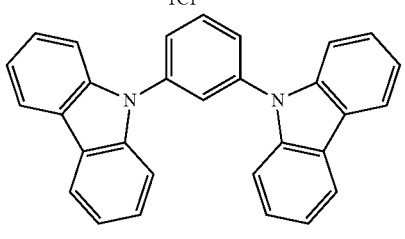
mCP
Compound H50
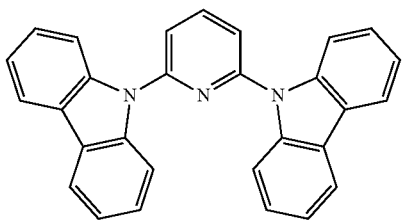
Compound H51
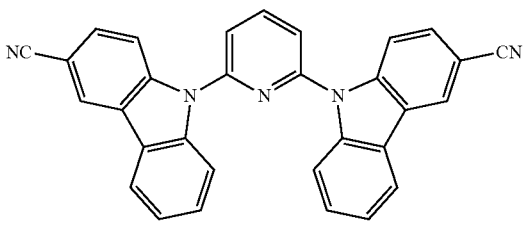
In some embodiments, the host may further include a compound represented by Formula 301 below.
Formula 301
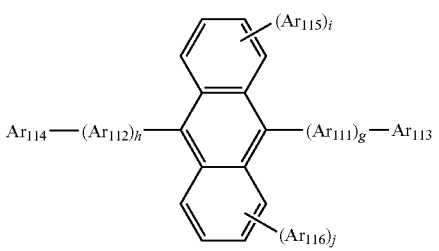
$Ar_{111}$ and $Ar_{112}$ in Formula 301 may be each independently selected from a phenylene group, a naphthylene group, a phenanthrenylene group, and a pyrenylene group; and a phenylene group, a naphthylene group, a phenanthrenylene group, and a pyrenylene group, each substituted with at least one selected from a phenyl group, a naphthyl group, and an anthracenyl group.

$Ar_{113}$ to $Ar_{116}$ in Formula 301 may be each independently selected from a $C_1$-$C_{10}$ alkyl group, a phenyl group, a naphthyl group, a phenanthrenyl group, and a pyrenyl group; and a phenyl group, a naphthyl group, a phenanthrenyl group, and a pyrenyl group, each substituted with at least one selected from a phenyl group, a naphthyl group, and an anthracenyl group.

g, h, I, and j in Formula 301 may be each independently an integer selected from 0 to 4, for example, an integer selected from 0, 1, and 2.

$Ar_{113}$ to $Ar_{116}$ in Formula 301 may be each independently selected from a $C_1$-$C_{10}$ alkyl group substituted with at least one selected from a phenyl group, a naphthyl group, and an anthracenyl group;

a phenyl group, a naphthyl group, an anthracenyl group, a pyrenyl, a phenanthrenyl group, and a fluorenyl group;

a phenyl group, a naphthyl group, an anthracenyl group, a pyrenyl group, a phenanthrenyl group, and a fluorenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

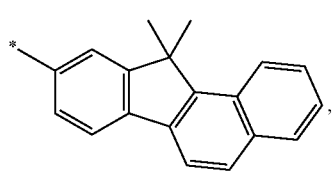 [SMILES: Cc1ccc2c(c1)C(C)(C)c1c-2ccc2ccccc12]

but embodiments are not limited thereto.

In some embodiments, the host may include a compound represented by Formula 302 below:

Formula 302

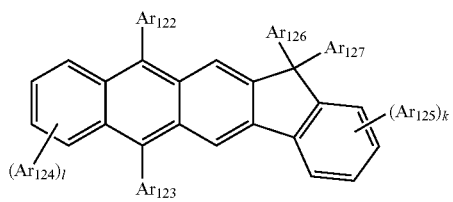

$Ar_{122}$ to $Ar_{125}$ in Formula 302 are the same as described in detail in connection with $Ar_{113}$ in Formula 301.

$Ar_{126}$ and $Ar_{127}$ in Formula 302 may be each independently a $C_1$-$C_{10}$ alkyl group (for example, a methyl group, an ethyl group, or a propyl group).

k and l in Formula 302 may be each independently an integer selected from 0 to 4. For example, k and l may be 0, 1, or 2.

The compound represented by Formula 301 and the compound represented by Formula 302 may include Compounds H1 to H42 illustrated below, but are not limited thereto.

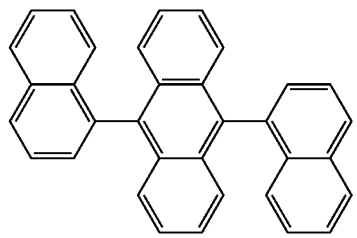

H1

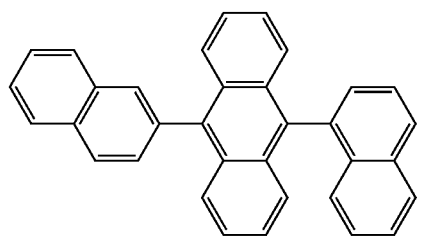

H2

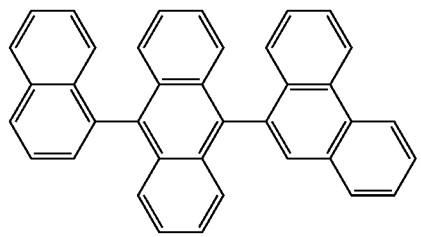

H3

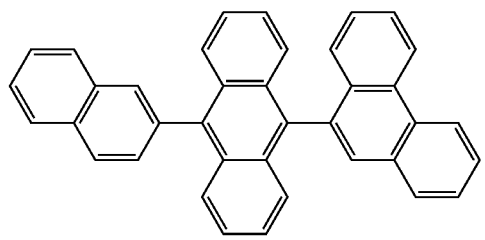

H4

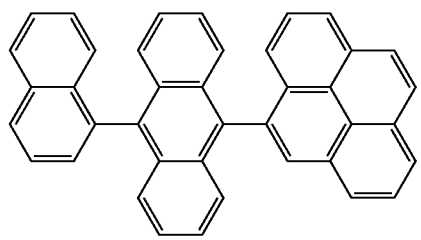

H5

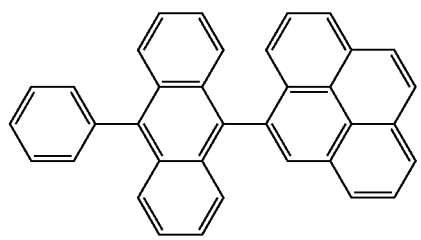

H6

-continued
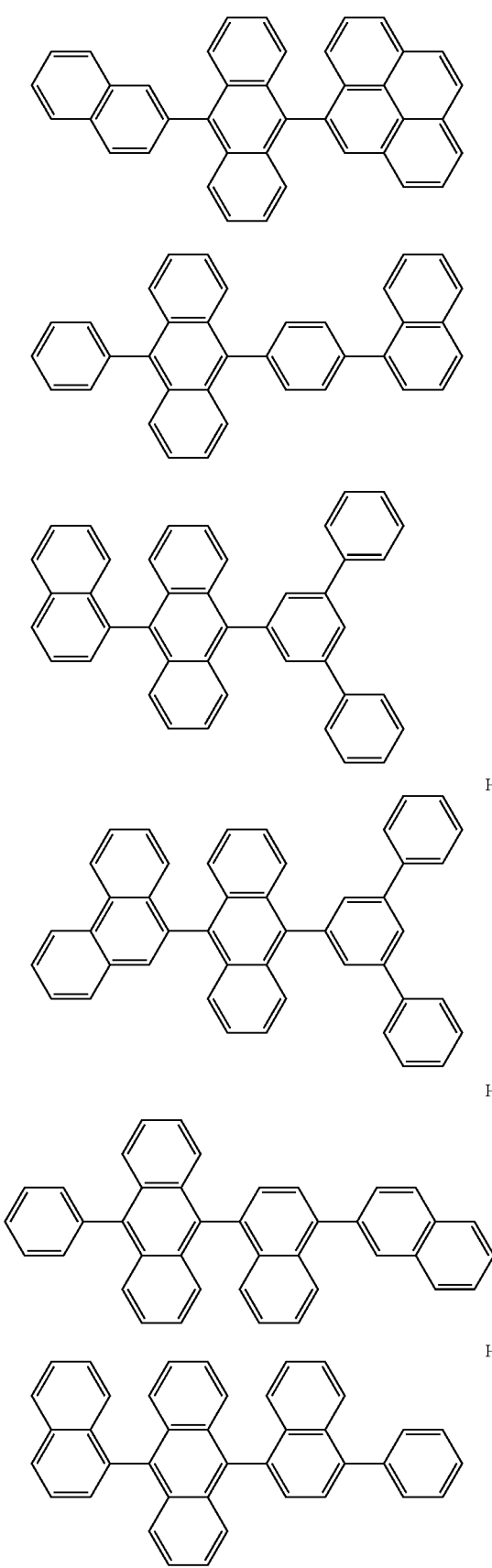
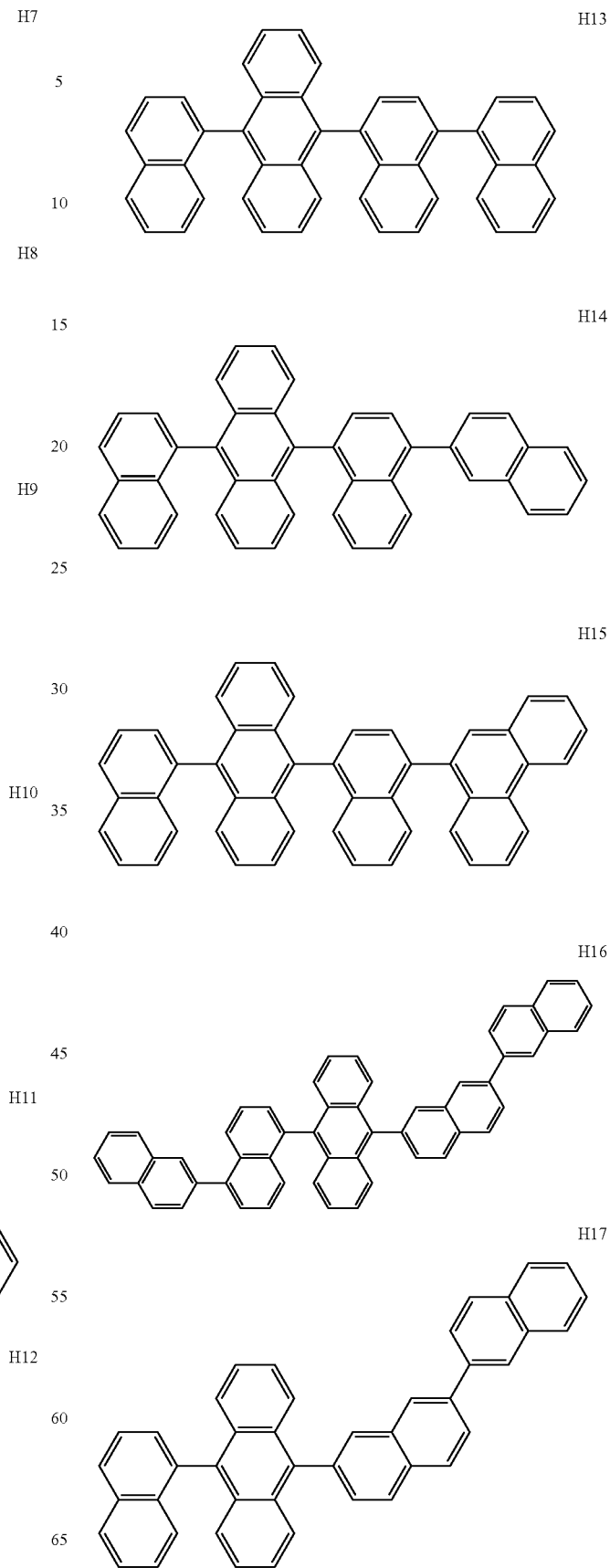

H18
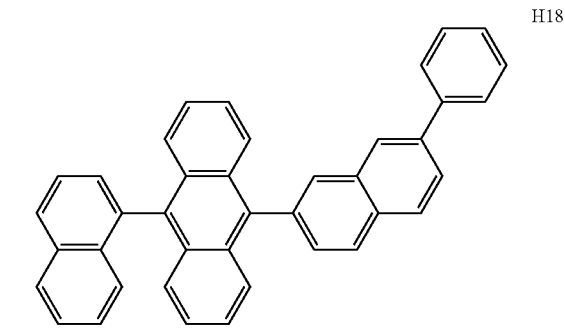
H19
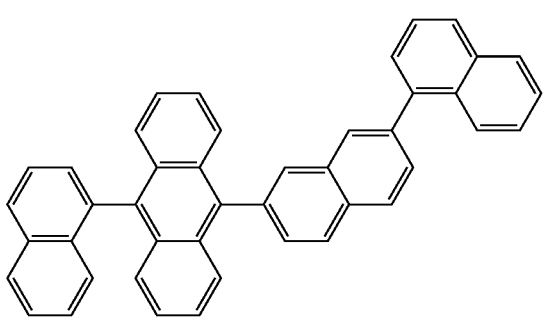
H20
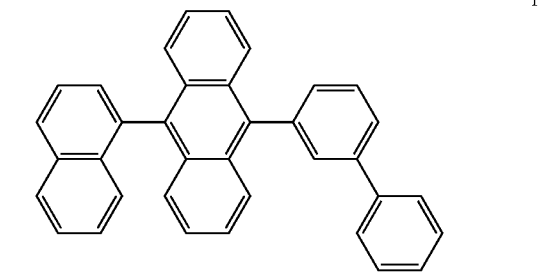
H21
H22
H23
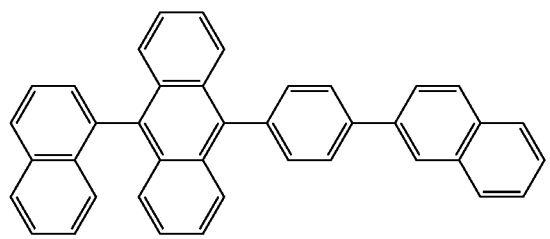
H24
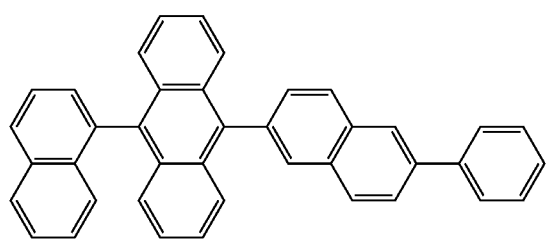
H25
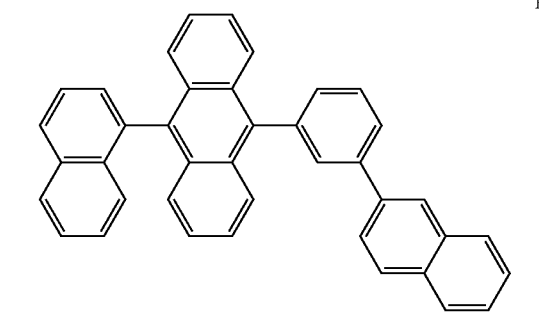
H26
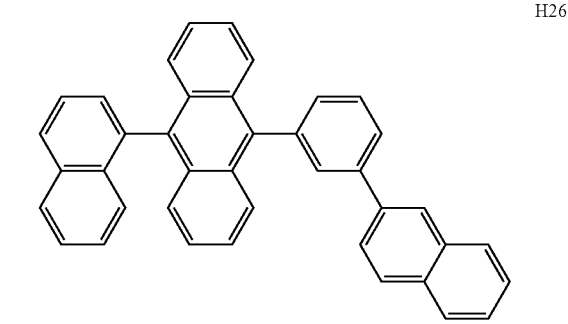
H27
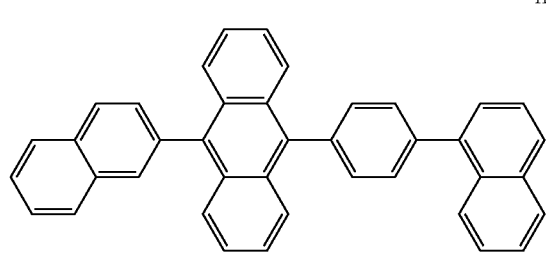

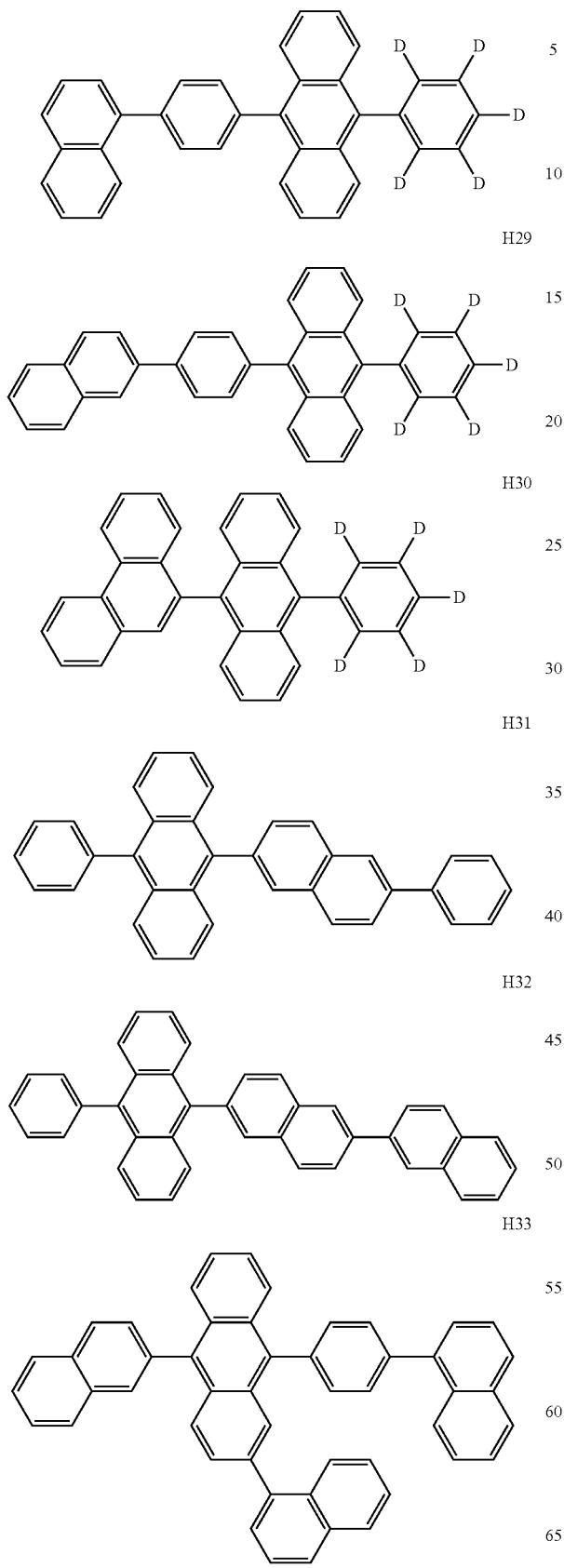

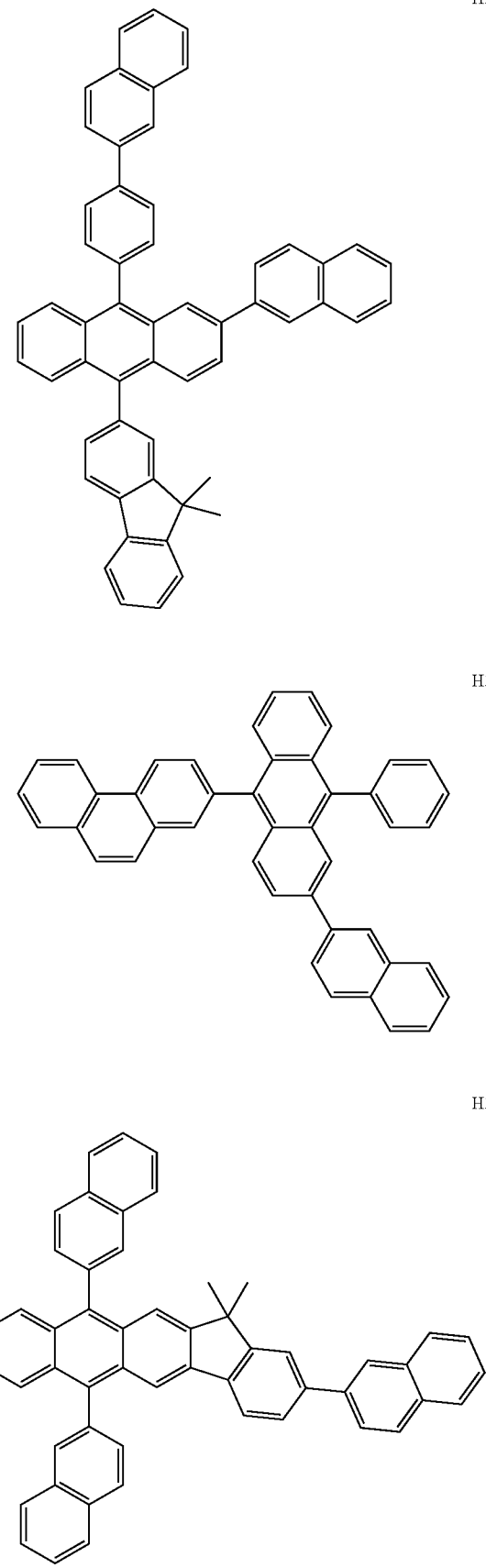

H37

H38

H39

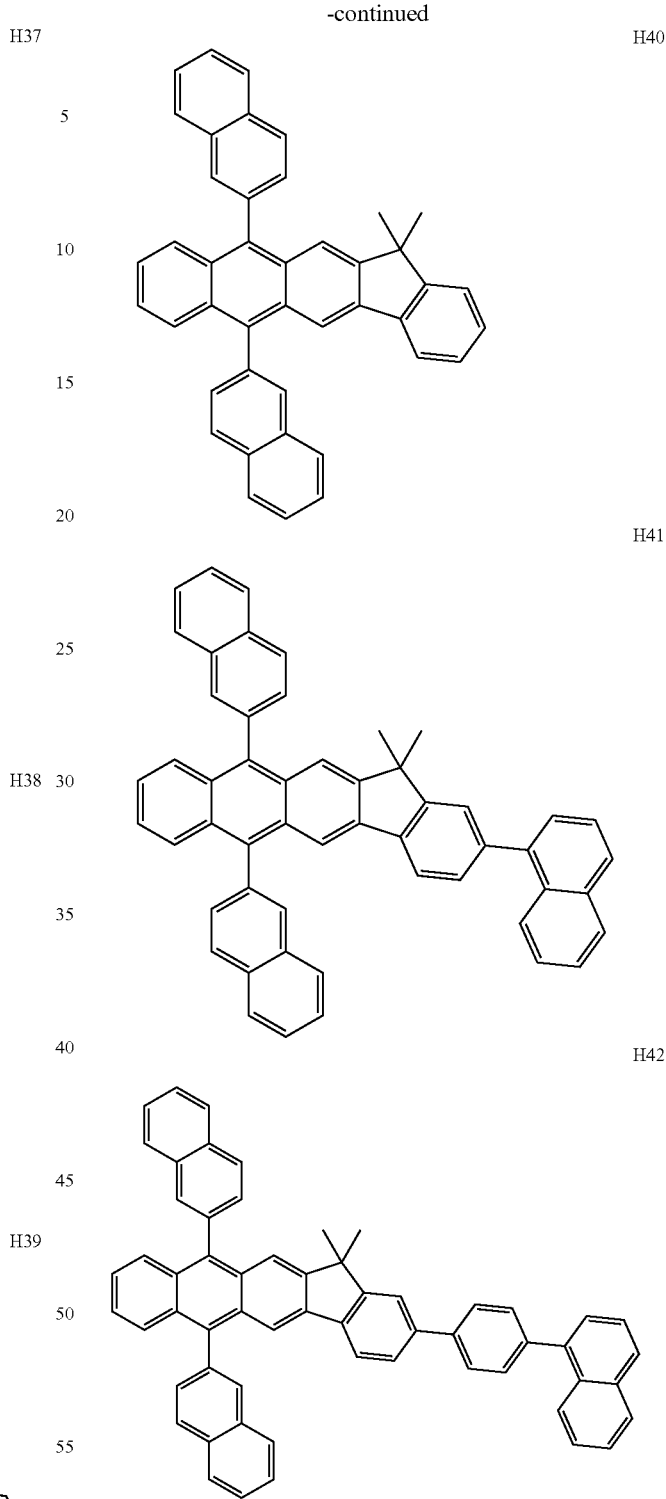

H40

H41

H42

When the organic light-emitting device is a full color organic light-emitting device, the emission layer may be patterned into a red emission layer, a green emission layer, and a blue emission layer. In some embodiments, due to a stack structure including a red emission layer, a green emission layer, and/or a blue emission layer, the emission layer may emit white light.

When the emission layer includes a host and a dopant, an amount of the dopant may be in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer, which constitute the electron transport region, may be understood by referring to the conditions for forming the hole injection layer.

When the electron transport layer includes a hole blocking layer, the hole blocking layer may include, for example, at least one of BCP, Bphen, and Balq but is not limited thereto.

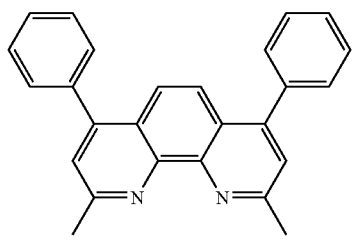

BCP

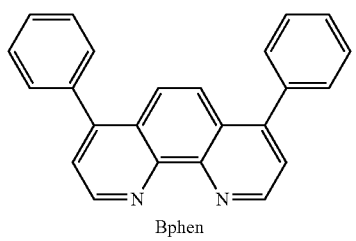

Bphen

A thickness of the hole blocking layer may be in a range of about 20 Å to about 1,000 Å, for example, about 30 Å to about 300 Å. When the thickness of the hole blocking layer is within these ranges, the hole blocking layer may have improved hole blocking ability without a substantial increase in driving voltage.

The electron transport layer may further include at least one selected from BCP, Bphen, Alq$_3$, Balq, TAZ, and NTAZ.

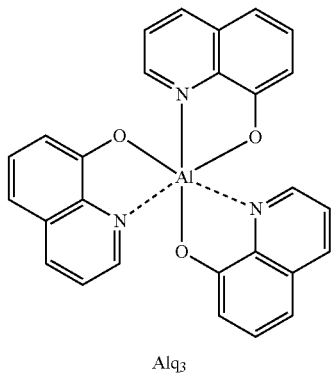

Alq$_3$

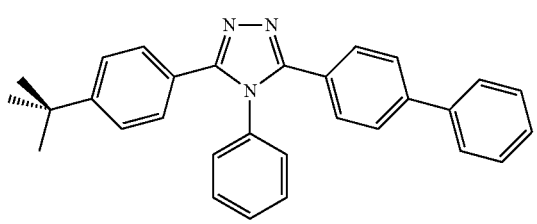

BAlq

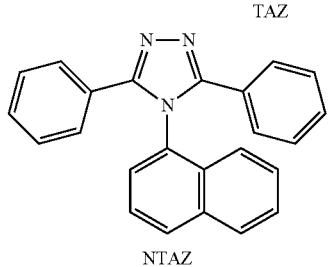

TAZ

NTAZ

In some embodiments, the electron transport layer may include at least one of ET1 and ET2, but are not limited thereto:

ET1

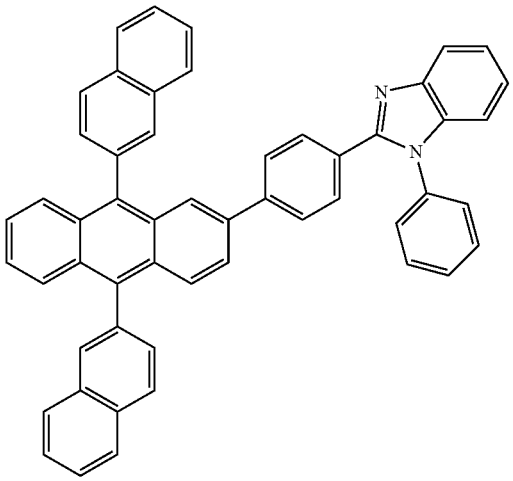

ET2

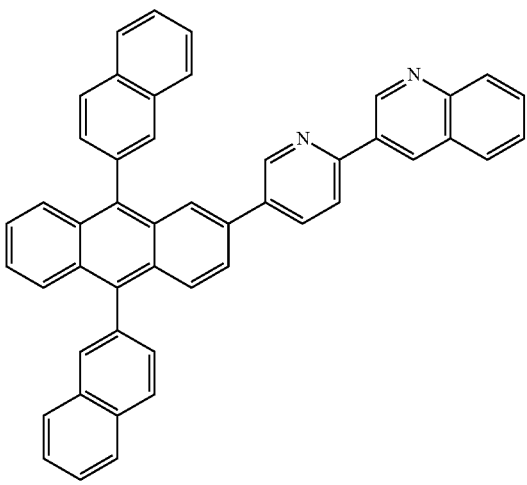

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

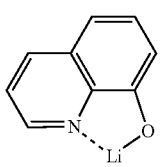

ET-D2

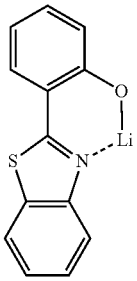

The electron transport region may include an electron injection layer (EIL) that allows electrons to be easily provided from a second electrode 19.

The electron injection layer may include at least one selected from, LiF, NaCl, CsF, $Li_2O$, BaO, and LiQ.

A thickness of the electron injection layer may be in a range of about 1 Å to about 100 Å, about 3 Å to about 90 Å. When the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as a material for forming the second electrode 19. In some embodiments, to manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a hydrocarbon group having at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group having at least one carbon trip bond in the middle or at the terminal of the $C_2$-$C_{60}$ alkyl group. Detailed examples thereof are an ethynyl group, and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent monocyclic group having at least one hetero atom selected from N, O, P, and S as a ring-forming atom and 1 to 10 carbon atoms. Detailed examples thereof are a tetrahydrofuranyl group, and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof, and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one hetero atom selected from N, O, P, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system that has at least one hetero atom selected from N, O, P, and S as a ring-forming atom, and 1 to 60 carbon atoms. A $C_1$-$C_{60}$ heteroarylene group as used herein refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group as used herein refers to a monovalent group (for example, having 8 to 60 carbon atoms) that has two or more rings condensed to each other, only carbon atoms as a ring forming atom, and which is non-aromatic in the entire molecular structure. A detailed example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group (for example, having 2 to 60 carbon atoms) that has two or more rings condensed to each other, has a heteroatom selected from N, O, P, and S, other than carbon atoms, as a ring forming atom, and which is non-aromatic in the entire molecular structure. An example of the monovalent non-aromatic condensed heteropolycyclic group is a carbazolyl group. A divalent non-aromatic condensed heteropolycyclic group as used herein refers to a divalent group having the same structure as the monovalent non-aromatic condensed heteropolycyclic group.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount (molar equivalents) of A used was identical to an amount of B used.

EXAMPLE

Synthesis Example 1: Synthesis of Compound 1

Synthesis of Intermediate (A)

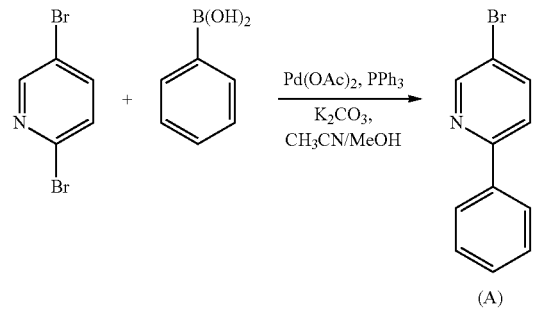

(A)

2,5-dibromopyridine (2.35 grams (g), 10 millimoles (mmol)), a phenylboronic acid (1.34 g, 11 mmol), palladium (0) acetate (Pd(OAc)$_2$, (0.09 g, 0.4 mmol), triphenylphosphine (0.26 g, 1.0 mmol), and potassium carbonate (K$_2$CO$_3$, 3.4 g, 25 mmol) were placed into a two-neck flask. Acetonitrile (CH$_3$CN, 80 milliliters (mL)) and methanol (40 mL) were added thereto, the resultant mixture was purged with nitrogen, and stirred at a temperature of 50° C. for 24 hours. Once the reaction was complete, the reaction was cooled to room temperature and filtered to remove white solid therefrom. The obtained residual solution was concentrated under reduced pressure. The product was extracted with methylene chloride (MC)/H$_2$O. The organic layer was washed with water and brine, and dried with magnesium sulfate (MgSO$_4$). The crude product was purified by column chromatography (hexane/MC=1/1) to obtain Intermediate (A) (2.1 g, yield=92%) as white solid.

MS: m/z calcd 227.38; found 227.95.

Synthesis of Intermediate (B)

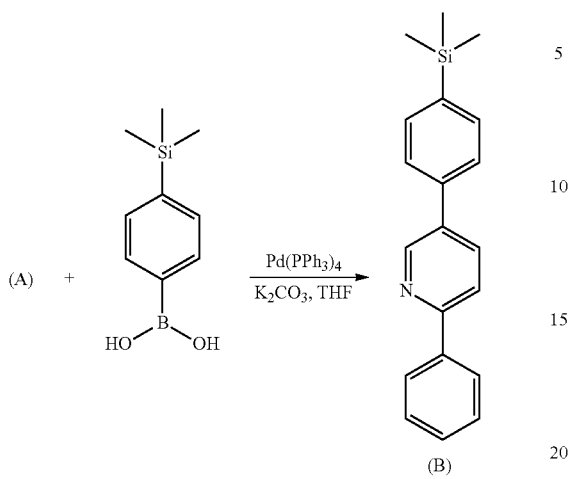

Intermediate (A) (4.7 g, 20 mmol), 4-(trimethylsilyl)phenylboronic acid (4.6 g, 24 mmol), tetrakis(triphenylphosphine)palladium(0) (Pd(PPh$_3$)$_4$, 1.6 g, 1.4 mmol) and potassium carbonate (K$_2$CO$_3$, 6.9 g, 50 mmol) were placed into a two-neck flask. 70 mL of tetrahydrofuran (THF) and 15 mL of H$_2$O were added thereto, and the resultant mixture was purged with nitrogen and refluxed for 12 hours. Thereafter, the resultant mixture was cooled to room temperature. The product was extracted with methylene chloride (MC) to obtain an organic layer, which was dried with magnesium sulfate (MgSO$_4$), concentrated, and purified with column chromatography (hexane/MC=½) to obtain Intermediate (B) (3.9 g, yield=65%).

MS: m/z calcd 302.47; found 303.35.

Synthesis of Intermediate (C)

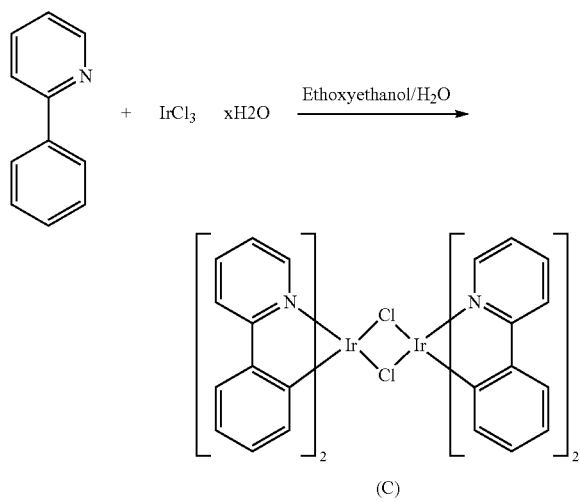

2-phenylpyridine (12.4 g, 80 mmol), iridium chloride (12.5 g, 35 mmol), ethoxyethanol (150 mL), and water (50 mL) were placed into a round flask, and refluxed at a temperature of 120° C. for 12 hours. The temperature was decreased to room temperature, and the resultant mixture was added to water to precipitate a solid. The solid was filtered, and sequentially washed with water, methanol, ether, and hexane to obtain Intermediate (C) (13 g, yield=70%).

Synthesis of Compound 1

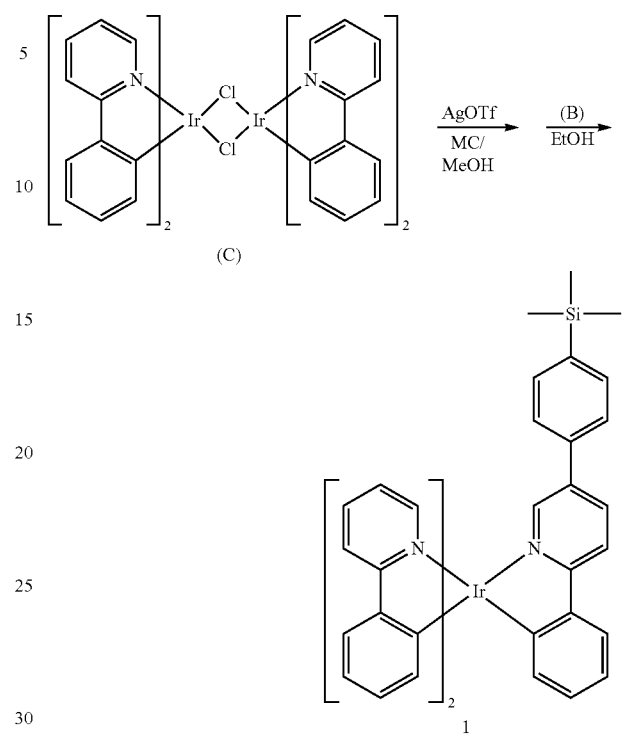

Intermediate (C) (4.28 g, 4 mmol), silver (I) trifluoromethane sulfonate (AgOTf, 2.56 g, 8 mmol), methylene chloride (MC) (100 mL), and methanol (30 mL) were placed into a round flask, and refluxed for 12 hours. The temperature was decreased to room temperature, and the resultant mixture was filtered to remove white solid therefrom. The solvent was removed under reduced pressure to obtain a solid (5.17 g, 7.2 mmol). The solid and Intermediate (B) (3.27 g, 10.8 mmol) were dissolved in ethanol, and refluxed for 12 hours. Once the reaction was complete, the temperature was decreased to room temperature/. The yellow solid obtained by filtration was purified by column chromatography (hexane/MC=1/1) to obtain Compound 1 (1.5 g, yield=23%).

MS: m/z calcd 803.06; found 804.00.

$^1$H NMR (CDCl$_3$, 300 MHz): 7.89~7.84 (m, 3H), 7.69~7.62 (m, 4H), 7.45~7.41 (m, 2H), 7.38~7.36 (m, 4H), 6.98~6.96 (d, 2H), 6.92~6.89 (m, 8H), 6.82~6.77 (m, 4H), 0.21 (s, 9H).

Synthesis Example 2: Synthesis of Compound 2

Compound 2 (1.2 g, yield=30%) was synthesized in the same manner as in Synthesis Example 1, except that in synthesis of Intermediate (B), 3-(trimethylsilyl)phenylboronic acid was used instead of 4-(trimethylsilyl)phenylboronic acid.

MS: m/z calcd 817.08; found 817.94.

$^1$H NMR (CDCl$_3$, 300 MHz): 7.88~7.84 (m, 3H), 7.67~7.61 (m, 4H), 7.45~7.42 (m, 2H), 7.37~7.34 (m, 4H), 6.98~6.96 (d, 2H), 6.95~6.89 (m, 8H), 6.82~6.78 (m, 4H), 0.21 (s, 9H).

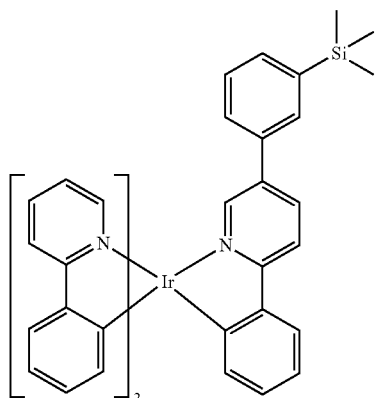

Synthesis Example 3: Synthesis of Compound 3

Synthesis of Intermediate (D)

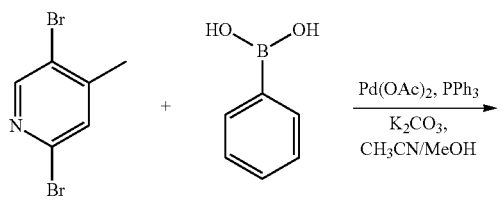

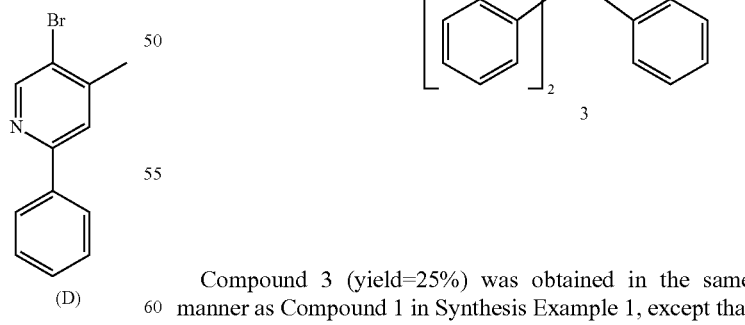

Intermediate (D) (yield=85%) was obtained in the same manner as Intermediate (A) in Synthesis Example 1, except that 2,5-dibromo-4-methylpyridine was used instead of 2,5-dibromopyridine.

MS: m/z calcd 248.12; found 249.01.

Synthesis of Intermediate (E)

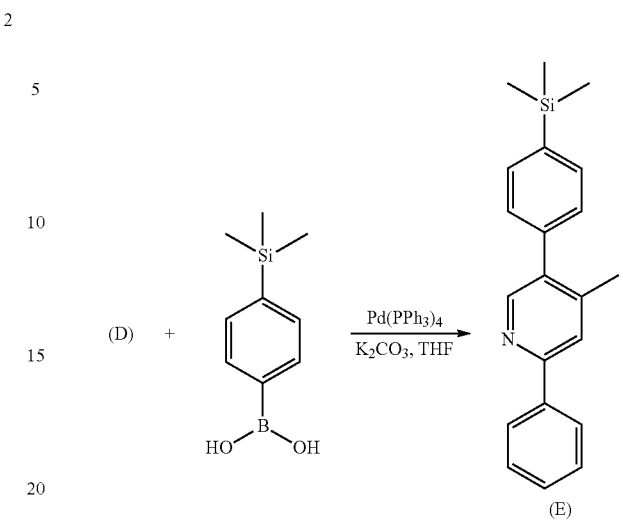

Intermediate (E) (yield of 62%) was synthesized in the same manner as Intermediate (B) in Synthesis Example 1, except that Intermediate (D) was used instead of Intermediate (A).

MS: m/z calcd 317.50; found 318.27.

Synthesis of Compound 3

Compound 3 (yield=25%) was obtained in the same manner as Compound 1 in Synthesis Example 1, except that Intermediate (E) was used instead of Intermediate (B).

MS: m/z calcd 817.08; found 818.04.

$^1$H NMR (CDCl$_3$, 300 MHz): 7.78 (t, 2H), 7.67 (s, 1H), 7.64~7.50 (m, 4H), 7.47~7.42 (m, 2H), 7.41~7.39 (m, 4H), 7.35 (s, 1H), 7.02~7.00 (d, 2H), 6.89~6.81 (m, 8H), 6.81~6.77 (m, 2H), 2.32 (s, 3H), 0.20 (s, 9H).

Synthesis Example 4: Synthesis of Compound 4

Synthesis of Intermediate (F)

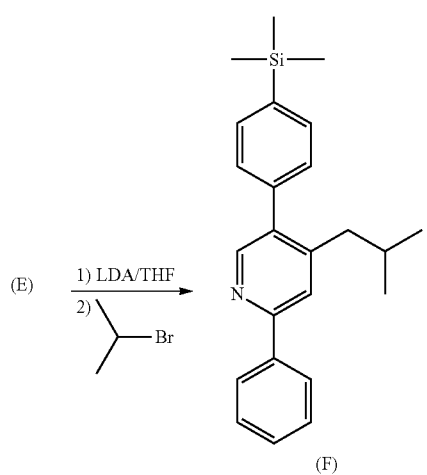

Intermediate (E) (6.3 g, 20 mmol), lithium diisopropylamide (LDA, 2.2 equivalents (eq)) (4.7 g, 44 mmol), and THF (50 mL) were placed into a two-neck flask, and the mixture was stirred at a temperature of −70° C. for 30 minutes. 2-bromopropane (5.9 g, 48 mmol) was slowly added by drops thereto. The resultant mixture was subsequently stirred at a temperature of −70° C. for 24 hours. The temperature was slowly raised to room temperature. Water was added thereto to quench the reaction. The product was extracted with methylene chloride (MC). The combined organic layers were dried with magnesium sulfate (MgSO$_4$) and concentrated. The product was purified by column chromatography (hexane/MC=1/1) to obtain Intermediate (F) (5.2 g, yield=73%).

MS: m/z calcd 359.58; found 360.45.

Synthesis of Compound 4

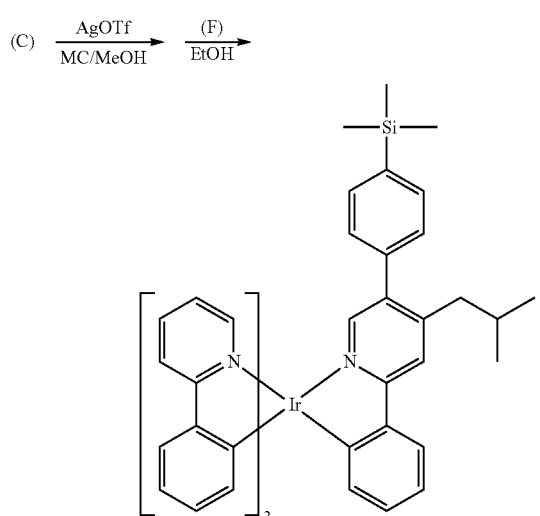

Compound 4 (yield=21%) was obtained in the same manner as Compound 1 in Synthesis Example 1, except that Intermediate (F) was used instead of Intermediate (B).

MS: m/z calcd 859.16; found 860.05.

$^1$H NMR (CDCl$_3$, 300 MHz): 7.79 (t, 2H), 7.65 (s, 1H), 7.64~7.50 (m, 4H), 7.47~7.43 (m, 2H), 7.42~7.39 (m, 4H), 7.35 (s, 1H), 7.02~7.00 (d, 2H), 6.89~6.81 (m, 8H), 6.81~6.77 (m, 2H), 2.52 (d, 2H), 1.90 (m, 1H), 0.93 (d, 6H), 0.23 (s, 9H)

Synthesis Example 5: Synthesis of Compound 9

Synthesis of Intermediate (G)

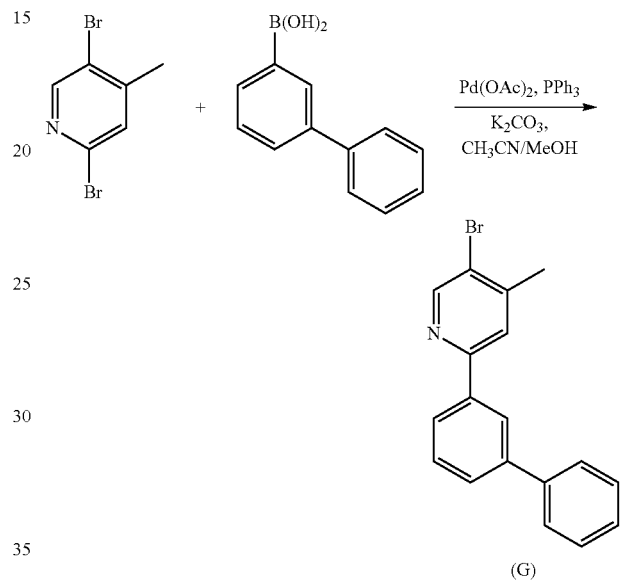

Intermediate (G) (yield=82%) was obtained in the same manner as Intermediate (A) in Synthesis Example 1, except that [1,1'-biphenyl]-3-boronic acid was used instead of a phenylboronic acid.

MS: m/z calcd 324.21; found 325.15.

Synthesis of Intermediate (H)

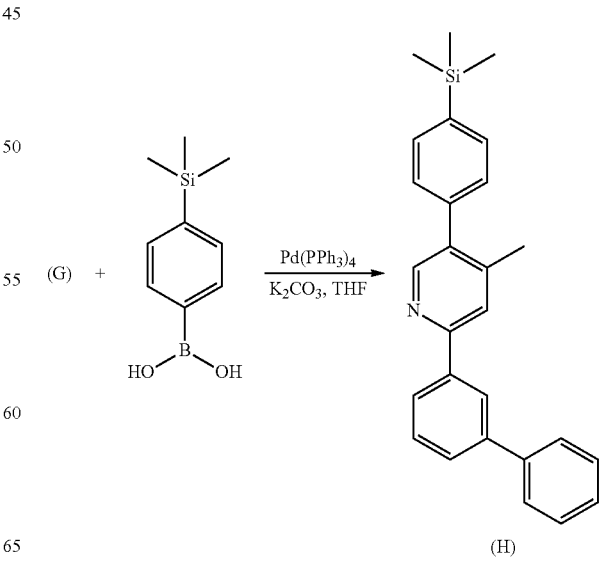

Intermediate (H) (yield of 78%) was synthesized in the same manner as Intermediate (B) of Synthesis Example 1, except that Intermediate (G) was used instead of Intermediate (A).

MS: m/z calcd 393.60; found 394.52.

Synthesis of Compound 9

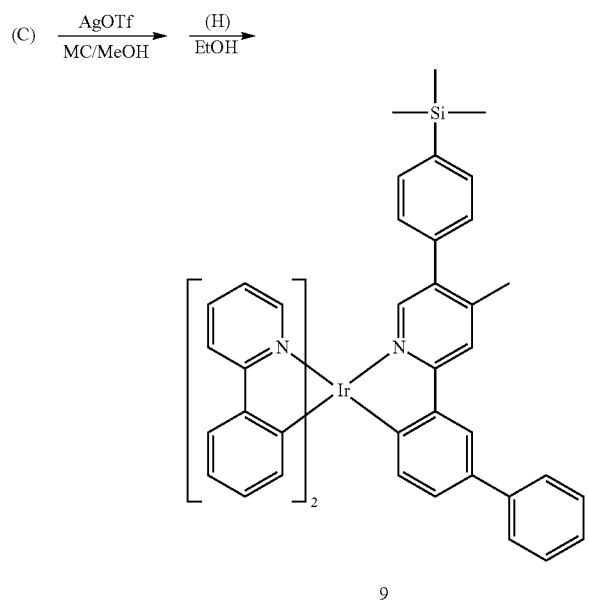

9

Compound 9 (yield=18%) was obtained in the same manner as Compound 1 in Synthesis Example 1, except that Intermediate (H) was used instead of Intermediate (B).

MS: m/z calcd 893.18; found 894.07.

$^1$H NMR (CDCl$_3$, 300 MHz): 7.80 (m, 2H), 7.64 (s, 1H), 7.62~7.51 (m, 4H), 7.47~7.43 (m, 2H), 7.41~7.38 (m, 4H), 7.34 (s, 1H), 7.02~7.00 (d, 4H), 6.89~6.80 (m, 12H), 2.32 (s, 3H), 0.21 (s, 9H)

Synthesis Example 6: Synthesis of Compound 5

Compound 5 was synthesized in the same manner as in Synthesis Example 1, except that in synthesis of Intermediate (B), 2-(methyl)-4-(trimethylsilyl)phenylboronic acid was used instead of 4-(trimethylsilyl)phenylboronic acid.

Synthesis Example 7: Synthesis of Compound 6

Compound 6 was synthesized in the same manner as in Synthesis Example 1, except that in synthesis of Intermediate (B), 2-(t-butyl)-4-(trimethylsilyl)phenylboronic acid was used instead of 4-(trimethylsilyl)phenylboronic acid.

Synthesis Example 8: Synthesis of Compound 7

Compound 7 was synthesized in the same manner as in Synthesis Example 3, except that in synthesis of Intermediate (B), 2-(methyl)-4-(trimethylsilyl)phenylboronic acid was used instead of 4-(trimethylsilyl)phenylboronic acid.

Evaluation Example 1: Evaluation of Thermal Characteristics

Figure 2:
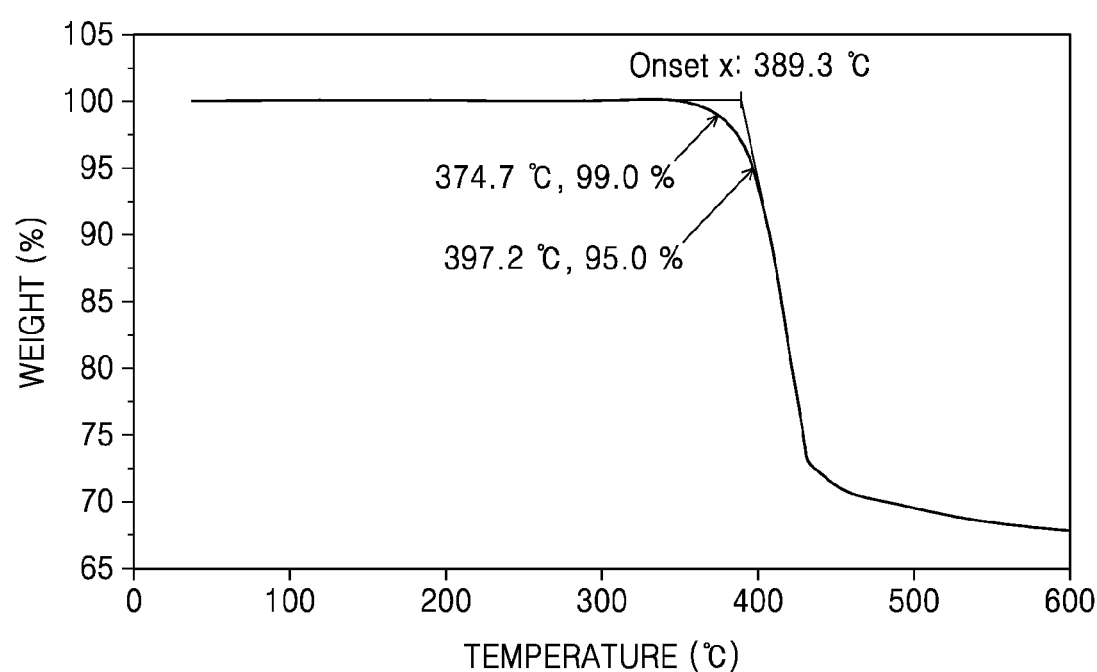
FIG. 2 is a graph of weight (percent, %) versus temperature (degree Centigrade, °C.) showing thermogravimetric analysis (TGA) data of Compound 3.

Compound 3 was subjected to thermal analysis (N$_2$ atmosphere, temperature range: room temperature to 800° C. (10 degrees Centigrade per minute (° C./min))-TGA, room temperature to 450° C.-DSC, Pan Type: Pt Pan in disposable Al Pan (TGA), disposable Al pan (DSC)) using thermogravimetric analysis (TGA) and differential scanning calorimetry (DSC). The obtained results are shown in FIG. 2 and Table 2 below. Referring to FIG. 2 and Table 2, it was confirmed that Compound 3 had excellent thermal stability.

TABLE 2

|  | Td (° C.) (1%, 5%) | Tg (° C.) | Tm (° C.) |
| --- | --- | --- | --- |
| Compound 3 | 374, 397 | not detected. | not detected. |

Evaluation Example 2: Evaluation on HOMO, LUMO, and T$_1$ Energy Levels

HOMO, LUMO and T$_1$ energy levels of Compound 3 were evaluated according to the method indicated in Table 3, and results thereof are shown in Table 4.

TABLE 3

| | |
| --- | --- |
| HOMO energy level evaluation method | Each compound was diluted at a concentration of 1 × 10$^{-5}$ molar (M) in CHCl$_3$, and an UV absorption spectrum thereof was measured at room temperature by using a Shimadzu UV-350 spectrometer. The HOMO energy level thereof was calculated by using an optical band gap (Eg) from an edge of the absorption spectrum. |
| LUMO energy level evaluation method | A potential (Volts, V)-current (Amperes, A) graph of each compound was obtained by using cyclic voltammetry (CV) (electrolyte: 0.1M Bu$_4$NClO$_4$/solvent: CH$_2$Cl$_2$/electrode: 3 electrode system (working electrode: GC, reference electrode: Ag/AgCl, auxiliary electrode: Pt)). Subsequently, from reduction onset of the graph, the LUMO energy level of the compound was calculated. |
| T1 energy level evaluation method | A mixture (each compound was dissolved in an amount of 1 milligram (mg) in 3 cubic centimeters (cc) of toluene) of toluene and each compound was loaded into a quartz cell, and then, the resultant quartz cell was loaded into liquid nitrogen (77 Kelvins (K)). A photoluminescence spectrum thereof was measured by using a device for measuring photoluminescence. The obtained spectrum was compared with a photoluminescence spectrum measured at room temperature, and peaks observed only at low temperature were analyzed to calculate T1 energy levels. |

TABLE 4

| Compound No. | HOMO (eV) (found) | LUMO (eV) (found) | T$_1$ energy level (eV) |
| --- | --- | --- | --- |
| Compound 1 | −5.049 | −2.521 | 2.375 |
| Compound 2 | −5.043 | −2.523 | 2.396 |
| Compound 3 | −5.016 | −2.486 | 2.455 |
| Compound 4 | −5.007 | −2.400 | 2.507 |
| Compound 5 | −5.045 | −2.507 | 2.432 |
| Compound 6 | −5.040 | −2.465 | 2.451 |
| Compound 7 | −5.013 | −2.379 | 2.510 |

From Table 4, it was confirmed that Compounds 1 to 7 have electric characteristics that are suitable for use as a material for forming an organic light-emitting device.

Evaluation Example 3: Luminance Characteristics Evaluation

UV absorption spectrum and photoluminescence (PL) spectrum of Compound 3 were analyzed to evaluate luminance characteristics thereof. First, Compound 3 was diluted in toluene to a concentration of 0.2 millimolar (mM), and then analyzed by Shimadzu UV-350 Spectrometer to obtain an UV absorption spectrum. Compound 3 was diluted in toluene to a concentration of 10 mM, and then analyzed by Xenon-equipped ISC PC1 spectrofluorometer to obtain a PL spectrum. Results thereof are shown in Table 3.

Figure 3:
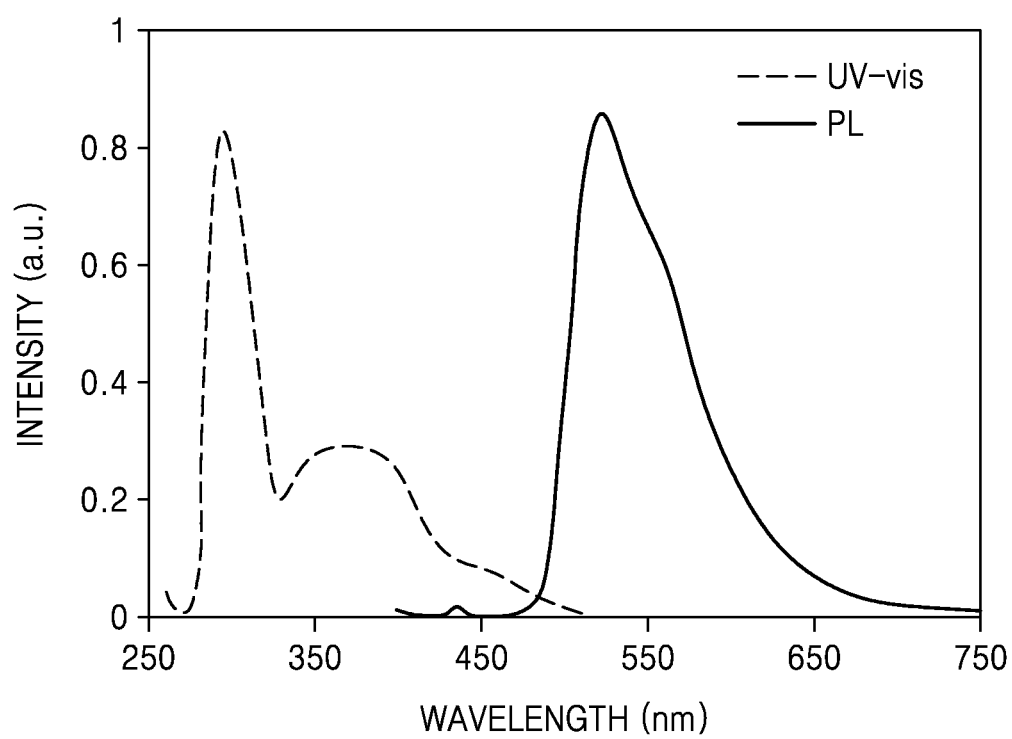
FIG. 3 is a graph of intensity (arbitrary unit, a. u.) versus wavelength (nanometer, nm) showing an ultraviolet (UV)-absorption spectrum and a photoluminescent (PL) of Compound 3 in solution.

Referring to FIG. 3, it was confirmed that Compound 3 has luminance characteristics that are suitable for use as a material for an organic light-emitting device.

Evaluation Example 4: Process Stability Evaluation

Figure 4:
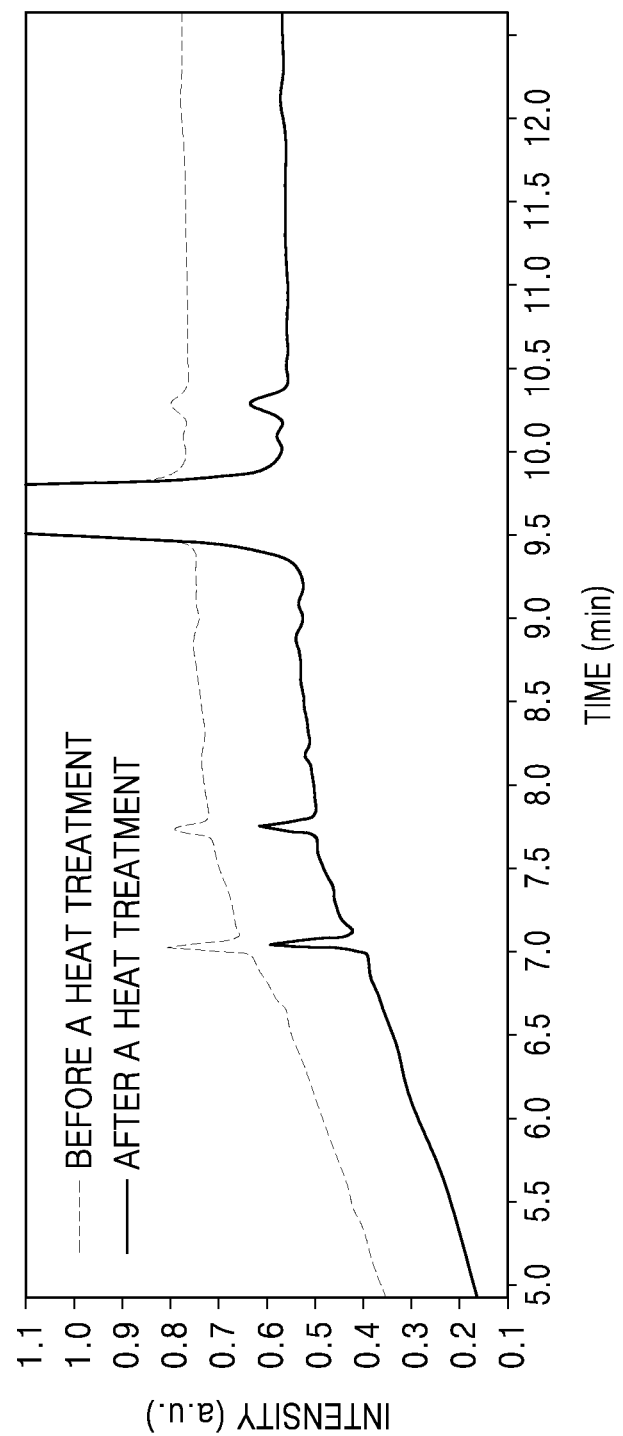
FIG. 4 is a graph of intensity (arbitrary unit, a. u.) versus time (minute, min) showing high performance liquid chromatography (HPLC) data of Compound 3 to explain a purity change after a heat treatment of Compound 3.
Figure 5:
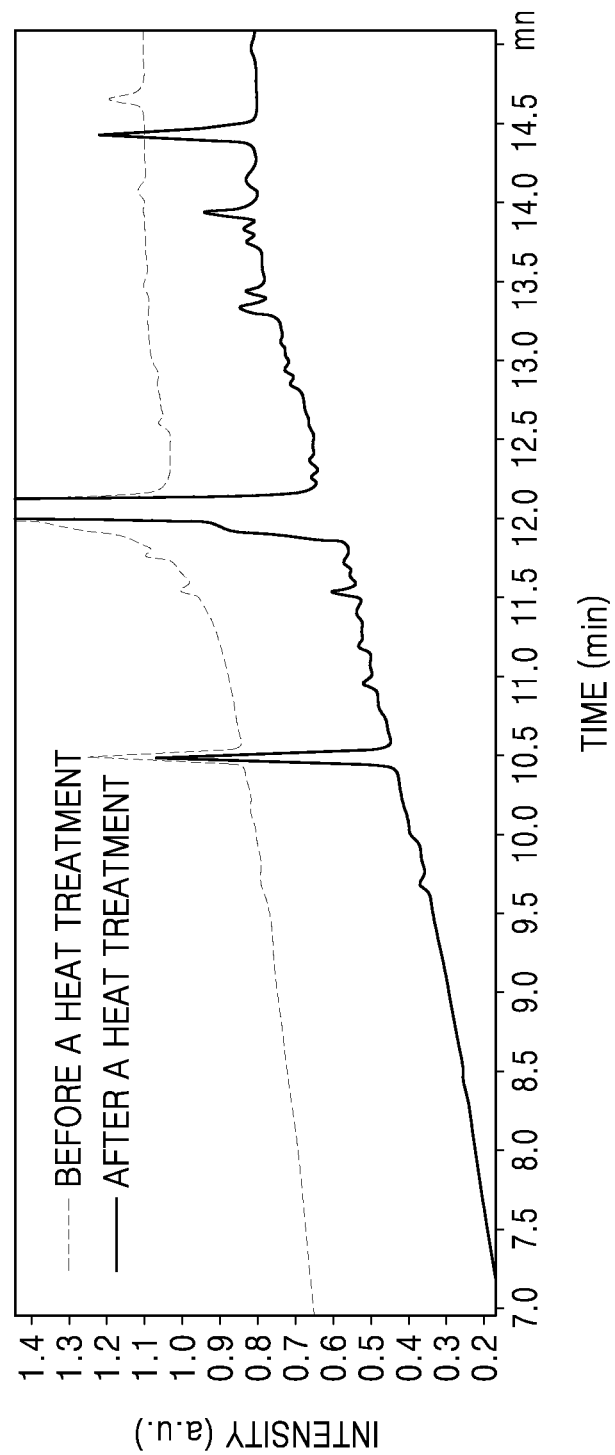
FIG. 5 is a graph of intensity (arbitrary unit, a. u.) versus time (minute, min) showing HPLC data of Compound A to explain a purity change after a heat treatment of Compound A.

Heat-resistant stability and process stability of Compound 3 were evaluated by analyzing purify levels before and after Compound 3 and Compound A were heat treated. First, Compound 3 and Compound A were heat treated under a nitrogen atmosphere (180° C., 100 hours), and a change in purity of Compound 3 and Compound A was measured by high performance liquid chromatography (HPLC). Results thereof are shown in FIG. 4 (Compound 3) and FIG. 5 (Compound A), and summarized in Table 5.

Compound A

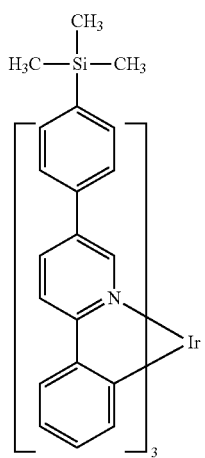

TABLE 5

| Compound No. | Purity level before the heat treatment (%) | Purity level after the heat treatment (%) | Purity change (%) |
|---|---|---|---|
| Compound 3 | 99.47 | 99.46 | 0.01 |
| Compound A | 99.30 | 95.90 | 3.80 |

Figure 6:
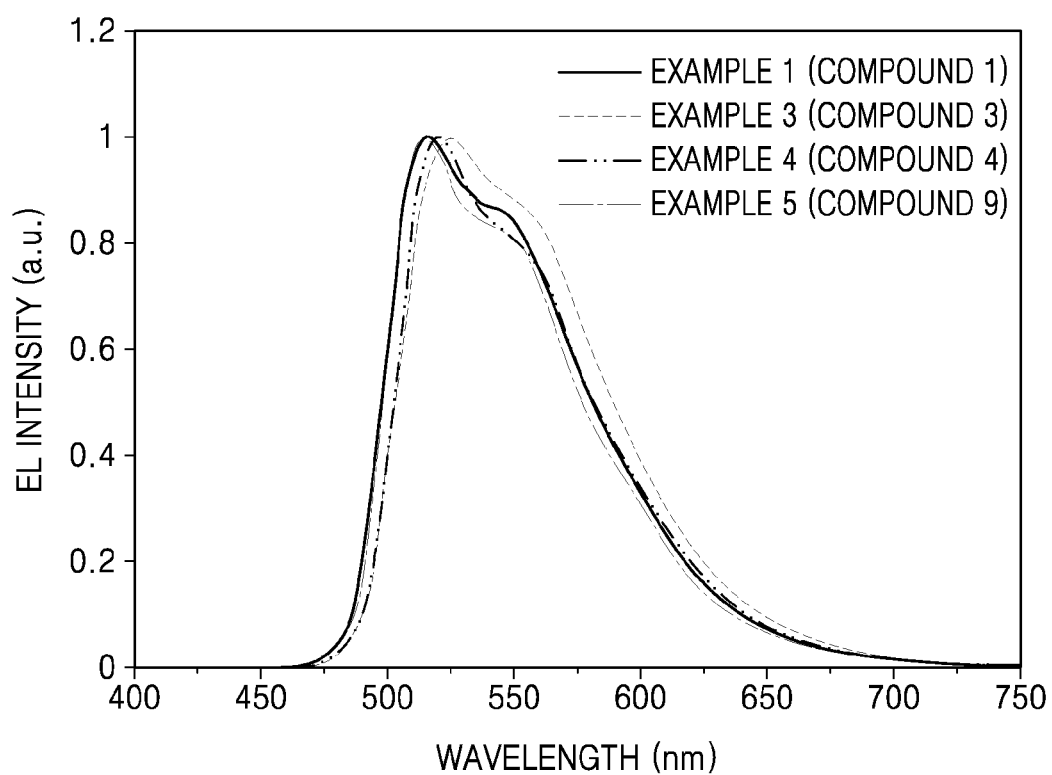
FIG. 6 is a graph of electroluminescent (EL) intensity (arbitrary unit, a. u.) versus wavelength (nanometer, nm) showing an electroluminescent (EL) spectrum of organic light-emitting devices manufactured according to Examples 1, 3, 4, and 5.

Referring to Table 5 and FIGS. 4 and 6, it was confirmed that Compound 3 had heat-resistant stability. Accordingly, it was confirmed that Compound 3 had excellent process stability that minimizes the difference in characteristics of a device depending on a process time during a deposition process that is required in manufacturing an organic light-emitting device.

Example 1

A glass substrate with ITO/Ag/ITO (70 Å/1,000 Å/70 Å) as an anode thereon was cut to a size of 50 millimeters (mm)×50 mm×0.5 mm, sonicated in isopropyl alcohol and pure water for about 5 minutes, and cleaned by irradiation of ultraviolet rays for 30 minutes and exposure to ozone. The resultant structure was subsequently mounted on a vacuum deposition apparatus.

2-TNATA was deposited on the anode to form a hole injection layer having a thickness of 60 nanometers (nm), and NPB was deposited on the hole injection layer to form a hole transport layer having a thickness of 100 nm. CBP (host) and Compound 1 (dopant) were co-deposited on the hole transport layer at a weight ratio of 90:10 to form an emission layer having a thickness of 25 nm. BCP was deposited on the emission layer to form a hole blocking layer having a thickness of 5 nm. $Alq_3$ was deposited on the hole blocking layer to form an electron transport layer having a thickness of 35 nm. LiF was deposited on the electron transport layer to form an electron injection layer having a thickness of 1 nm. Mg and Ag were co-deposited on the electron injection layer at a weight ratio of 9:1 to form a cathode having a thickness of 12 nm, thereby completing manufacture of an organic light-emitting device (emission of green light).

Examples 2 to 5 and Comparative Example 1

An organic light-emitting device was manufactured in the same manner as in Example 1, except that in forming an emission layer, a dopant shown in Table 6 was used instead of Compound 1.

Figure 7:
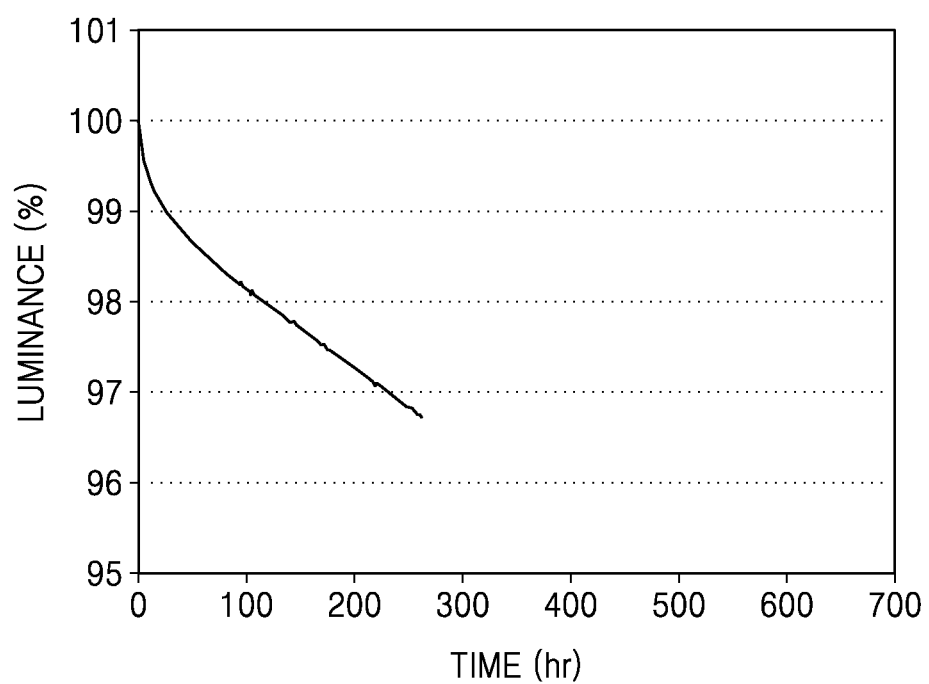
FIG. 7 is a graph of luminance (percent, %) versus time (hour, hr) showing lifetime data (at 10 milliAmperes per square centimeter ($mA/cm^2$)) of the organic light-emitting device manufactured according to Example 3.

Evaluation Example 5: Evaluation of Characteristics of Organic Light-Emitting Devices The driving voltage, efficiency, luminance, lifespan ($T_{97}$), and color purity of the organic light-emitting devices of Examples 1 to 5 and Comparative Example 1 were evaluated, and evaluation results are shown in Table 6. EL spectra of the organic light-emitting devices of Examples 1, 3, 4 and 5 are shown in Table 6. FIG. 7 shows a time-luminance (at 10 milliAmperes per square meter ($mA/m^2$)) graph of the organic light-emitted device of Example 3. The efficiency, luminance, and color coordinate of each of the organic light-emitting device were measured by using a luminance meter PR650 while power source was supplied thereto by a current-voltage meter (Kethley SMU 236). A lifespan was obtained by measuring an amount of time that lapsed when luminance was reduced from 100% (initial luminance) to 97% at the current density of 10 milliAmperes per square centimeter ($mA/cm^2$).

TABLE 6

| | Dopant | Driving Voltage (V) | Efficiency (Cd/A) | Luminance ($cd/m^2$) | $T_{97}$ (hr) (at 10 mA/ $cm^2$) | Color coordinate | |
|---|---|---|---|---|---|---|---|
| | | | | | | CIEx | CIEy |
| Example 1 | Compound 1 | 5.5 | 99.8 | 9000 | 123 | 0.37 | 0.59 |
| Example 2 | Compound 2 | 5.3 | 92.4 | 9000 | 100 | 0.34 | 0.60 |
| Example 3 | Compound 3 | 5.3 | 87.6 | 9000 | 230 | 0.34 | 0.61 |
| Example 4 | Compound 4 | 5.5 | 100.4 | 9000 | 250 | 0.35 | 0.60 |
| Example 5 | Compound 9 | 5.1 | 95.4 | 9000 | 114 | 0.36 | 0.59 |

TABLE 6-continued

| | | Driving Voltage (V) | Effi- ciency (Cd/A) | Lumi- nance (cd/m²) | T97 (hr) (at 10 mA/ cm²) | Color coordinate | |
|---|---|---|---|---|---|---|---|
| Dopant | | | | | | CIEx | CIEy |
| Com- parative Example 1 | Ir(PPY)3 | 5.8 | 90.2 | 9000 | 35 | 0.33 | 0.61 |

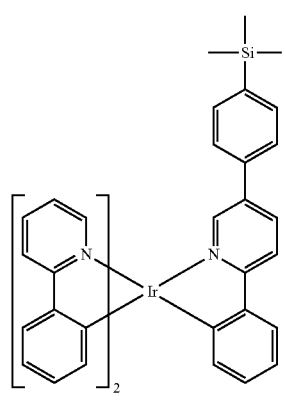

1

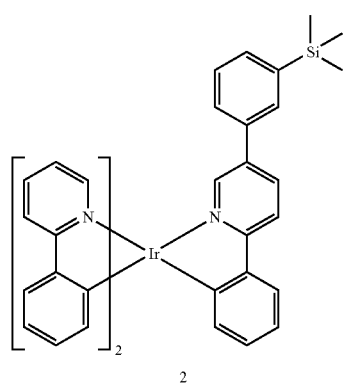

2

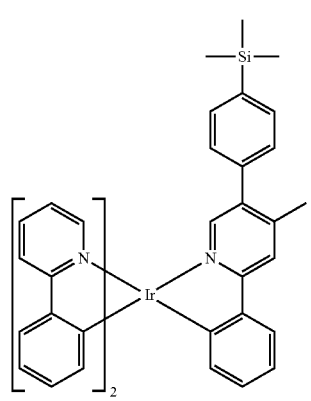

3

TABLE 6-continued

| | Driving Voltage (V) | Effi- ciency (Cd/A) | Lumi- nance (cd/m²) | T97 (hr) (at 10 mA/ cm²) | Color coordinate | |
|---|---|---|---|---|---|---|
| Dopant | | | | | CIEx | CIEy |

[Structure 4]

4

[Structure 9]

9

Referring to Table 6, it was confirmed that the organic light-emitting devices manufactured according to Examples 1 to 5 have a lower driving voltage, higher efficiency, higher luminance, a longer lifespan, and a higher color purity than the organic light-emitting devices manufactured according to Comparative Example 1.

The organometallic compound according to embodiments has excellent electric characteristics and thermal stability. Accordingly, an organic light-emitting device including the organometallic compound may have a low driving voltage, high efficiency, and high color purity.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:
1. An organometallic compound represented by Formula 1:

Formula 1

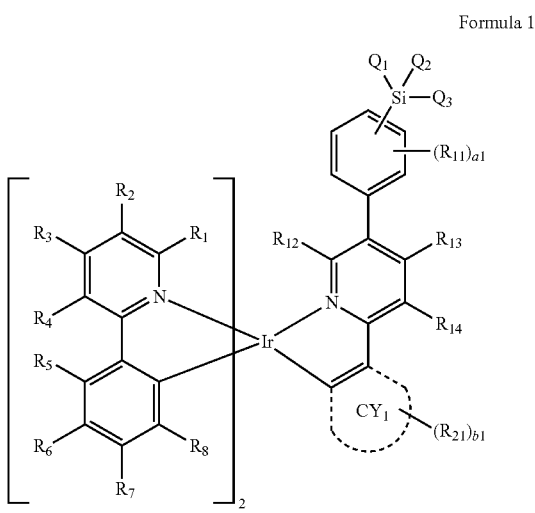

wherein in Formula 1,
$CY_1$ is selected from a $C_5$-$C_{60}$ carbocyclic group and a $C_1$-$C_{60}$ heterocyclic group,
$Q_1$ to $Q_3$ are each independently selected from
a $C_1$-$C_{20}$ alkyl group and a phenyl group; and
a $C_1$-$C_{20}$ alkyl group and a phenyl group, each substituted with at least one selected from a deuterium, a $C_1$-$C_{10}$ alkyl group, and a phenyl group,
$R_1$ to $R_8$ are each independently selected from a hydrogen, a deuterium, —$CH_3$, —$CDH_2$, —$CD_2H$, and —$CD_3$,
$R_{11}$ to $R_{14}$ are each independently selected from
a hydrogen, a deuterium, a $C_1$-$C_{10}$ alkyl group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a phenyl group, and a naphthyl group; and
a $C_1$-$C_{10}$ alkyl group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a phenyl group, and a naphthyl group, each substituted with at least one selected from a deuterium, a $C_1$-$C_{10}$ alkyl group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a phenyl group, and a naphthyl group,
$R_{21}$ is selected from
a hydrogen, a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group; and
—$N(Q_{11})(Q_{12})$ and —$P(=O)(Q_{13})(Q_{14})$,
a1 and b1 are each independently an integer selected from 0 to 4, provided that when a1 is 2 or more, 2 or more, groups $R_{11}$ are identical or different, and when b1 is 2 or more, 2 or more groups $R_{21}$ are identical or different, and
$Q_{11}$ to $Q_{14}$ are each independently selected from a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, and a $C_6$-$C_{14}$ aryl group; a $C_6$-$C_{14}$ aryl group substituted with at least one selected from a $C_1$-$C_{20}$ alkyl group and a $C_6$-$C_{14}$ aryl group; a $C_1$-$C_{14}$ heteroaryl group, a monovalent non-aromatic condensed polycyclic group, and a monovalent non-aromatic condensed heteropolycyclic group.
2. The organometallic compound of claim 1, wherein
$CY_1$ is selected from a benzene, a dibenzofuran, a dibenzothiophene, a fluorene, and a carbazole.
3. The organometallic compound of claim 1, wherein
$Q_1$ to $Q_3$ are each independently selected from
a $C_1$-$C_{10}$ alkyl group and a phenyl group; and
a $C_1$-$C_{10}$ alkyl group and a phenyl group, each substituted with at least one selected from a deuterium and a $C_1$-$C_{10}$ alkyl group.
4. The organometallic compound of claim 1, wherein
$Q_1$ to $Q_3$ are each independently selected from
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;
an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group; and an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group, each substituted with at least one selected from a deuterium and a $C_1$-$C_{10}$ alkyl group.

5. The organometallic compound of claim 1, wherein
$Q_1$ to $Q_3$ are all identical;
$Q_1$ and $Q_3$ are identical, and $Q_2$ and $Q_1$ are different from each other; or
$Q_1$ to $Q_3$ are all different from each other.

6. The organometallic compound of claim 1, wherein
$Q_1$ and $Q_3$ are each independently selected from —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$,
$Q_2$ is selected from
an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group; and
an n-propyl group, an isopropyl group, an n-butyl group, an isobutyl group, a sec-butyl group, a tert-butyl group, an n-pentyl group, an isopentyl group, a sec-pentyl group a tert-pentyl group, and a phenyl group, each substituted with at least one selected from a deuterium and a $C_1$-$C_{10}$ alkyl group.

7. The organometallic compound of claim 1, wherein
$R_1$ to $R_8$ are all a hydrogen;
$R_1$, $R_2$, and $R_4$ to $R_8$ are a hydrogen, and $R_3$ is selected from a deuterium, —$CH_3$, —$CDH_2$, —$CD_2H$, and —$CD_3$;
$R_1$, $R_2$, $R_4$, $R_5$, $R_6$ and $R_8$ are a hydrogen, and $R_3$ and $R_7$ are each independently selected from a deuterium, —$CH_3$, —$CDH_2$, —$CD_2H$, and —$CD_3$;
$R_1$ to $R_4$ are a hydrogen, and $R_5$ to $R_8$ are each independently selected from a deuterium, —$CH_3$, —$CDH_2$, —$CD_2H$, and —$CD_3$;
$R_1$ to $R_5$ are a hydrogen, and $R_6$ to $R_8$ are each independently selected from a deuterium, —$CH_3$, —$CDH_2$, —$CD_2H$, and —$CD_3$;
$R_1$ to $R_4$ and $R_8$ are a hydrogen, and $R_5$ to $R_7$ are each independently selected from a deuterium, —$CH_3$, —$CDH_2$, —$CD_2H$, and —$CD_3$; or
$R_1$ to $R_8$ are each independently selected from a deuterium, —$CH_3$, —$CDH_2$, —$CD_2H$, and —$CD_3$.

8. The organometallic compound of claim 1, wherein
$R_{11}$ to $R_{14}$ are each independently selected from
a hydrogen, a deuterium, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, and a naphthyl group; and a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, and a naphthyl group, each substituted with at least one selected from a deuterium, a $C_1$-$C_{10}$ alkyl group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, and a naphthyl group.

9. The organometallic compound of claim 1, wherein
$R_{11}$ to $R_{14}$ are each independently selected from a hydrogen, a deuterium, —$CH_3$, —$CD_3$, —$CD_2H$, —$CDH_2$, a group represented by Formulae 9-1 to 9-17, and a group represented by Formulae 10-1 to 10-12:

Formula 9-1

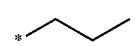

Formula 9-2

Formula 9-3

Formula 9-4

Formula 9-5

Formula 9-6

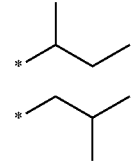

Formula 9-7

Formula 9-8

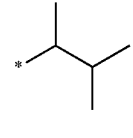

Formula 9-9

Formula 9-10

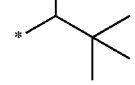

Formula 9-11

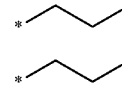

-continued

Formula 9-12
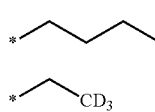

Formula 9-13
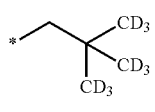

Formula 9-14
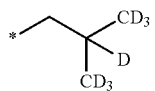

Formula 9-15
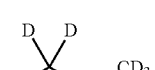

Formula 9-16

Formula 9-17
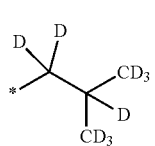

Formula 10-1
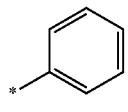

Formula 10-2
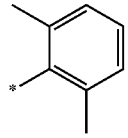

Formula 10-3
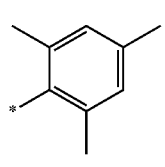

Formula 10-4
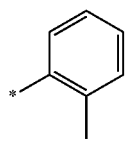

Formula 10-5
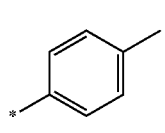

Formula 10-6
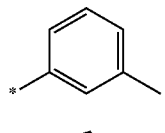

Formula 10-7
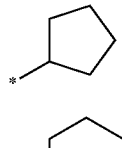

Formula 10-8
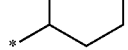

-continued

Formula 10-9
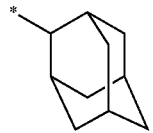

Formula 10-10
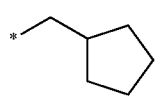

Formula 10-11
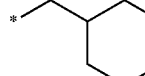

Formula 10-12
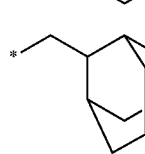

10. The organometallic compound of claim 1, wherein $R_{21}$ is selected from a hydrogen, a deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantyl group, a norbornyl group, a cyclopentenyl group, cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —$B(Q_{11})(Q_{12})$ and —$P(=O)(Q_{13})(Q_{14})$, $Q_{11}$ to $Q_{14}$ are each independently selected from a $C_1$-$C_{20}$ alkyl group, a $C_1$-$C_{20}$ alkoxy group, a phenyl group, a naphthyl group, a pyridinyl group, a pyrimidinyl group, a triazinyl group, and a carbazolyl group; and a phenyl group and a naphthyl group, each substituted with at least one selected from a $C_1$-$C_{20}$ alkyl group, a phenyl group, and a naphthyl group.

11. The organometallic compound of claim 1, wherein $R_{21}$ is selected from a hydrogen, a deuterium, a cyano group, a nitro group, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group, each substituted with at least one selected from a deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantyl group, a norbornyl group, a cyclopentenyl group, a cyclohexenyl group, a cycloheptenyl group, a phenyl group, a naphthyl group, a pyridinyl group, and a pyrimidinyl group; and —$B(Q_{11})(Q_{12})$ and —$P(=O)(Q_{13})(Q_{14})$, and $Q_{11}$ to $Q_{14}$ are each independently selected from a $C_1$-$C_{10}$ alkyl group, a $C_1$-$C_{10}$ alkoxy group, a phenyl group, and a naphthyl group; and a phenyl group and a naphthyl group, each substituted with at least one selected from a $C_1$-$C_{10}$ alkyl group, a phenyl group, and a naphthyl group.

12. The organometallic compound of claim 1, wherein $R_{21}$ is selected from a hydrogen, a deuterium, a cyano group, a nitro group, —$CH_3$, —$CD_3$, —$CD_2H$, —$CDH_2$, —$CF_3$, —$CF_2H$, —$CFH_2$, groups represented by Formulae 9-1 to 9-17, and groups represented by Formulae 10-1 to 10-30:
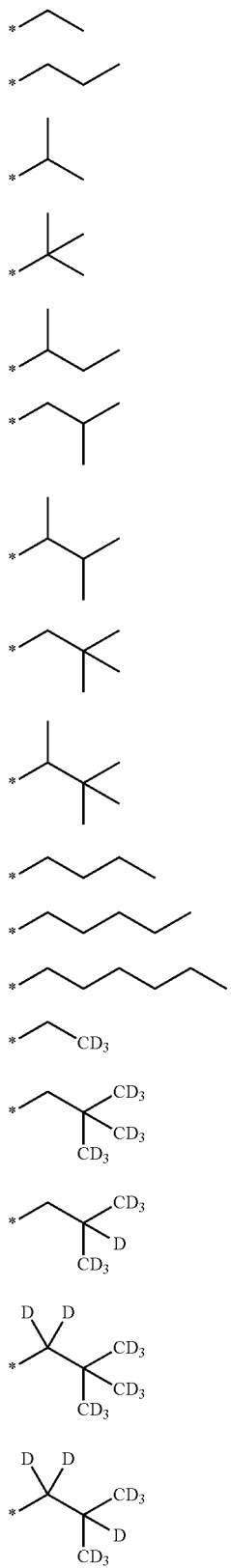
Formula 9-1
Formula 9-2
Formula 9-3
Formula 9-4
Formula 9-5
Formula 9-6
Formula 9-7
Formula 9-8
Formula 9-9
Formula 9-10
Formula 9-11
Formula 9-12
Formula 9-13
Formula 9-14
Formula 9-15
Formula 9-16
Formula 9-17
-continued
Formula 10-1
Formula 10-2
Formula 10-3
Formula 10-4
Formula 10-5
Formula 10-6
Formula 10-7
Formula 10-8
Formula 10-9
Formula 10-10
Formula 10-11
Formula 10-12

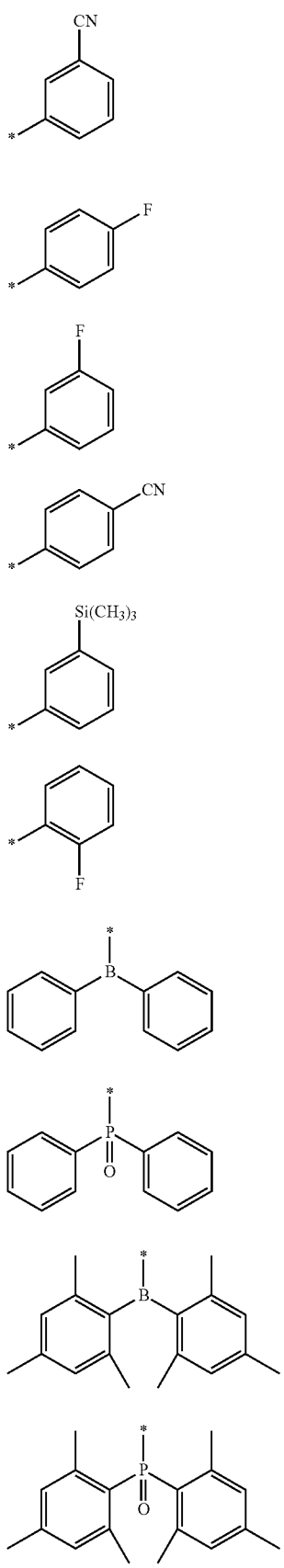
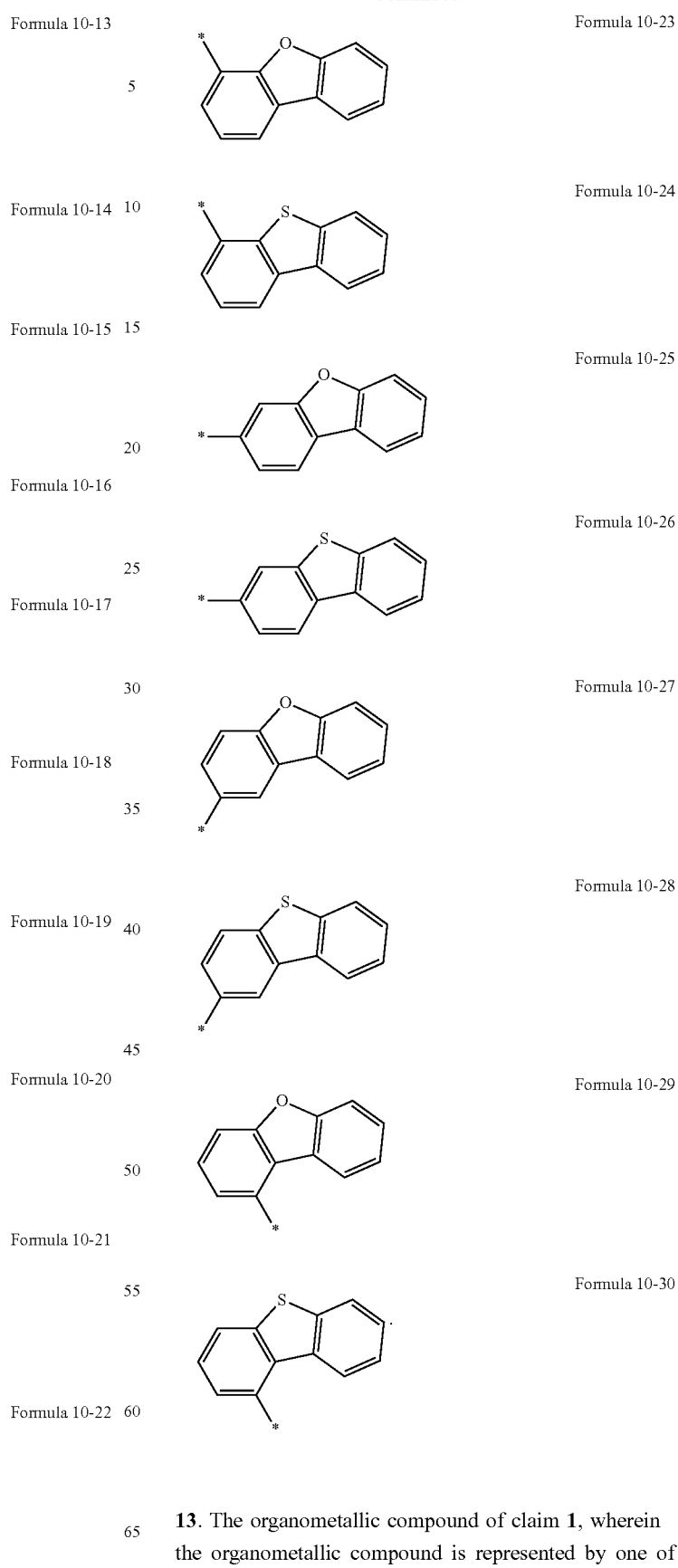
13. The organometallic compound of claim 1, wherein the organometallic compound is represented by one of Formulae 1-1 to 1-12:

Formula 1-1
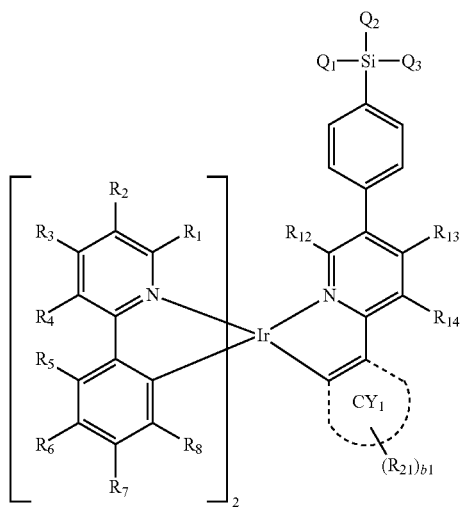
Formula 1-2
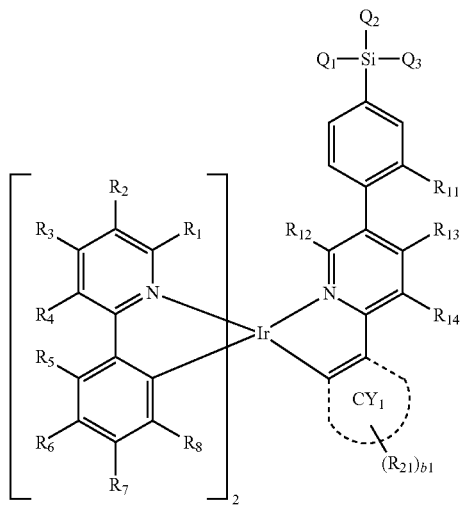
Formula 1-3
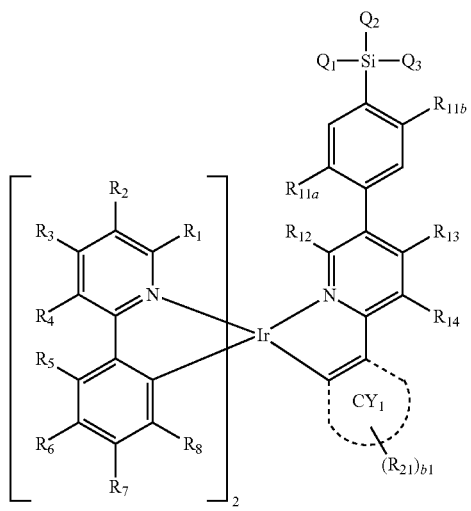
Formula 1-4
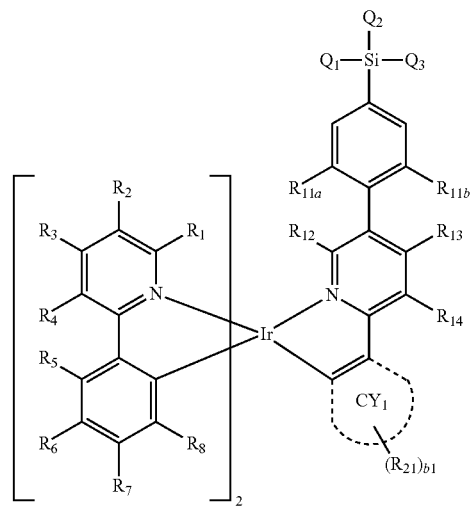
Formula 1-5
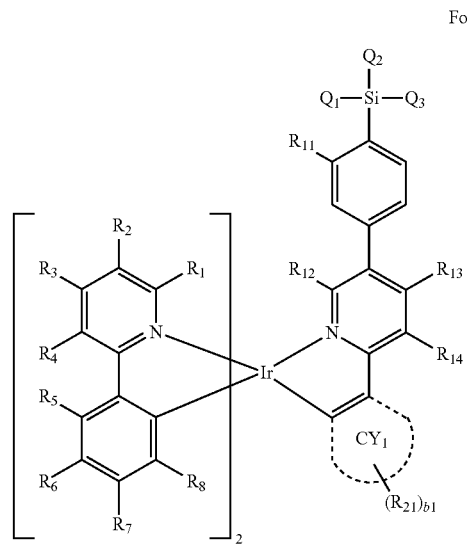
Formula 1-6
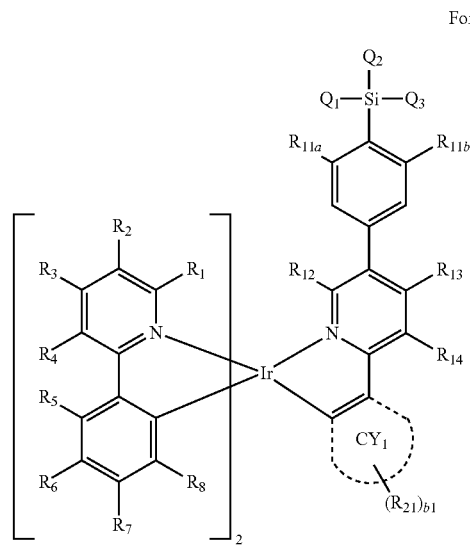

Formula 1-7
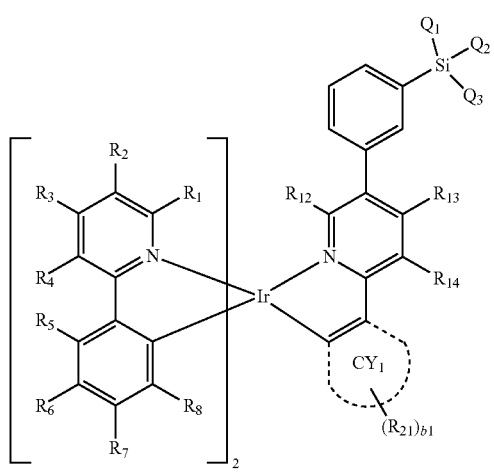
Formula 1-8
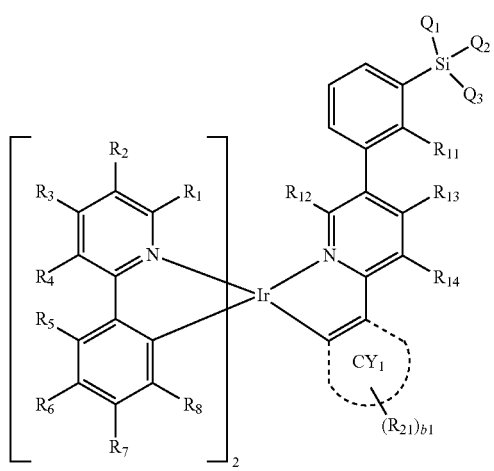
Formula 1-9
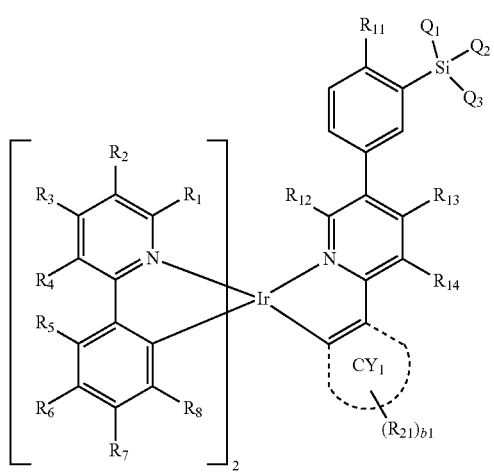
Formula 1-10
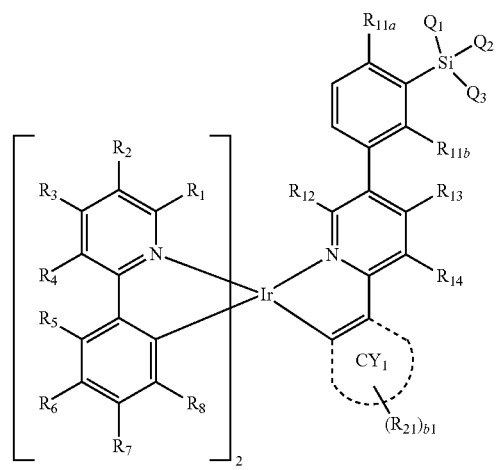
Formula 1-11
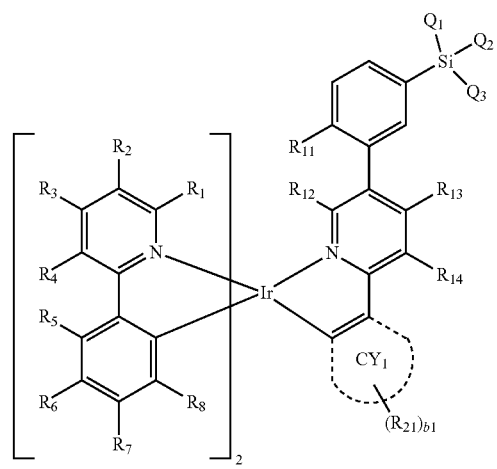
Formula 1-12
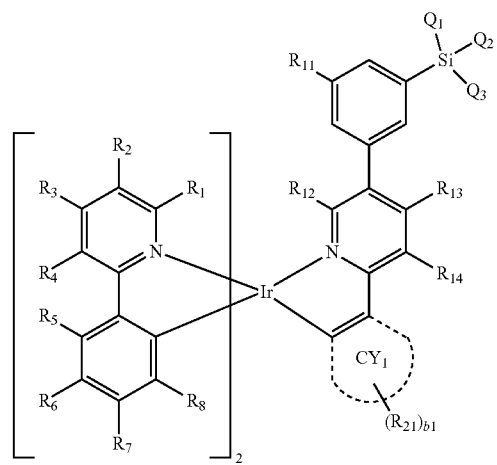
wherein in Formulae 1-1 to 1-12, $CY_1$, $Q_1$ to $Q_3$, $R_1$ to $R_8$, $R_{11}$ to $R_{14}$, $R_{21}$, and b1 are the same as in claim 1, and $R_{11a}$ and $R_{11b}$ are the same as $R_{11}$, provided that each of $R_{11}$, $R_{11a}$, and $R_{11b}$ in Formulae 1-1 to 1-12 is not a hydrogen.
14. The organometallic compound of claim 1, wherein the organometallic compound is represented by one of Formulae 1(1) to 1(12):

Formula 1(1)
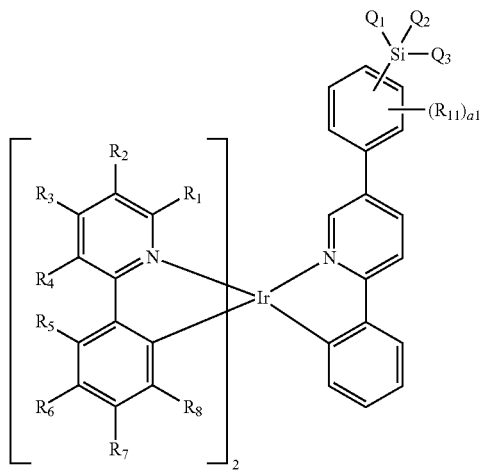
Formula 1(2)
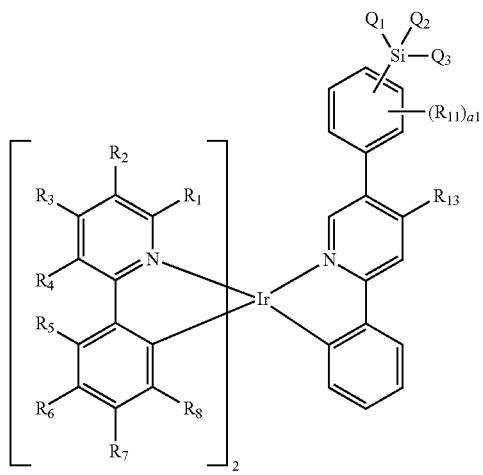
Formula 1(3)
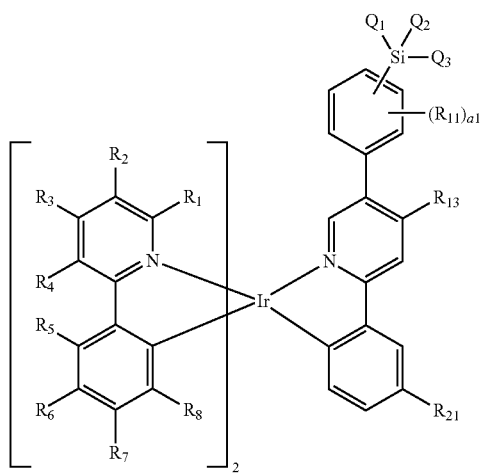
Formula 1(4)
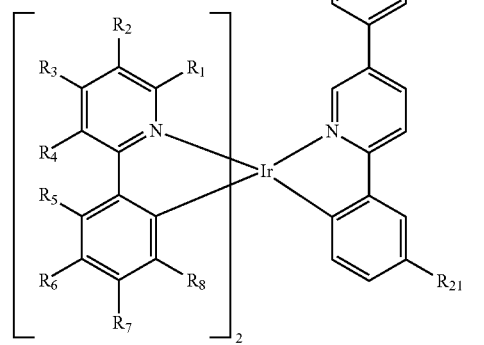
Formula 1(5)
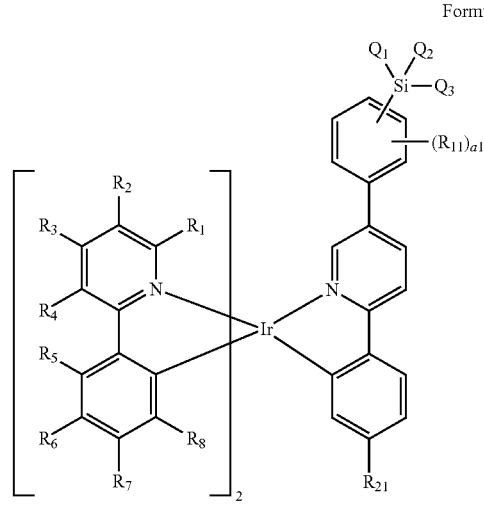
Formula 1(6)
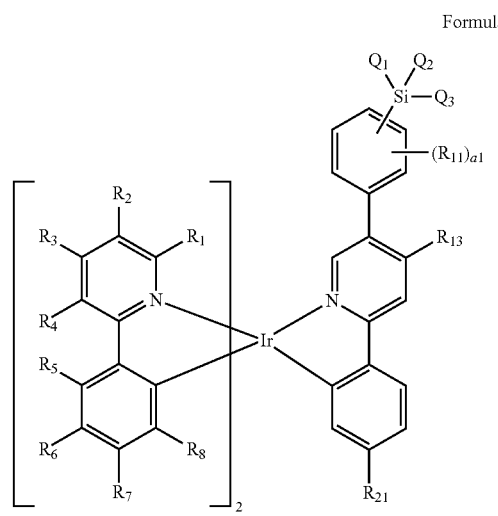

Formula 1(7)
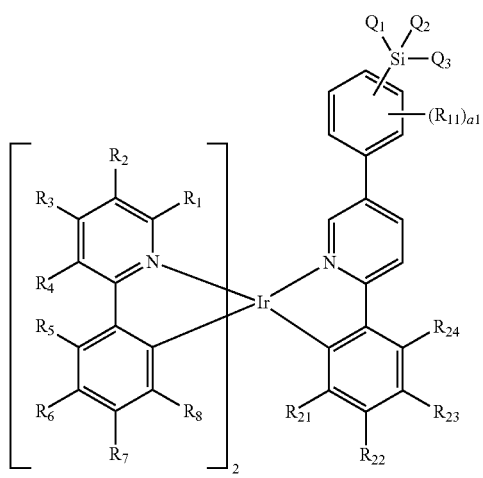
Formula 1(8)
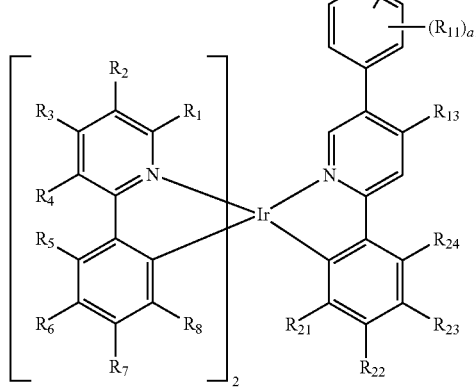
Formula 1(9)
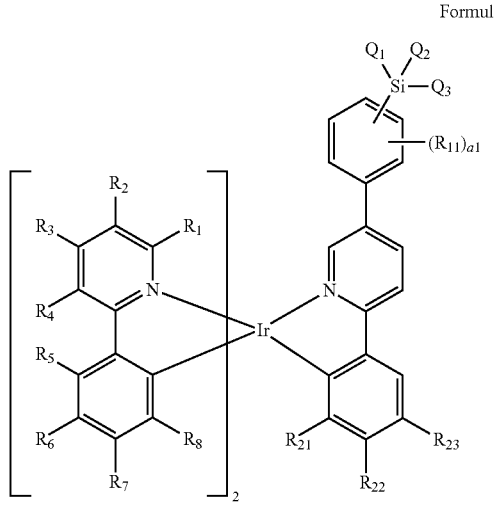
Formula 1(10)
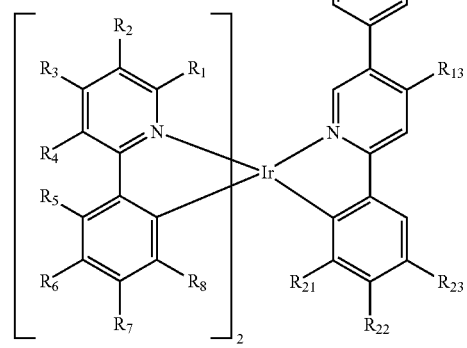
Formula 1(11)
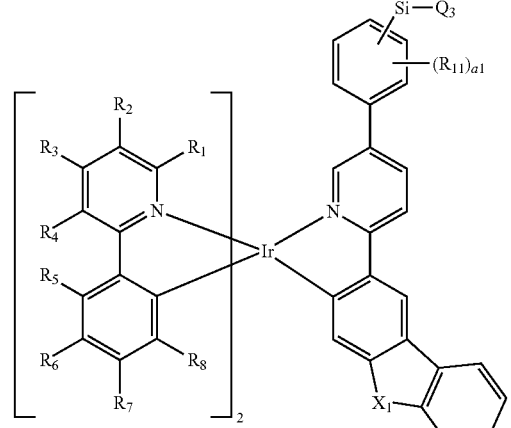
Formula 1(12)
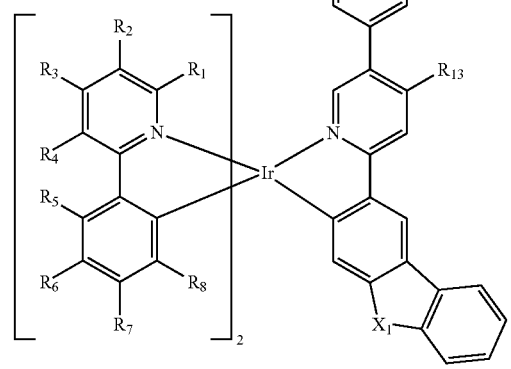
wherein in Formulae 1(1) to 1(12), $Q_1$ to $Q_3$, $R_1$ to $R_8$, $R_{11}$, a1, $R_{13}$ and $R_{21}$ are the same as in claim 1, $X_1$ is $N(R_{21})$, O, or S, and $R_{22}$ to $R_{24}$ are the same as $R_{21}$, provided that each of $R_{13}$ and $R_{21}$ to $R_{24}$ in Formulae 1(1) to 1(12) is not a hydrogen.

15. The organometallic compound of claim 1, wherein the organometallic compound is represented by one of Formulae 2-1 to 2-72:
Formula 2-1
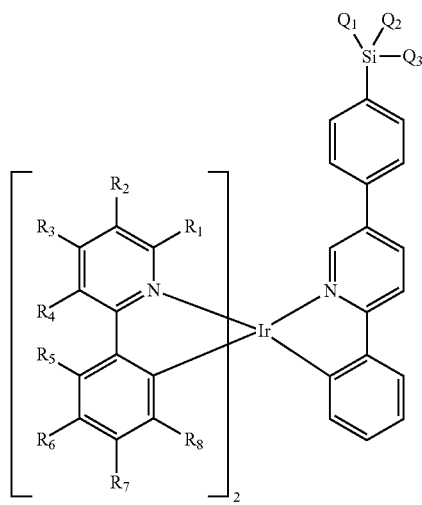
Formula 2-2
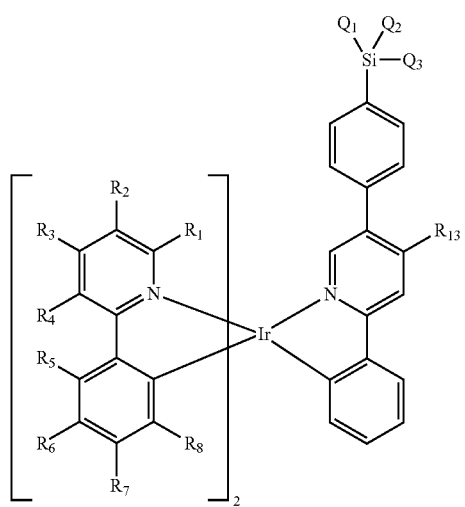
Formula 2-3
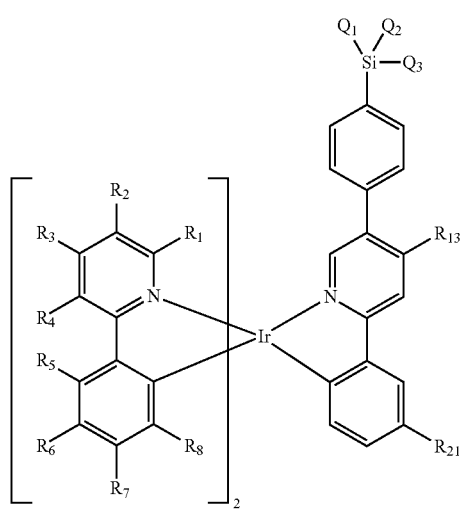
Formula 2-4
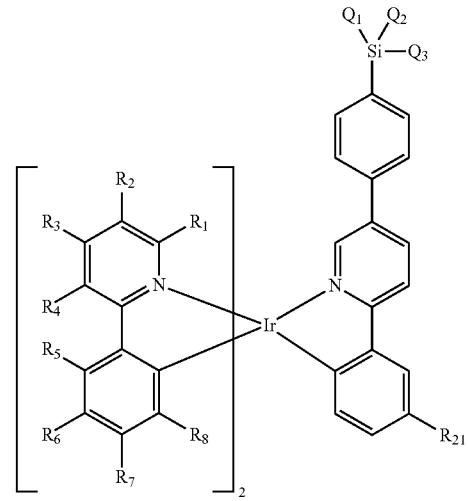
Formula 2-5
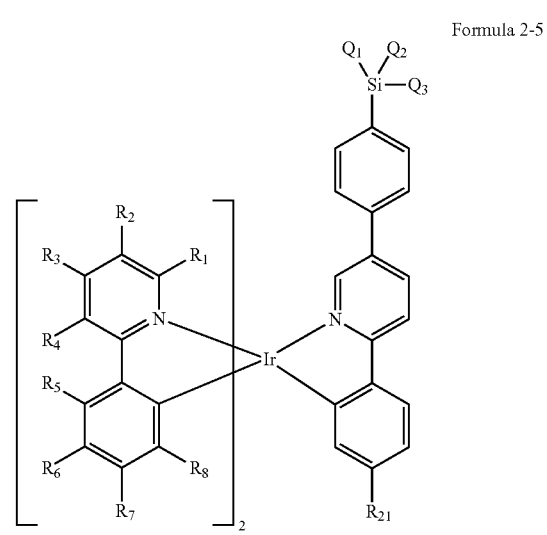
Formula 2-6
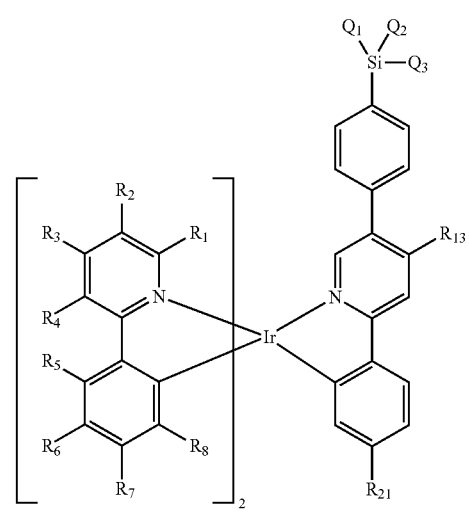

Formula 2-7
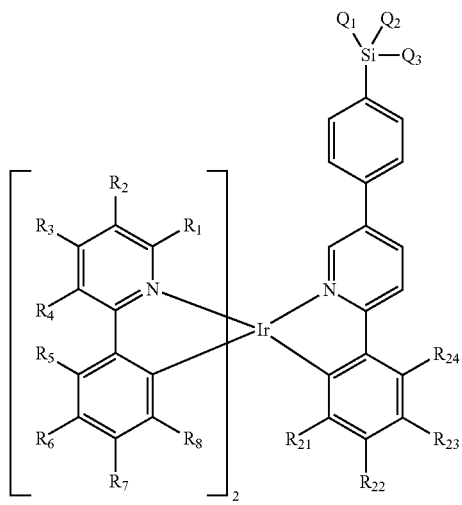
Formula 2-8
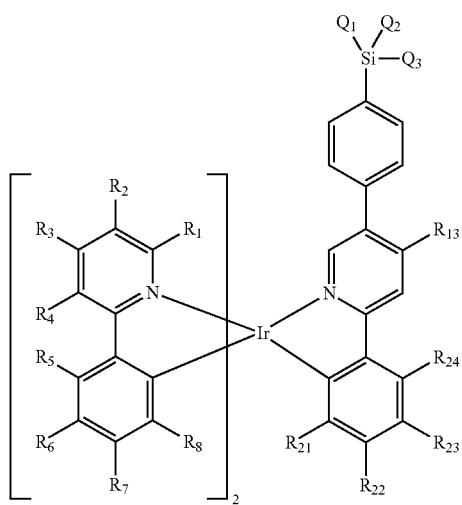
Formula 2-9
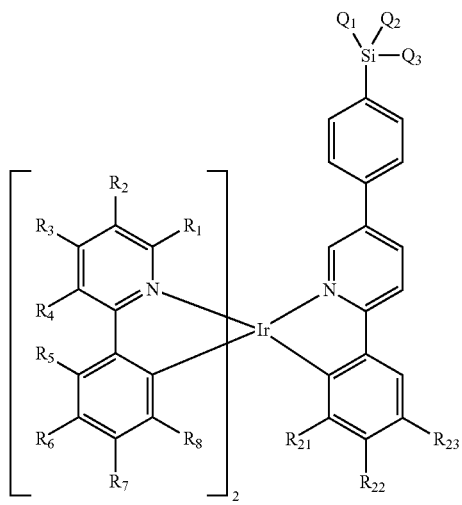
Formula 2-10
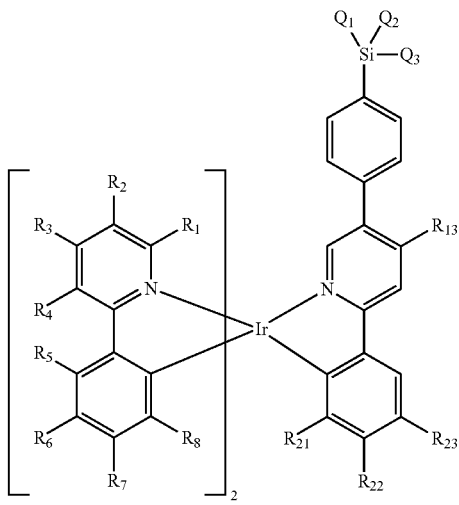
Formula 2-11
Formula 2-12
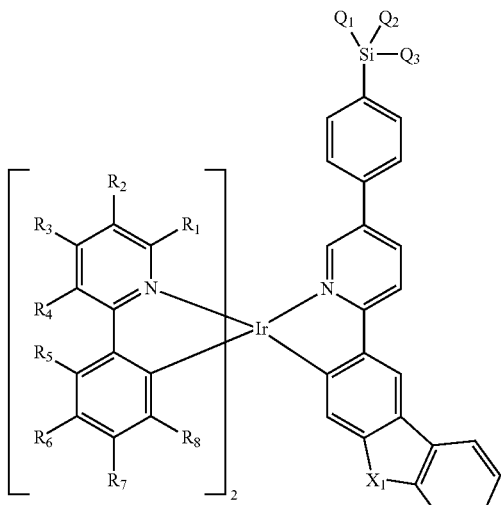

Formula 2-13
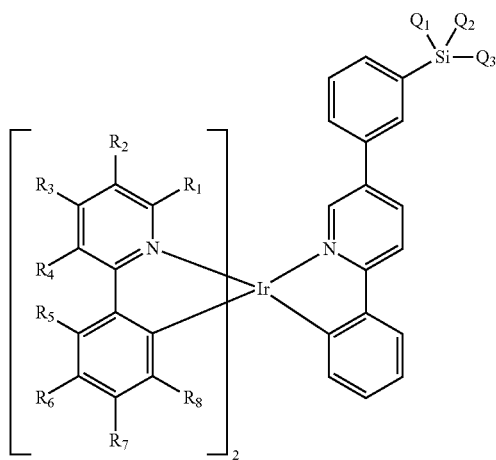
Formula 2-14
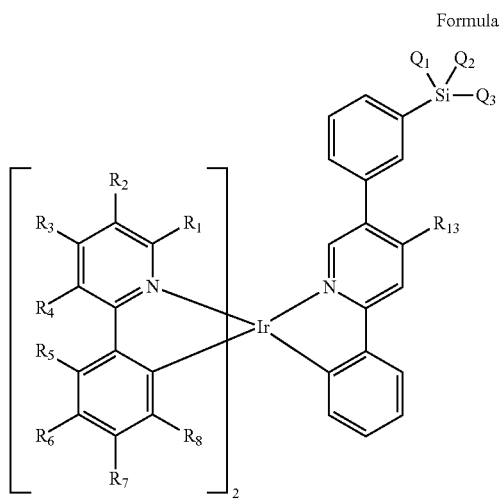
Formula 2-15
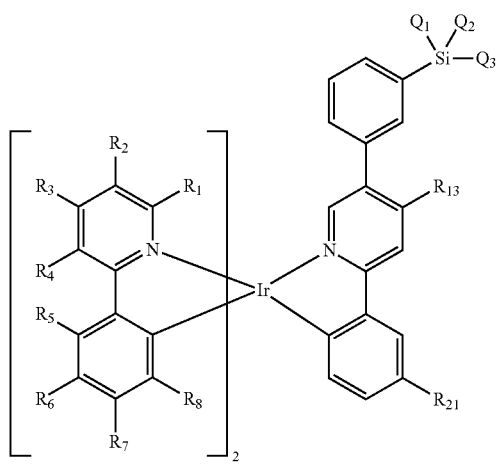
Formula 2-16
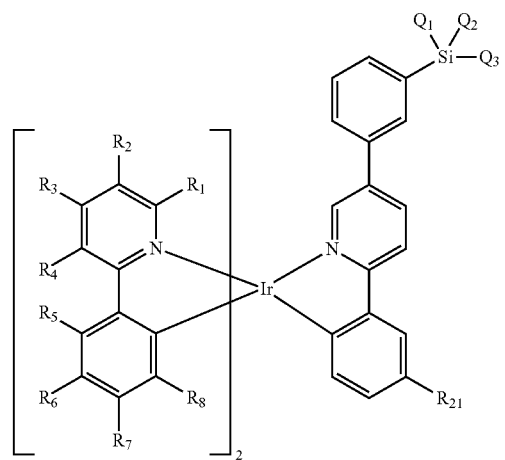
Formula 2-17
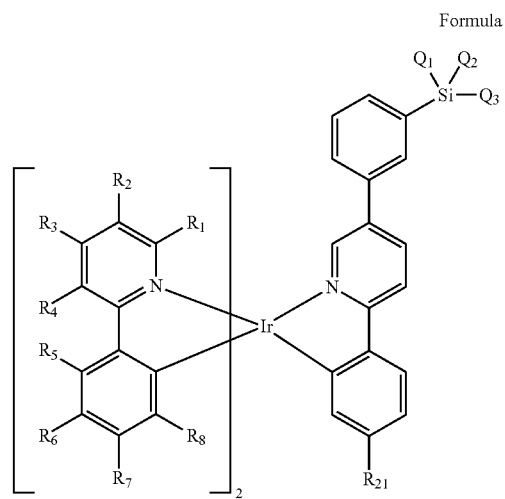
Formula 2-18
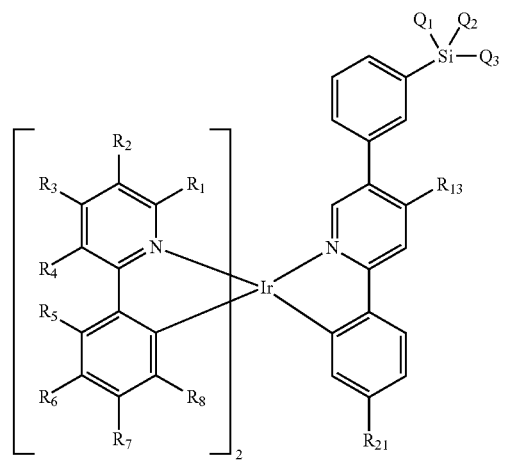

Formula 2-19
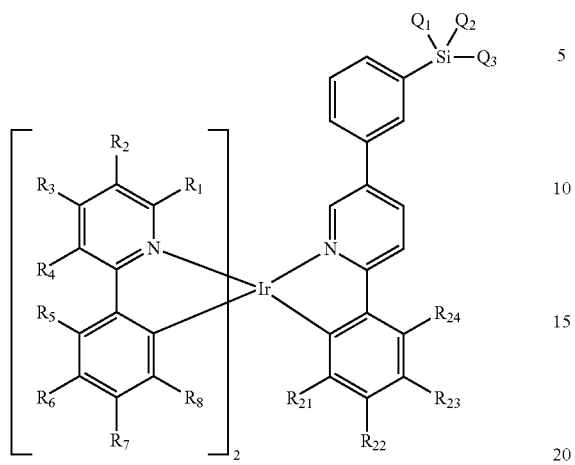
Formula 2-22
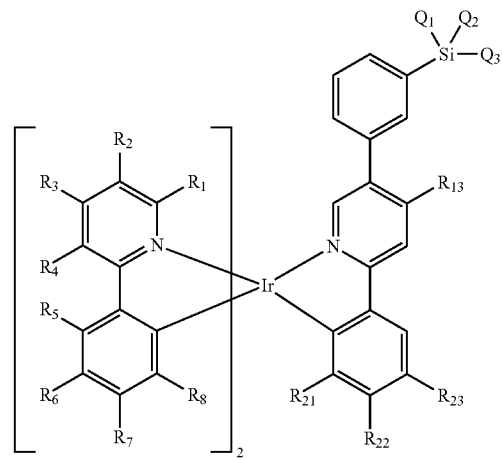
Formula 2-20
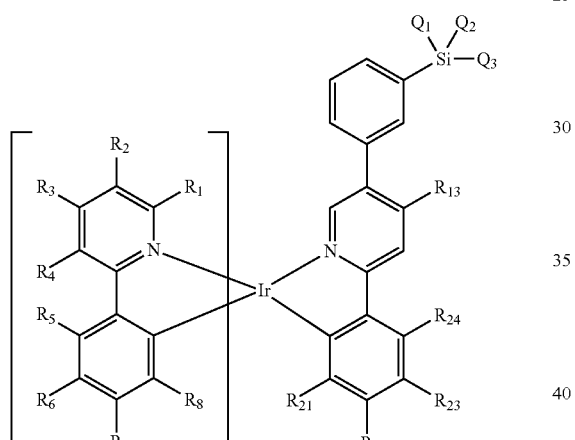
Formula 2-23
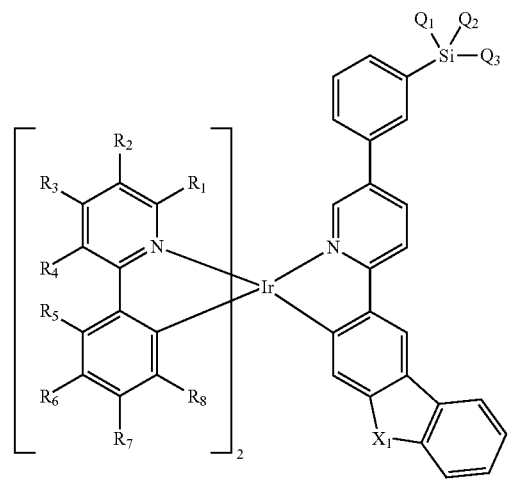
Formula 2-21
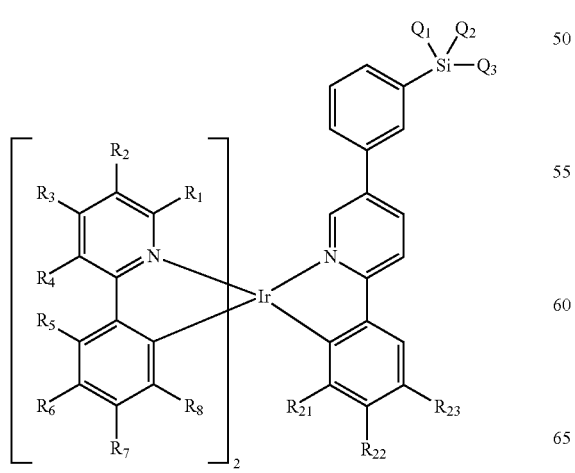
Formula 2-24
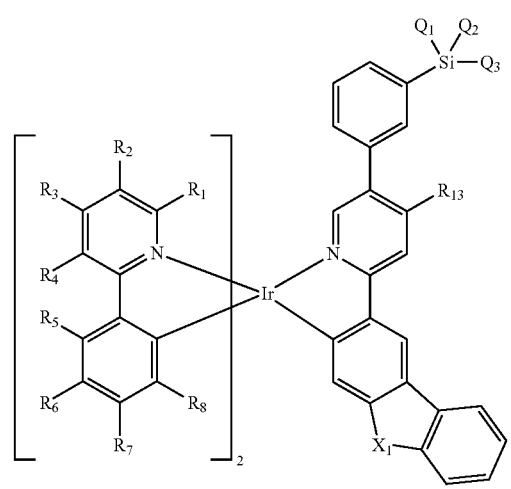

Formula 2-25
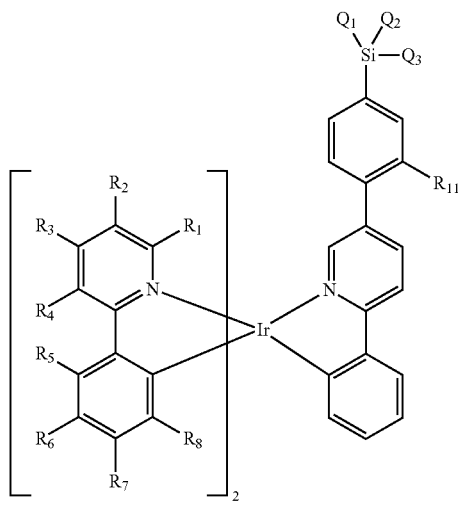
Formula 2-26
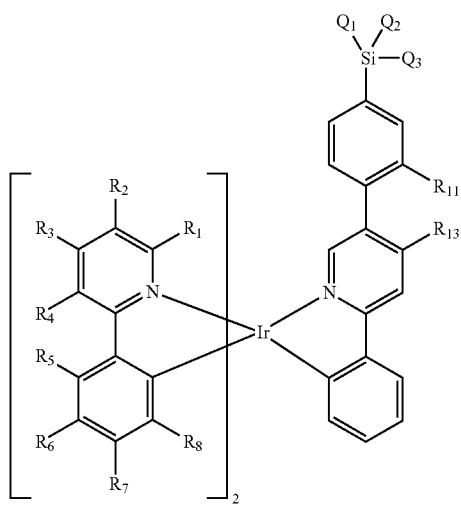
Formula 2-27
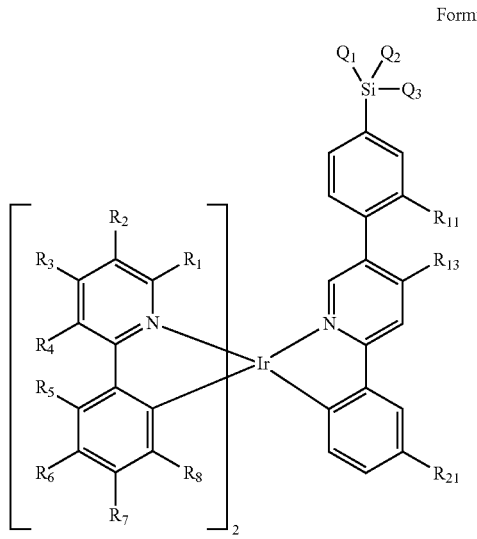
Formula 2-28
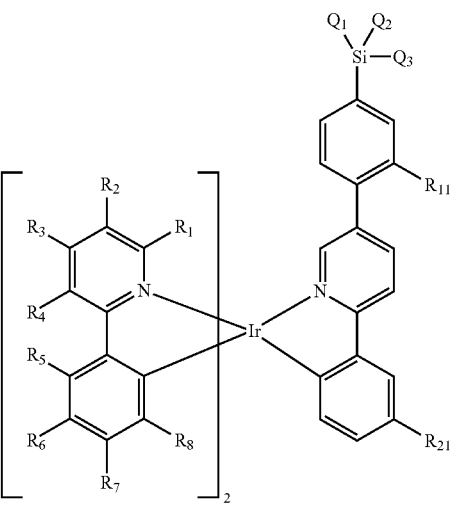
Formula 2-29
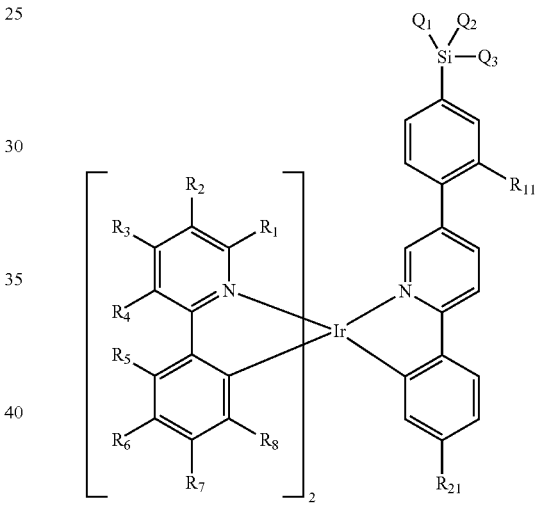
Formula 2-30
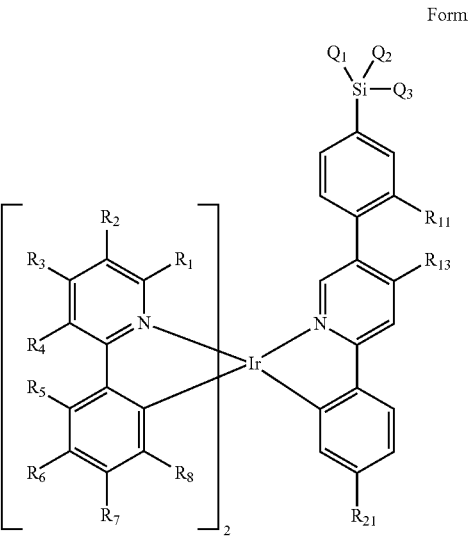

Formula 2-31
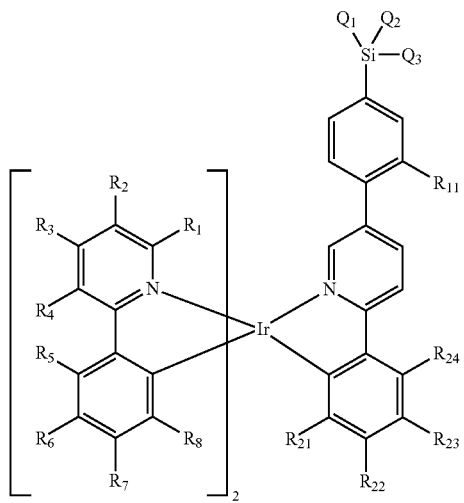
Formula 2-32
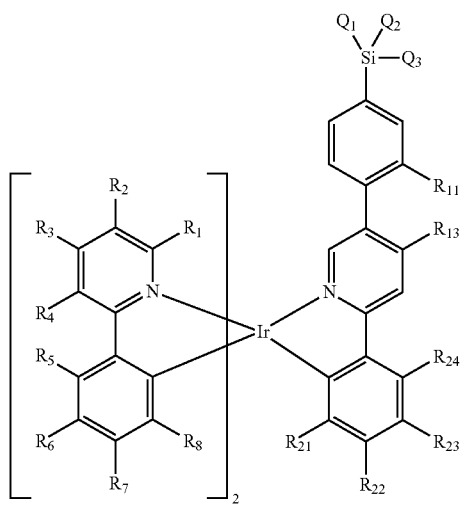
Formula 2-33
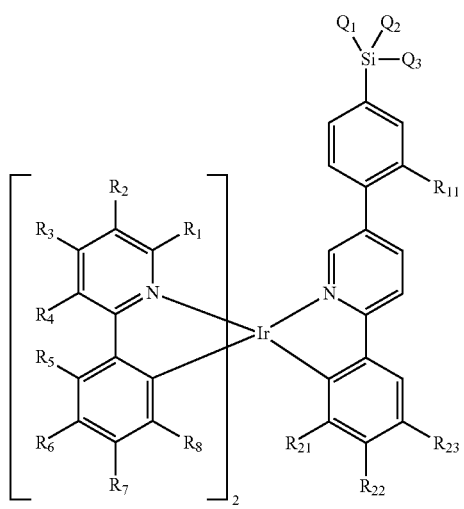
Formula 2-34
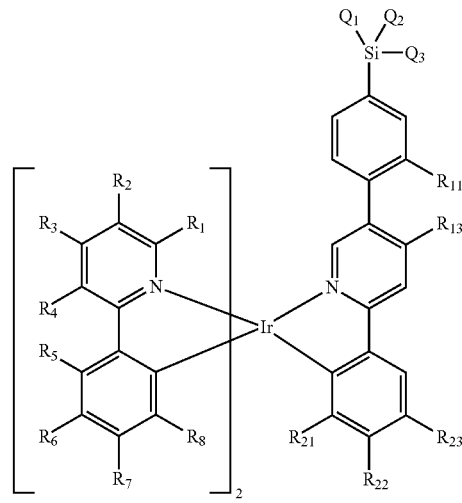
Formula 2-35
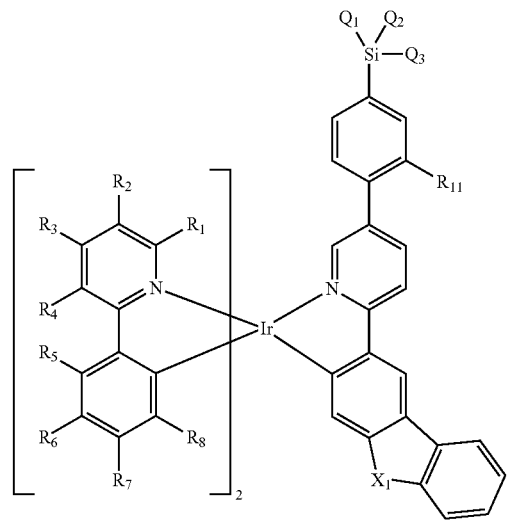
Formula 2-36
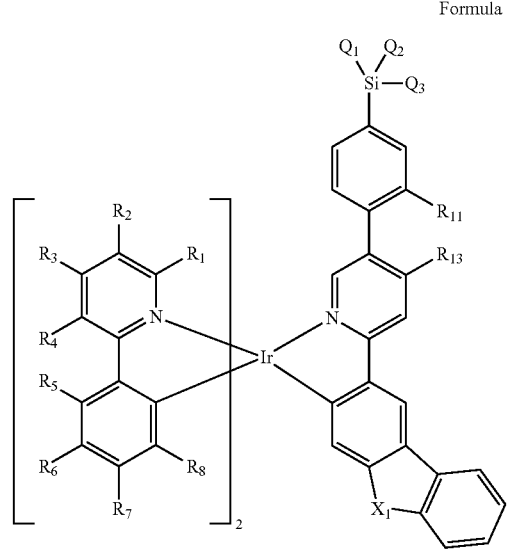

Formula 2-37
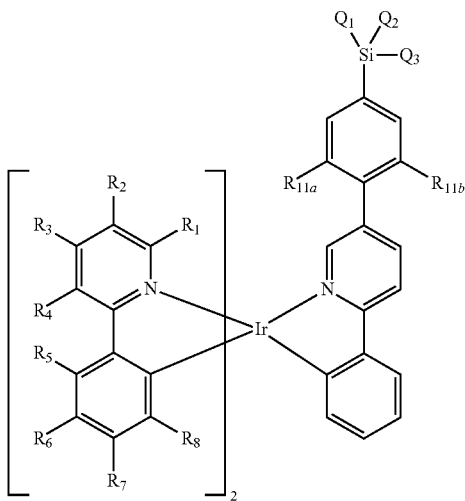
Formula 2-38
Formula 2-39
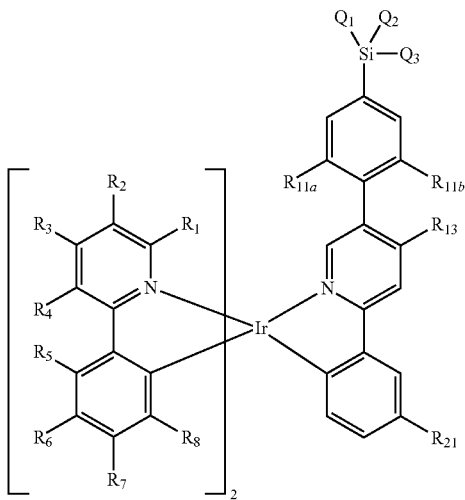
Formula 2-40
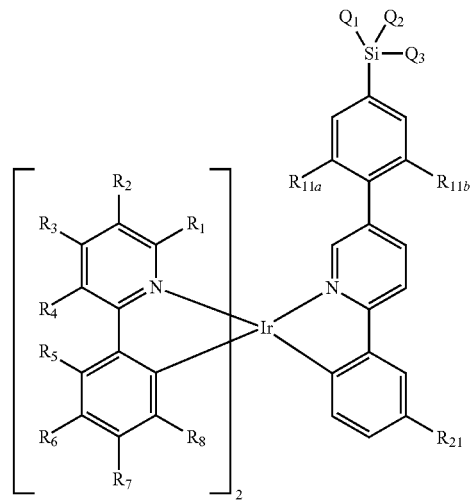
Formula 2-41
Formula 2-42

Formula 2-43
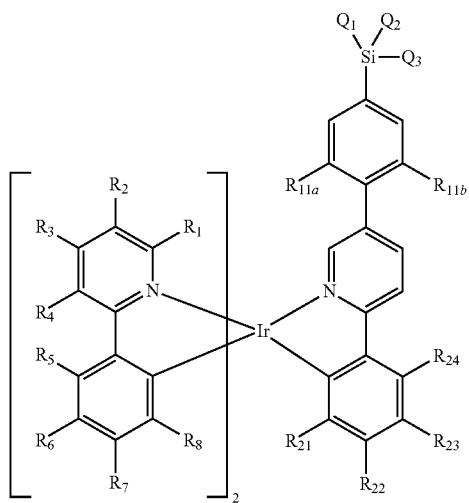
Formula 2-44
Formula 2-45
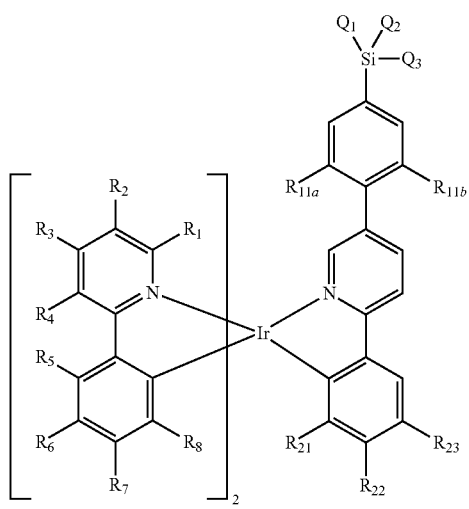
Formula 2-46
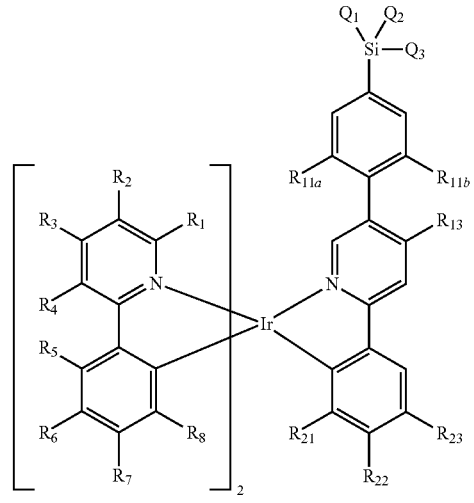
Formula 2-47
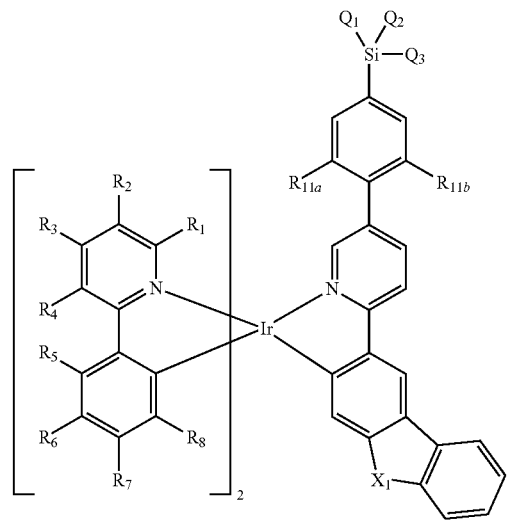
Formula 2-48
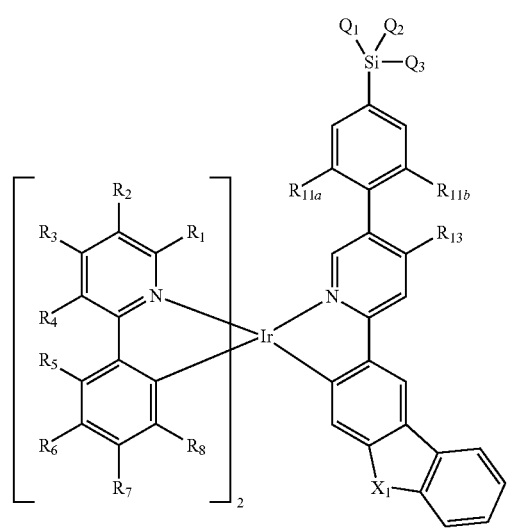

Formula 2-49
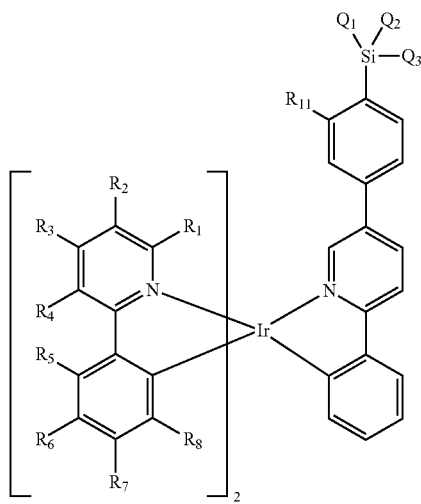
Formula 2-52
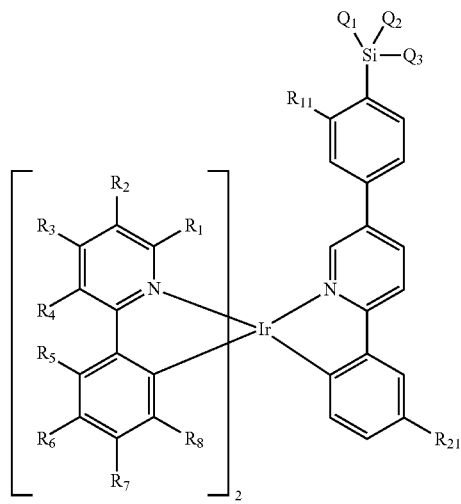
Formula 2-50
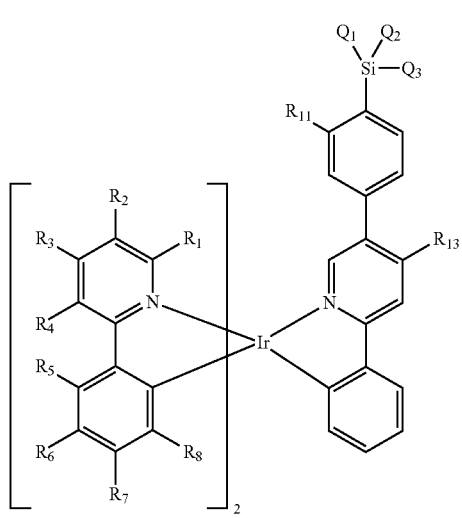
Formula 2-53
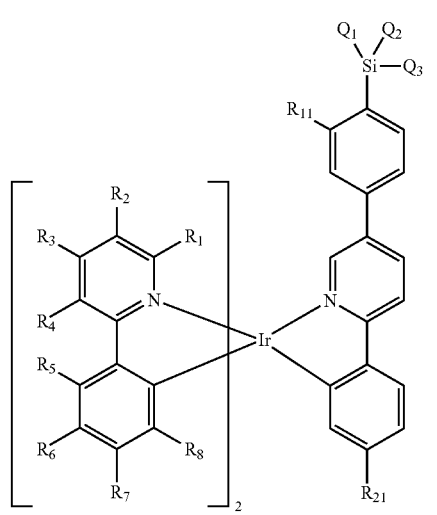
Formula 2-51
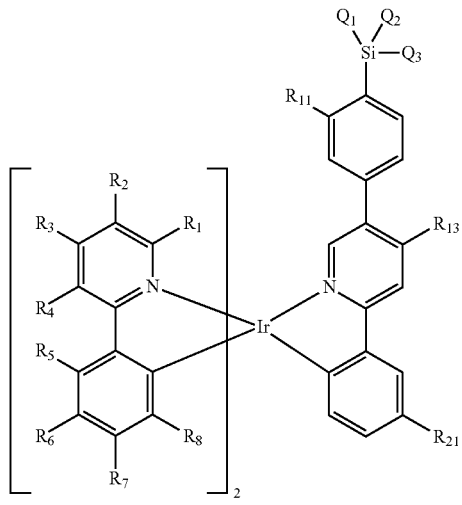
Formula 2-54
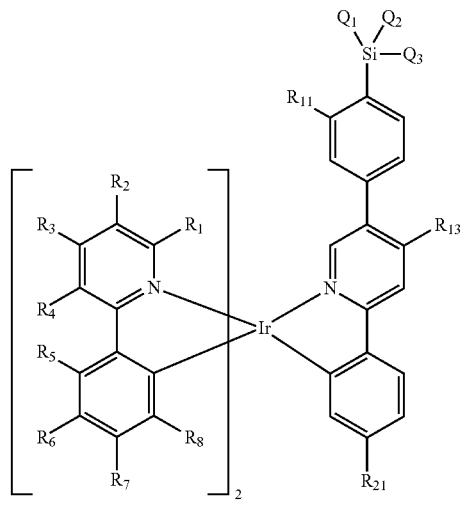

-continued
Formula 2-55
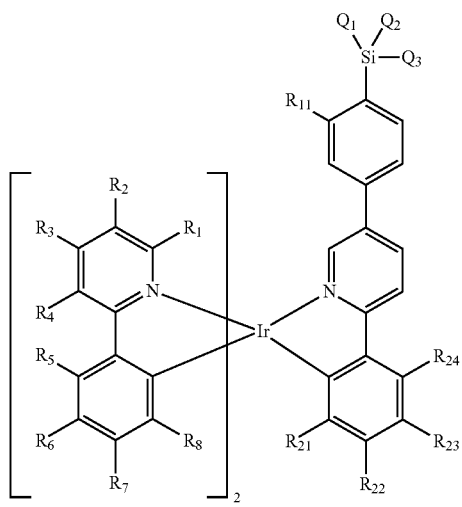
Formula 2-56
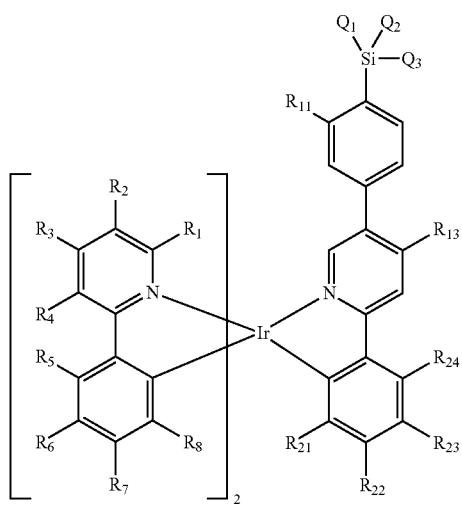
Formula 2-57
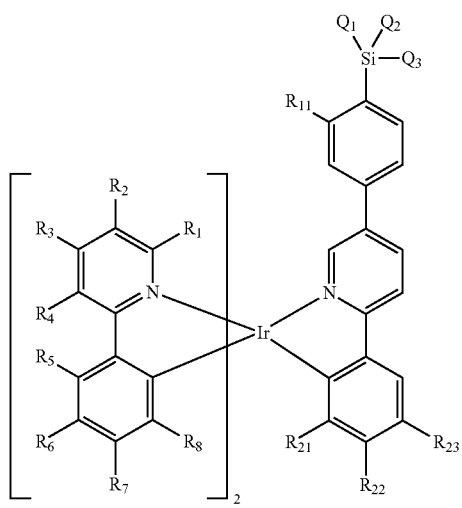
Formula 2-58
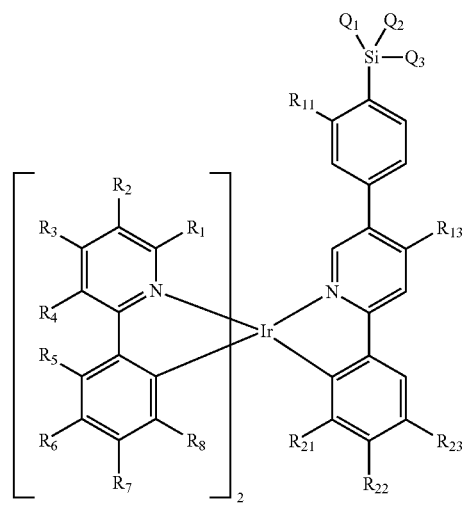
Formula 2-59
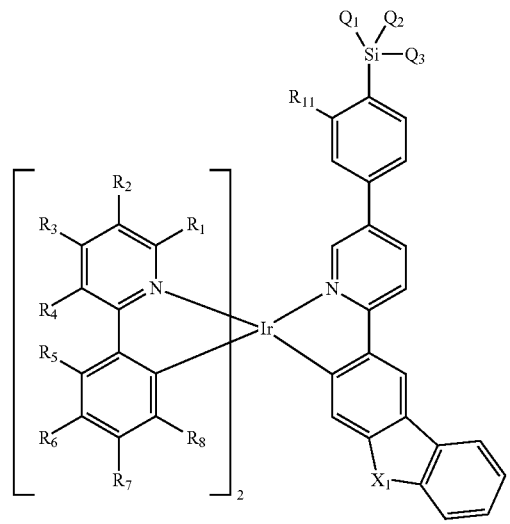
Formula 2-60
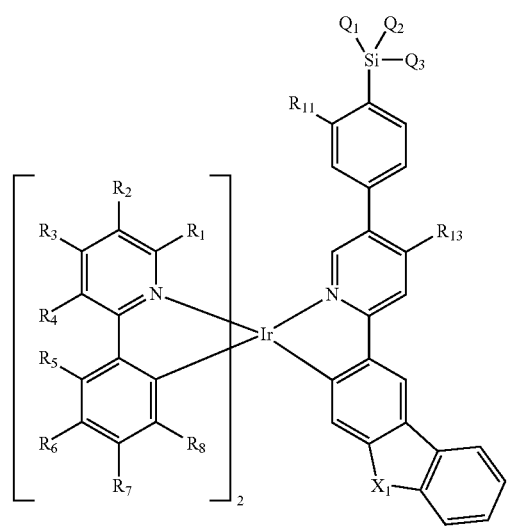

Formula 2-61
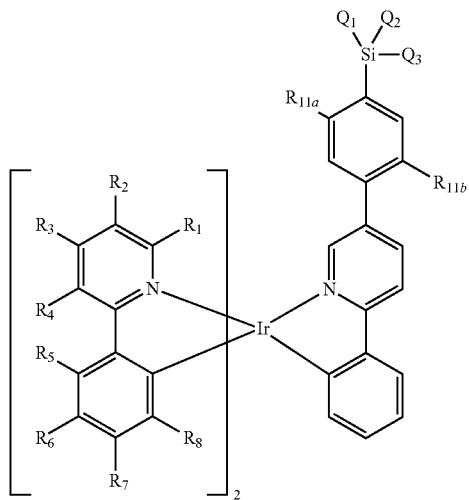
Formula 2-64
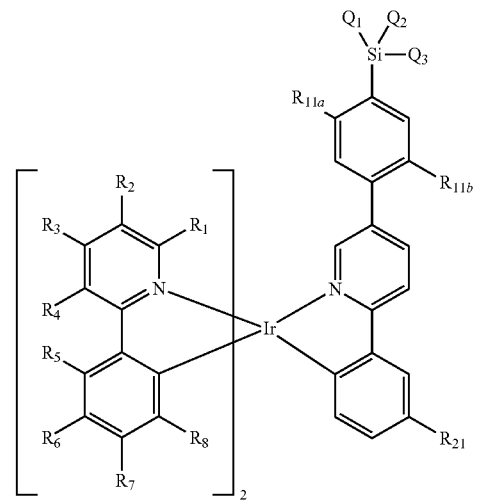
Formula 2-62
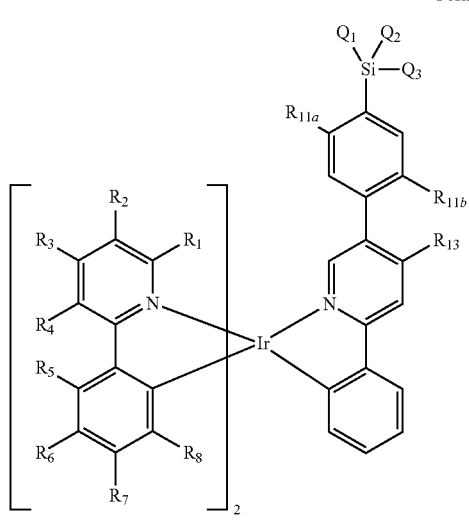
Formula 2-65
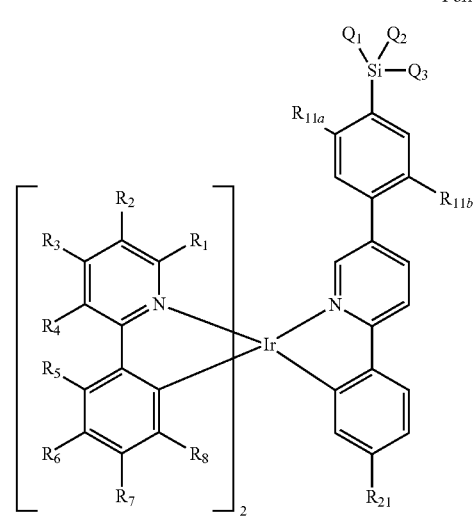
Formula 2-63
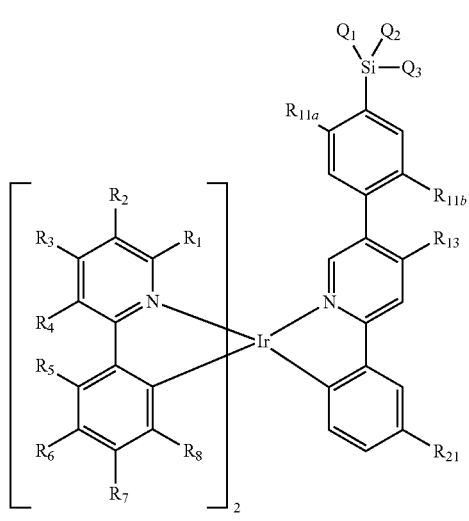
Formula 2-66
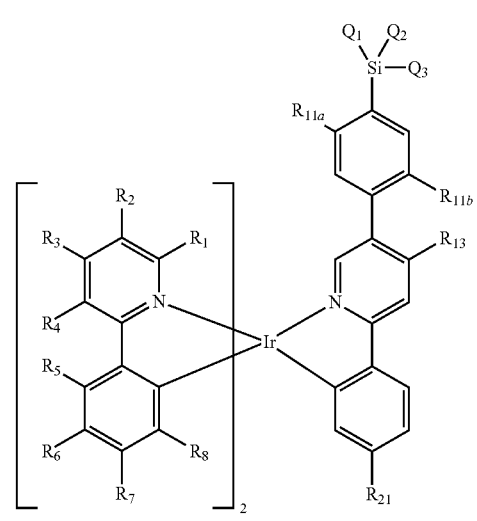

Formula 2-67
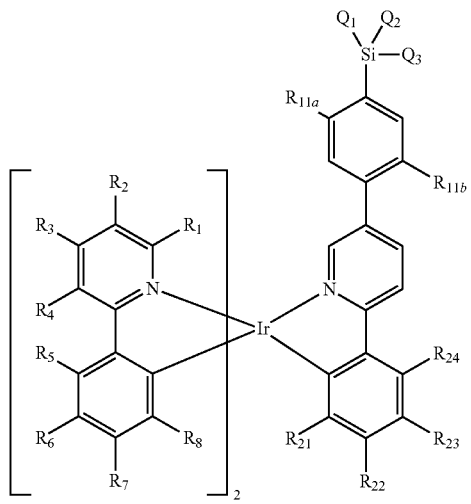
Formula 2-68
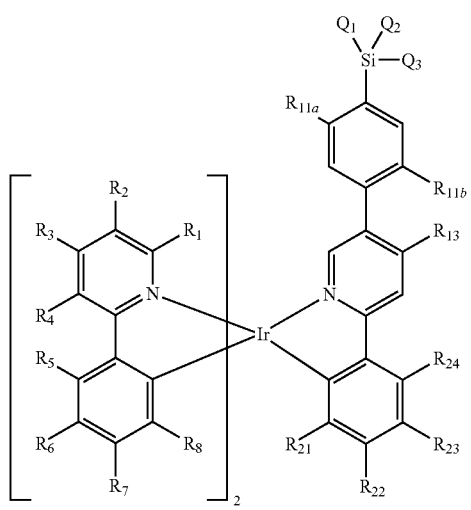
Formula 2-69
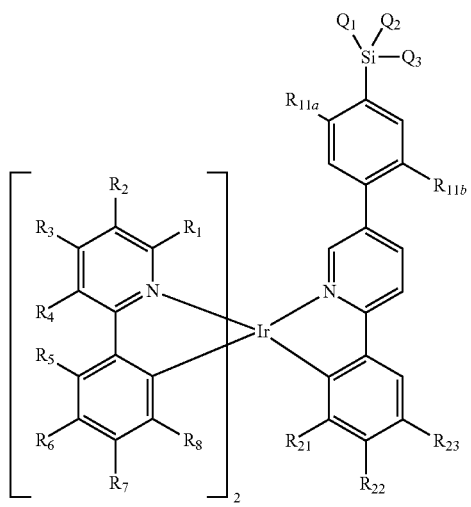
Formula 2-70
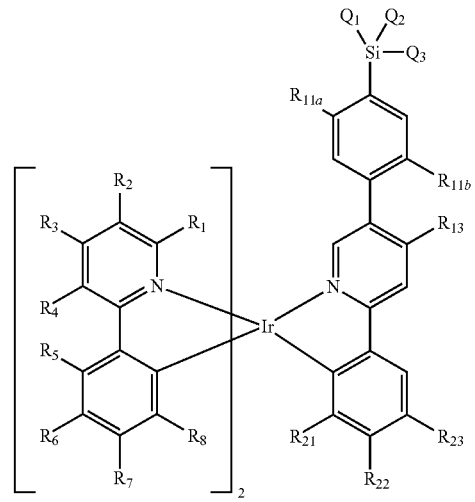
Formula 2-71
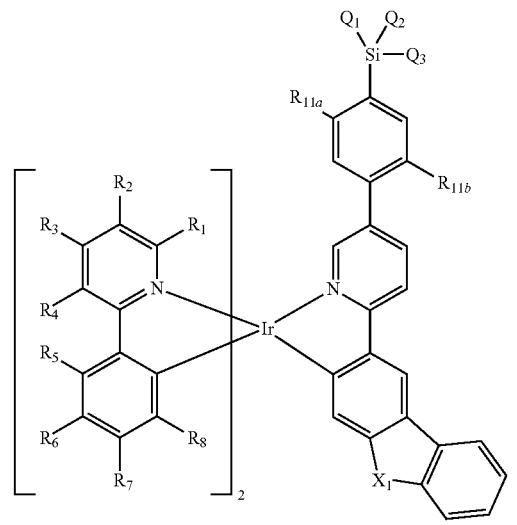
Formula 2-72
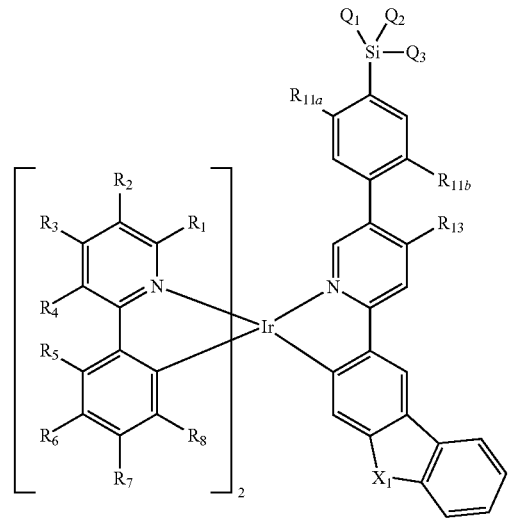
wherein in with Formulae 2-1 to 2-72, $Q_1$ to $Q_3$, $R_1$ to $R_8$, $R_{11}$, $R_{13}$, and $R_{21}$ are the same as in claim 1, $X_1$ is N($R_{21}$), O, or S, $R_{11a}$ and $R_{11b}$ are the same as $R_{11}$, and $R_{22}$ to $R_{24}$ are the same as $R_{21}$, provided that, each of $R_{11}$, $R_{11a}$, $R_{11b}$, $R_{13}$ and $R_{21}$ to $R_{24}$ in Formulae 2-1 to 2-72 is not a hydrogen.
16. The organometallic compound of claim 1, wherein the organometallic compound is one of Compounds 1 to 54:
1
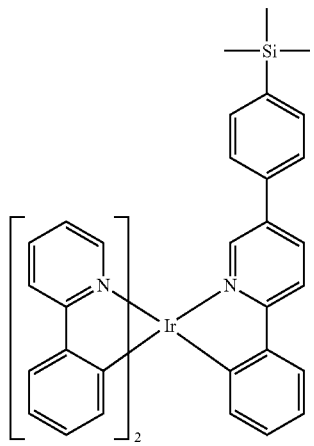
2
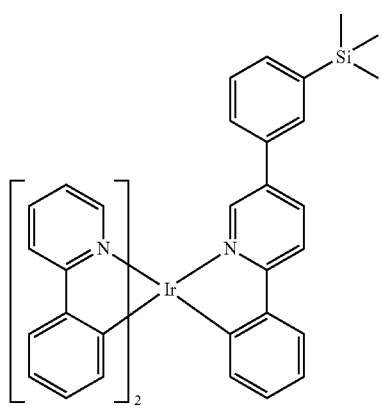
3
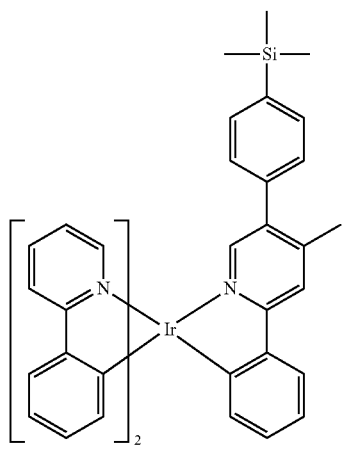
4
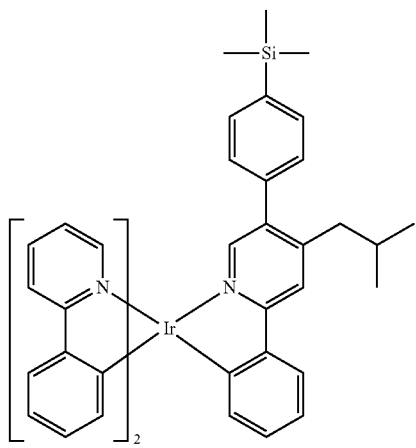
5
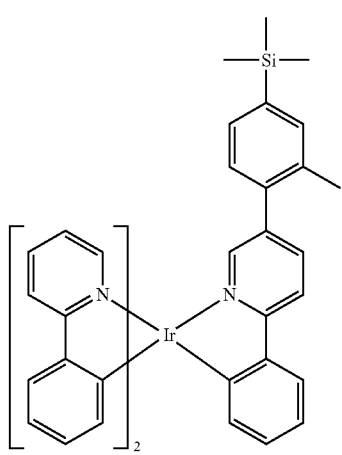
6
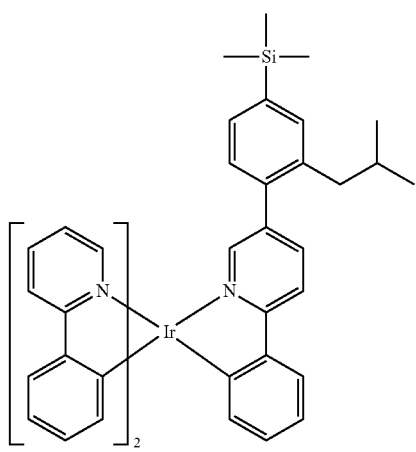

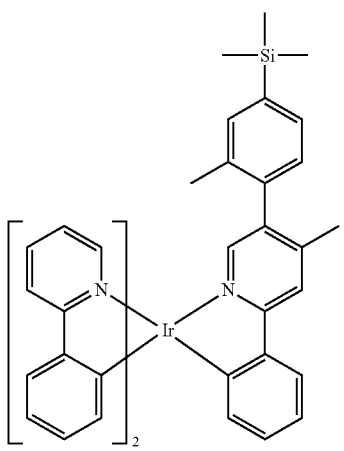
7
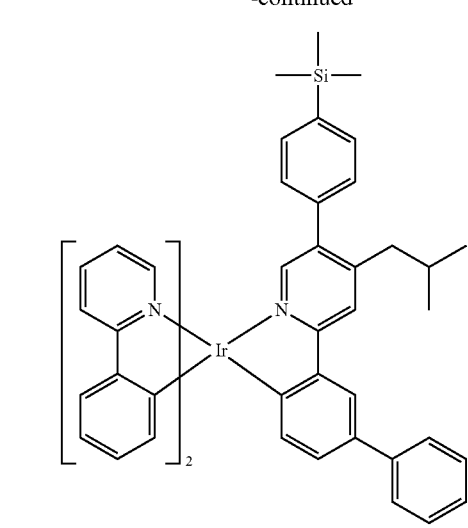
10
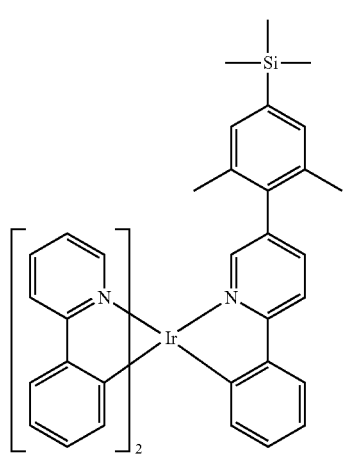
8
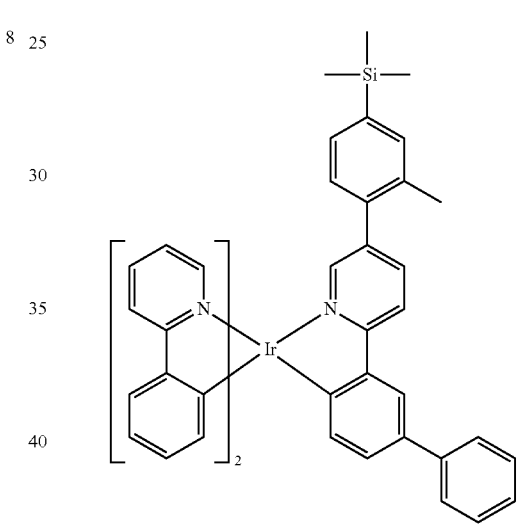
11
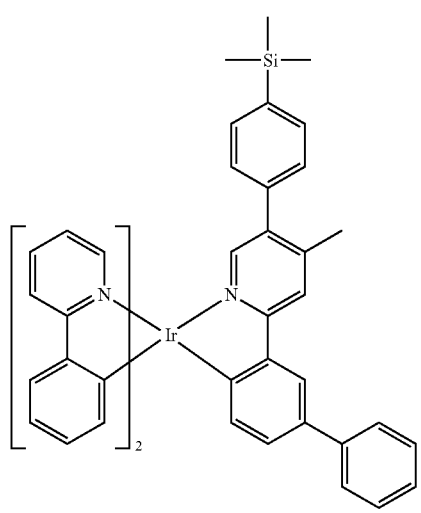
9
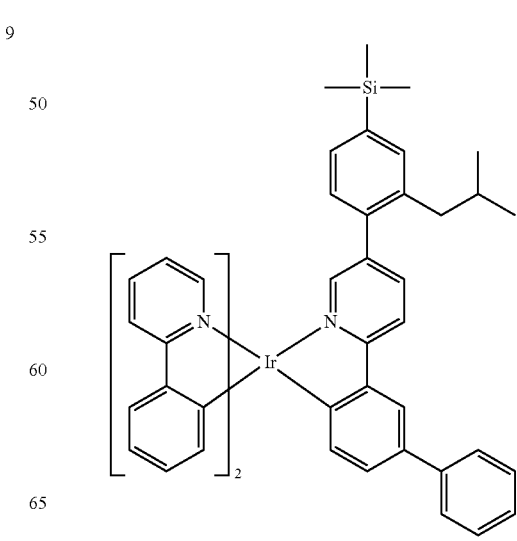
12

13
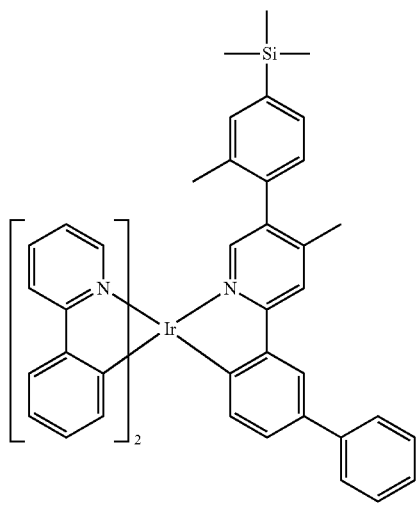
14
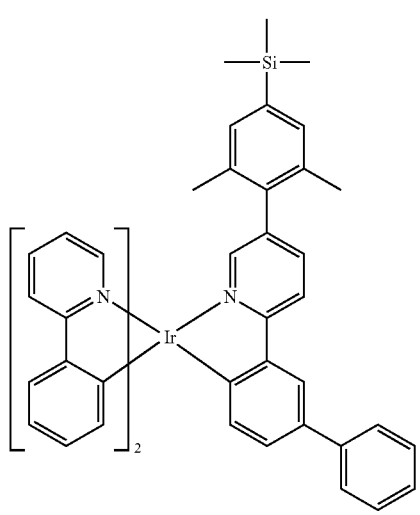
15
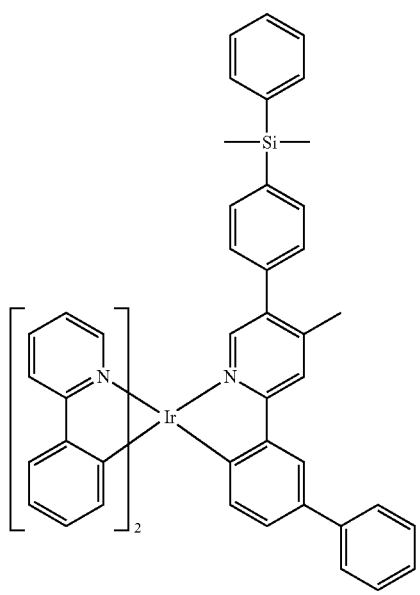
16
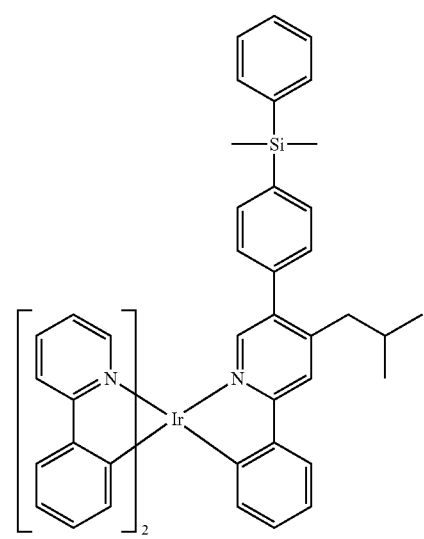
17
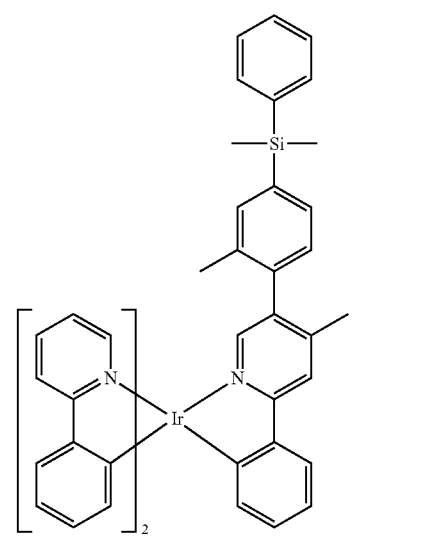
18
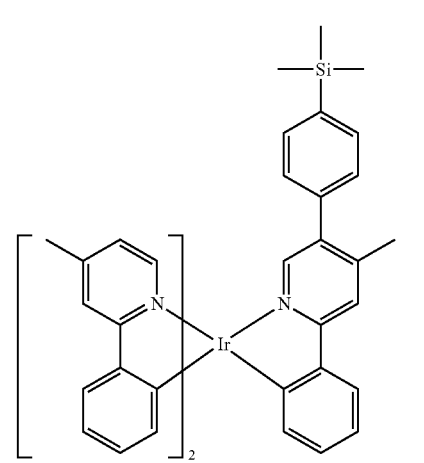

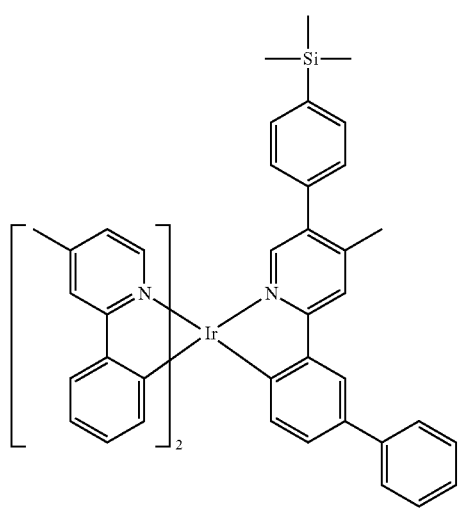
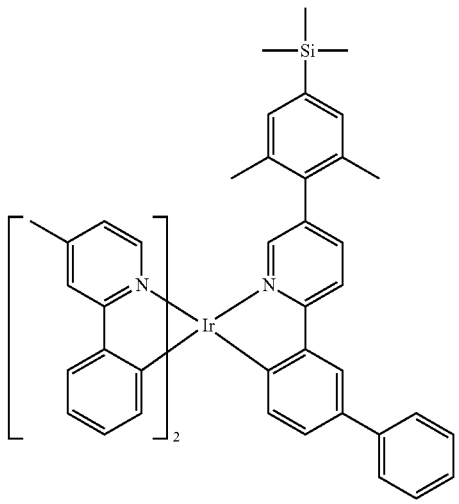

25
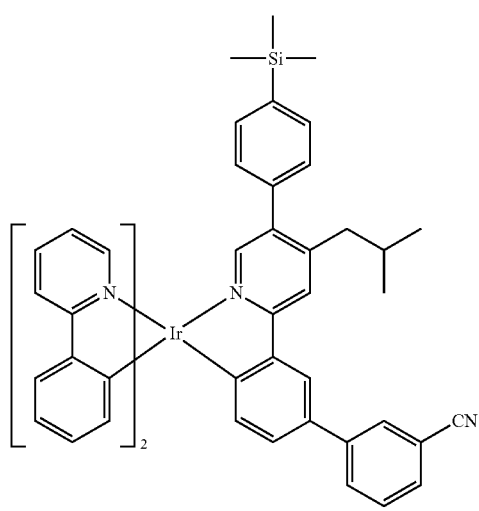
28
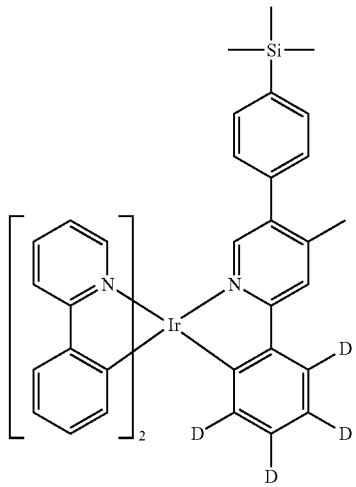
26
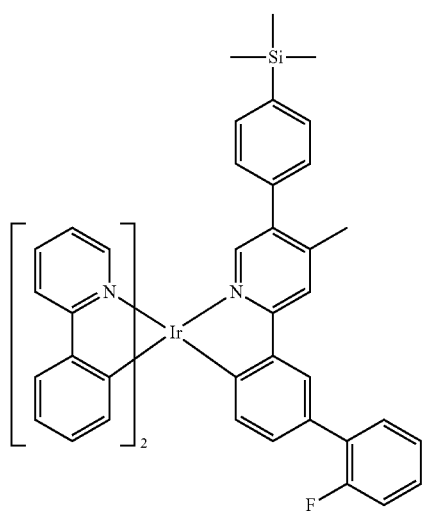
29
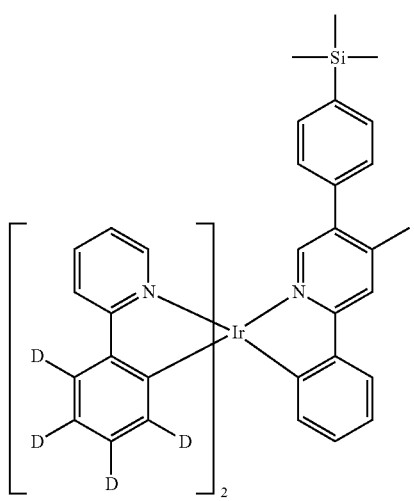
27
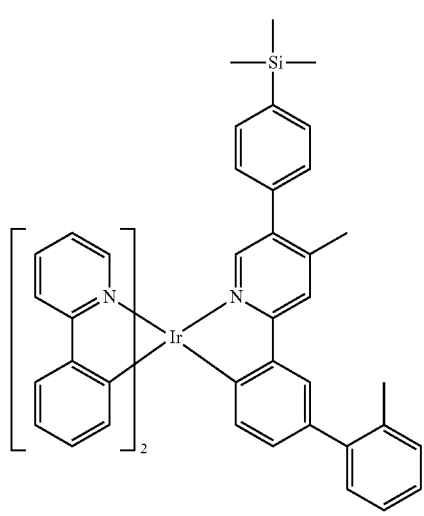
30
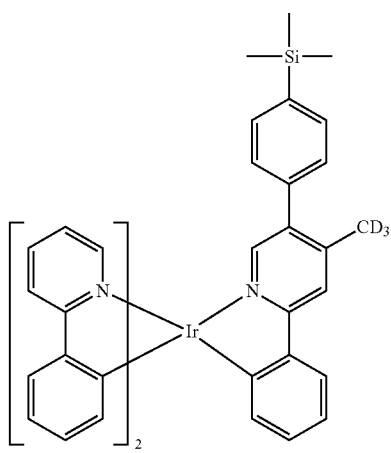

31
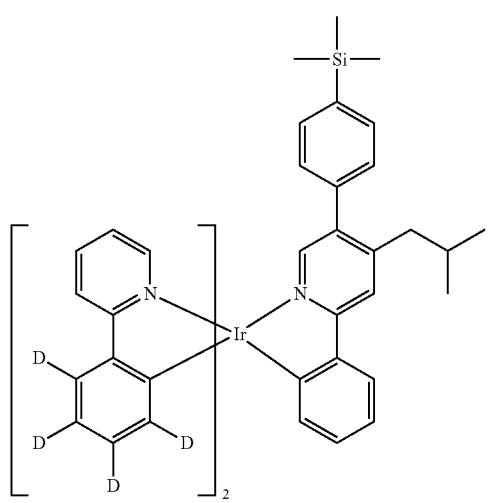
32
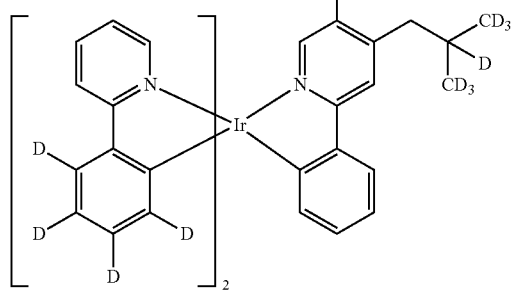
33
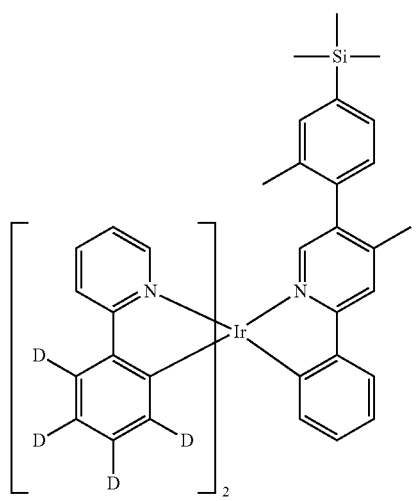
34
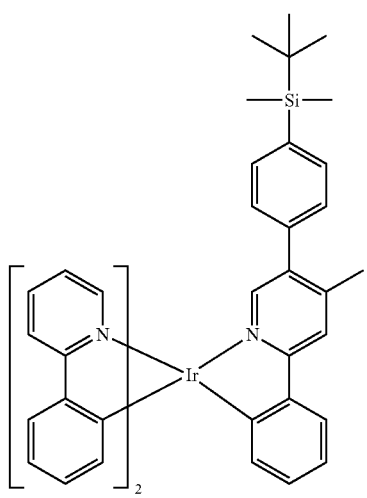
35
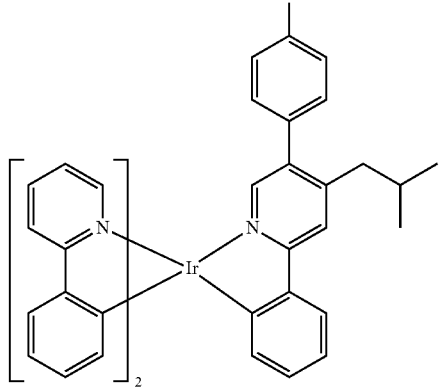
36
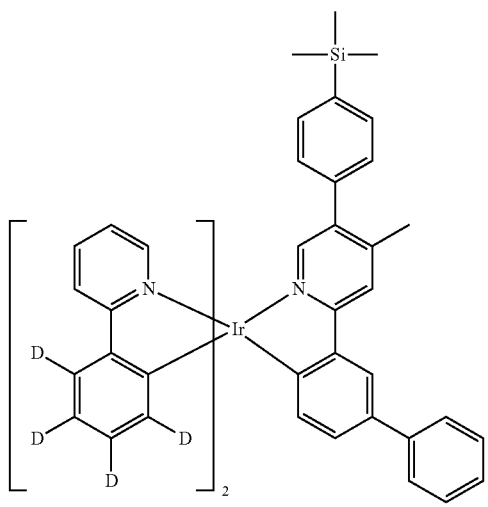

37
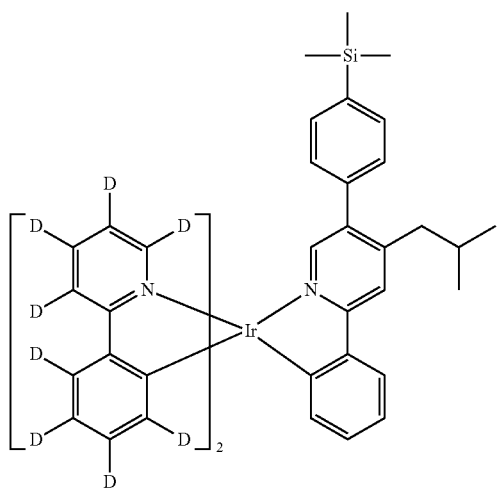
38
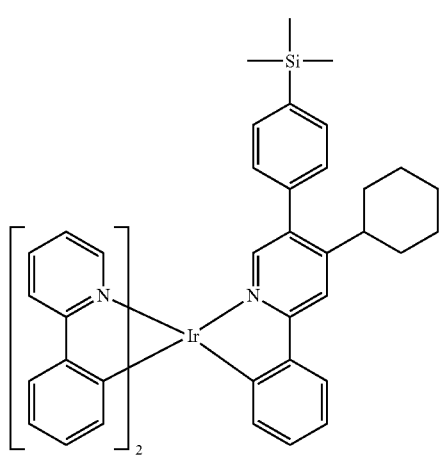
39
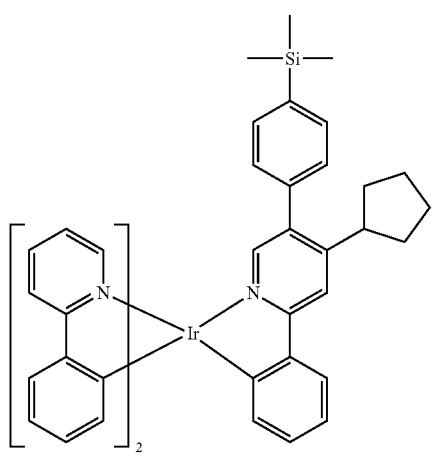
40
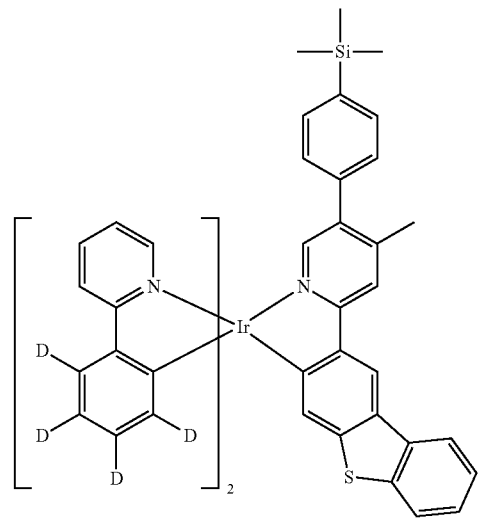
41
42

43
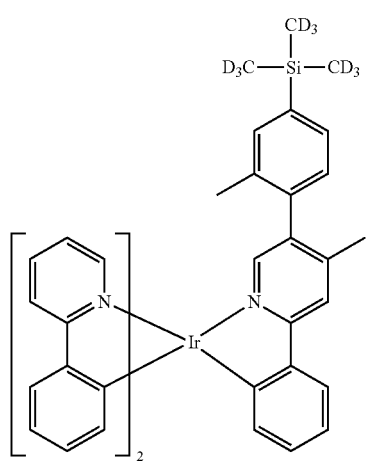
44
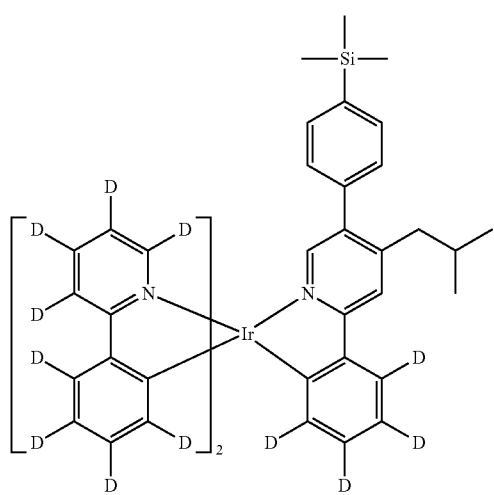
45
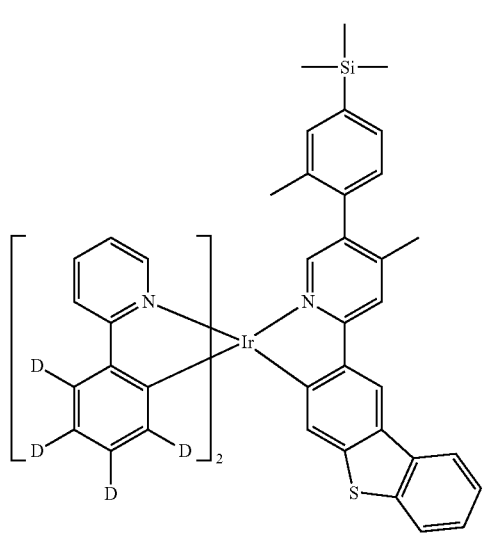
46
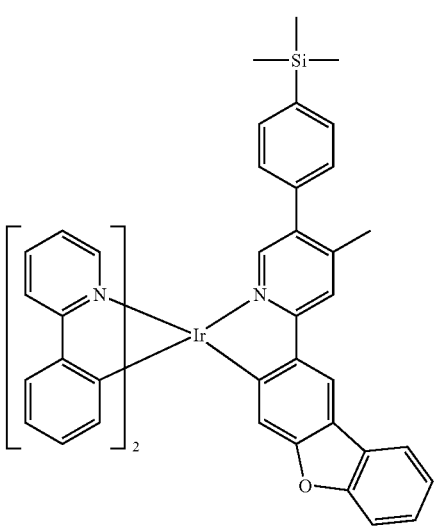
47
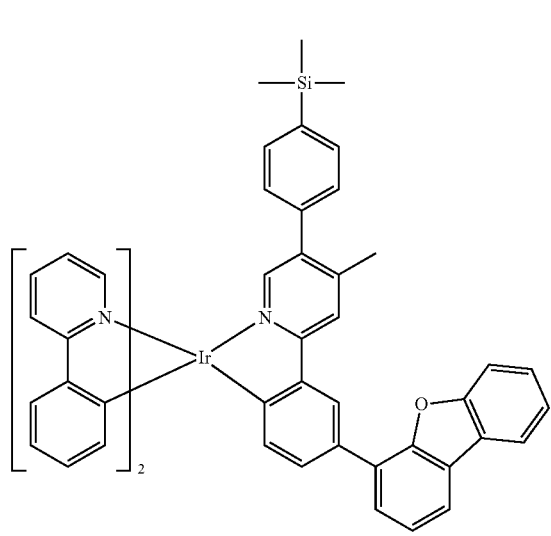
48

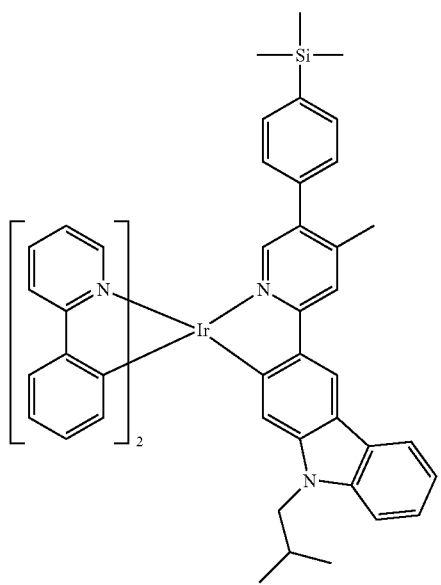
49
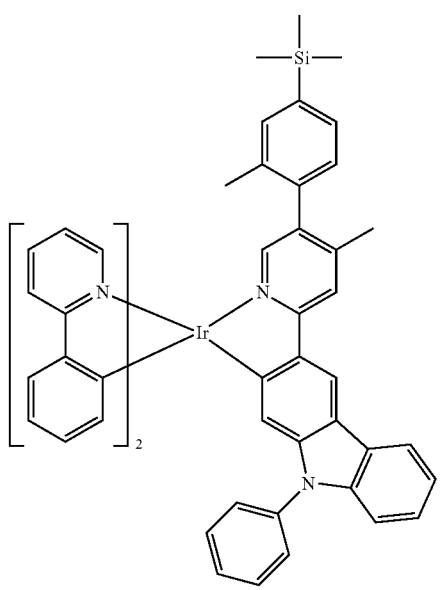
51
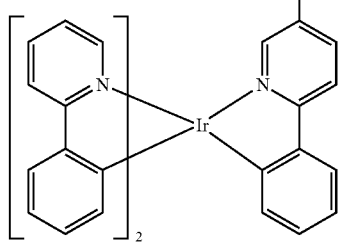
52
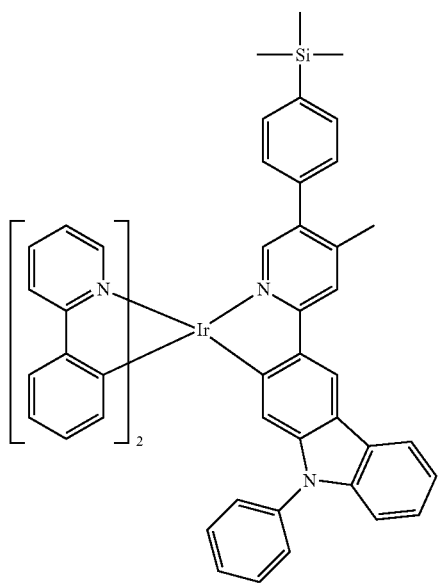
50
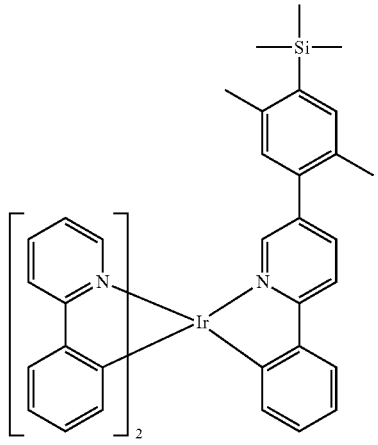
53

-continued

54

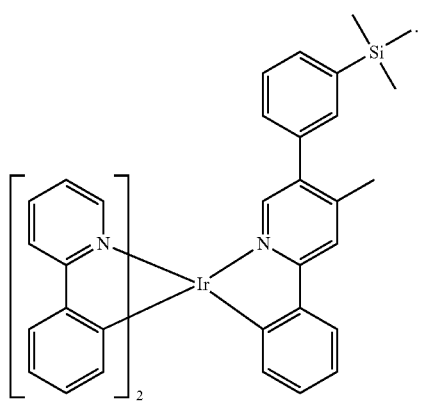

17. An organic light-emitting device comprising:
a first electrode;
a second electrode; and
an organic layer disposed between the first electrode and the second electrode,
wherein the organic layer comprises an emission layer, and at least one organometallic compound of claim 1.

18. The organic light-emitting device of claim 17, wherein the first electrode is an anode,
the second electrode is a cathode, and
the organic layer comprises:
  i) a hole transport region disposed between the first electrode and the emission layer, wherein the hole transport region comprises at least one of a hole injection layer, a hole transport layer, and an electron blocking layer, and
  ii) an electron transport region disposed between the emission layer and the second electrode, wherein the electron transport region comprises at least one selected from a hole blocking layer, an electron transport layer, and an electron injection layer.

19. The organic light-emitting device of claim 17, wherein the emission layer comprises the organometallic compound of claim 1.

20. The organic light-emitting device of claim 19, wherein the emission layer further comprises a host, and wherein an amount of the organometallic compound of claim 1 in the emission layer is smaller than an amount of the host.

* * * * *